(12) United States Patent
Reedtz-Runge et al.

(10) Patent No.: US 9,498,534 B2
(45) Date of Patent: Nov. 22, 2016

(54) DERIVATIVES OF GLP-1 LIKE PEPTIDES, AND USES THEREOF

(71) Applicant: Novo Nordisk A/S, Bagsvaerd (DK)

(72) Inventors: Steffen Reedtz-Runge, Birkeroed (DK); Jacob Kofoed, Vaerloese (DK); Christian Wenzel Tornoee, Lyngby (DK); Per Sauerberg, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 195 days.

(21) Appl. No.: 14/322,077

(22) Filed: Jul. 2, 2014

(65) Prior Publication Data

US 2015/0011462 A1 Jan. 8, 2015

Related U.S. Application Data

(60) Provisional application No. 61/845,646, filed on Jul. 12, 2013.

(30) Foreign Application Priority Data

Jul. 4, 2013 (EP) .................................... 13175094

(51) Int. Cl.
*A61K 38/26* (2006.01)
*A61K 47/48* (2006.01)
*C07K 14/605* (2006.01)

(52) U.S. Cl.
CPC ... *A61K 47/48038* (2013.01); *A61K 47/48061* (2013.01); *C07K 14/605* (2013.01); *A61K 38/26* (2013.01)

(58) Field of Classification Search
CPC .... A61K 38/22; A61K 38/26; C07K 14/575; C07K 14/605
See application file for complete search history.

(56) References Cited

U.S. PATENT DOCUMENTS

| | | | |
|---|---|---|---|
| 2007/0111940 A1* | 5/2007 | Larsen | C07K 14/605 514/11.7 |
| 2009/0215981 A1 | 8/2009 | Glaesner et al. | |
| 2011/0166321 A1 | 7/2011 | Garibay et al. | |

FOREIGN PATENT DOCUMENTS

| | | |
|---|---|---|
| WO | 00/55119 A1 | 9/2000 |
| WO | 01/35988 A1 | 5/2001 |
| WO | 0215981 A1 | 2/2002 |
| WO | 2004/093823 A2 | 11/2004 |
| WO | 2006/097537 A2 | 9/2006 |
| WO | 2006124529 A1 | 11/2006 |
| WO | 2009/030771 A1 | 3/2009 |
| WO | 2011/080102 A2 | 7/2011 |
| WO | 2012062803 A1 | 5/2012 |
| WO | 2012062804 A1 | 5/2012 |
| WO | 2012140117 A1 | 10/2012 |

OTHER PUBLICATIONS

Cummings Bethany P et al. Chronic Administration of the Glucagon-Like Peptide-1 Analog, Liraglutide, Delays the Onset of Diabetes and Lowers Triglycerides in UCD-T2DM Rats, "DIABETES" Year 2010, vol. 59, No. 10.

* cited by examiner

*Primary Examiner* — Jeffrey E Russel
(74) *Attorney, Agent, or Firm* — Richard W. Bork

(57) ABSTRACT

The invention relates to derivatives of GLP-1 like peptides which are C-terminally extended analogs of native GLP-1. The derivatives comprise two side chains, one at a position corresponding to position 42, and one at a position corresponding to position 18, 23, 27, 31, 36, or 38, wherein both positions are when compared to GLP-1(7-37). The side chains comprise a C19, C20, or C22 diacid protracting moiety and optionally a linker. The invention also relates to intermediate products in the form of novel GLP-1 analogs incorporated in the derivatives of the invention, as well as pharmaceutical compositions and medical uses of the derivatives. The derivatives have very long half-lives while maintaining a satisfactory potency, which makes them potentially suitable for once-monthly administration.

39 Claims, No Drawings

SEQUENCE LISTING

<160> NUMBER OF SEQ ID NOS: 14

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 2

His Xaa Glu Gly Thr Phe Thr Ser Asp Val Ser Ser Tyr Leu Glu Glu
1               5                   10                  15

Gln Ala Ala Arg Lys Phe Ile Ala Trp Leu Val Arg Gly Arg Gly Gly
            20                  25                  30

Gly Gly Ser Lys
        35

<210> SEQ ID NO 3
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 3

His Xaa Glu Gly Thr Phe Thr Ser Asp Val Ser Ser Tyr Leu Glu Glu
1               5                   10                  15

Gln Ala Ala Arg Glu Phe Ile Ala Lys Leu Val Arg Gly Arg Gly Gly
            20                  25                  30

Gly Gly Ser Lys
        35

<210> SEQ ID NO 4
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 4

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Lys
            20                  25                  30

Gly Gly Ser Lys
        35

<210> SEQ ID NO 5
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)

```
<223> OTHER INFORMATION: Aib (2-Aminoisobutyric acid)

<400> SEQUENCE: 5

His Xaa Glu Gly Thr Phe Thr Ser Asp Val Ser Ser Tyr Leu Glu Glu
1               5                   10                  15

Lys Ala Ala Arg Glu Phe Ile Ala Trp Leu Val Arg Gly Arg Gly Gly
            20                  25                  30

Gly Gly Ser Lys
        35

<210> SEQ ID NO 6
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 6

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly Gly
            20                  25                  30

Gly Gly Ser Lys
        35

<210> SEQ ID NO 7
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 7

His Xaa Glu Gly Thr Phe Thr Ser Asp Val Ser Lys Tyr Leu Glu Glu
1               5                   10                  15

Gln Ala Ala Arg Glu Phe Ile Ala Trp Leu Val Arg Gly Arg Gly Gly
            20                  25                  30

Gly Gly Ser Lys
        35

<210> SEQ ID NO 8
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 8

Xaa Xaa Glu Gly Thr Phe Thr Ser Asp Val Ser Ser Tyr Leu Glu Glu
1               5                   10                  15
```

Gln Ala Ala Arg Glu Phe Ile Ala Trp Leu Val Arg Gly Arg Gly Lys
            20                  25                  30

Gly Gly Ser Lys
        35

<210> SEQ ID NO 9
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 9

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly Ala
            20                  25                  30

Glu Ser Pro Lys
        35

<210> SEQ ID NO 10
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 10

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly Glu
            20                  25                  30

Gly Pro Ala Lys
        35

<210> SEQ ID NO 11
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 11

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly Pro
            20                  25                  30

Ala Ser Glu Lys
        35

<210> SEQ ID NO 12
<211> LENGTH: 36

```
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 12

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Lys
            20                  25                  30

Pro Glu Gly Lys
        35

<210> SEQ ID NO 13
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 13

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Lys
            20                  25                  30

Ser Ala Glu Lys
        35

<210> SEQ ID NO 14
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Aib (2-Aminoisobutyric acid)

<400> SEQUENCE: 14

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Lys
            20                  25                  30

Ser Pro Glu Lys
        35
```

DERIVATIVES OF GLP-1 LIKE PEPTIDES, AND USES THEREOF

CROSS-REFERENCE TO RELATED APPLICATIONS

This application claims priority under 35 U.S.C. §119 of U.S. Provisional Application 61/845,646, filed Jul. 12, 2013; this application further claims priority of European Application 13175094.5, filed Jul. 4, 2013; the contents of all above-named applications are incorporated herein by reference.

TECHNICAL FIELD

The present invention relates to derivatives of GLP-1 like peptides, which may be defined as C-terminally extended analogues of glucagon-like peptide 1 (GLP-1). The derivatives are double-acylated, and one of the acyl side chains is attached to the C-terminal amino acid of the GLP-1 like peptide. The invention also relates to the pharmaceutical use of these derivatives.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun. 27, 2014. The Sequence Listing is made up of 8 kilobytes, and the information contained in the attached "SEQUENCE LISTING" is identical to the information in the specification as originally filed. No new matter is added.

BACKGROUND

WO 2009/030771 A1 and WO 2011/080102 disclose a number of mono-acylated GLP-1 derivatives including some that are acylated with C12-C20 fatty diacids.

WO 2012/140117 A1, WO 2012/062803 A1 and WO 2012/062804 A1 disclose a number of double-acylated GLP-1 derivatives including some that are acylated with C12-C18 fatty diacids.

SUMMARY

Liraglutide is a GLP-1 derivative for once daily administration. It is marketed under the trade name of VICTOZA® by Novo Nordisk A/S.

Semaglutide is a GLP-1 derivative for once weekly administration. It is under development by Novo Nordisk A/S. This compound is disclosed in WO 2006/097537 Example 4.

The invention relates to derivatives of GLP-1 like peptides which have potential for once monthly administration.

In one aspect the invention relates to derivatives of GLP-1 like peptides, which are double-acylated. One of the acylation sites is at the C-terminus, more in particular at the position which when compared with native GLP-1(7-37) would correspond to position number 42. The other acylation site is internally in the GLP-1 like peptide, more in particular at one of the positions corresponding to position 18, 23, 27, 31, 36, or 38 in native GLP-1(7-37). A long fatty diacid is used for both of the two acylations.

In a second aspect the invention relates to pharmaceutical compositions comprising such derivatives and pharmaceutically acceptable excipients, as well as the medical use of the derivatives.

In a third aspect, the invention relates to intermediate products in the form of novel GLP-1 analogues, which can be incorporated in the derivatives of the invention. Such analogues may comprise the following amino acid changes when compared to GLP-1 (7-37) (SEQ ID NO: 1): i) (8Aib, 22E, 26R, 27K, 34R, 38G, 39G, 40G, 41S, 42K); ii) (8Aib, 22E, 26R, 31K, 34R, 38G, 39G, 40G, 41S, 42K); iii) (8Aib, 22E, 26R, 34R, 38K, 39G, 40G, 41S, 42K); iv (8Aib, 22E, 23K, 26R, 34R, 38G, 39G, 40G, 41S, 42K); v) (8Aib, 22E, 26R, 34R, 36K, 38G, 39G, 40G, 41S, 42K); vi) (8Aib, 18K, 22E, 26R, 34R, 38G, 39G, 40G, 41S, 42K); vii) (7Imp, 8Aib, 22E, 26R, 34R, 38K, 39G, 40G, 41S, 42K); iix) (8Aib, 22E, 26R, 34R, 36K, 38A, 39E, 40S, 41P, 42K); ix) (8Aib, 22E, 26R, 34R, 36K, 38E, 39G, 40P, 41A, 42K); x) (8Aib, 22E, 26R, 34R, 36K, 38P, 39A, 40S, 41E, 42K); xi) (8Aib, 22E, 26R, 34R, 38K, 39P, 40E, 41G, 42K) (SEQ ID NO: 12); xii) (8Aib, 22E, 26R, 34R, 38K, 39S, 40A, 41E, 42K); or xiii) (8Aib, 22E, 26R, 34R, 38K, 39S, 40P, 41E, 42K).

The amino acid sequence of native human GLP-1(7-37) is included in the sequence listing as SEQ ID NO: 1 and SEQ ID NO's 2-14 are specific GLP-1 analogues of the GLP-1 derivatives of the invention.

The derivatives of the invention represent a remarkable leap in the search for GLP-1 derivatives of very long half-lives and still with a very good potency.

DESCRIPTION

In what follows, Greek letters may be represented by their symbol or the corresponding written name, for example: α=alpha; β=beta; ε=epsilon; γ=gamma; δ=delta; ω=omega; etc. Also, the Greek letter of μ may be represented by "u", e.g. in μl==ul, or in μM=uM.

An asterisk (*) in a chemical formula designates i) a point of attachment, ii) a radical, and/or iii) an unshared electron.

In its first aspect the invention relates to a derivative of a GLP-1 like peptide, wherein the GLP-1 like peptide comprises a peptide of formula I:

$Xaa_7\text{-}Xaa_8\text{-}Glu\text{-}Gly\text{-}Thr\text{-}Xaa_{12}\text{-}Thr\text{-}Ser\text{-}Asp\text{-}Xaa_{16}\text{-}Ser\text{-}Xaa_{18}\text{-}Xaa_{19}\text{-}Xaa_{20}\text{-}Glu\text{-}Xaa_{22}\text{-}Xaa_{23}\text{-}Ala\text{-}Xaa_{25}\text{-}Xaa_{26}\text{-}Xaa_{27}\text{-}Phe\text{-}Ile\text{-}Xaa_{30}\text{-}Xaa_{31}\text{-}Leu\text{-}Xaa_{33}\text{-}Xaa_{34}\text{-}Xaa_{35}\text{-}Xaa_{36}\text{-}Xaa_{37}\text{-}Xaa_{38}\text{-}Xaa_{39}\text{-}Xaa_{40}\text{-}Xaa_{41}\text{-}Xaa_{42}$, wherein $Xaa_7$ is L-histidine, (S)-2-Hydroxy-3-(1H-imidazol-4-yl)-propionic acid, D-histidine, desamino-histidine, homohistidine, $N^\alpha$-acetyl-histidine, $N^\alpha$-formyl-histidine, $N^\alpha$-methyl-histidine, 3-pyridylalanine, 2-pyridylalanine, or 4-pyridylalanine; $Xaa_8$ is Ala, Gly, Ser, Aib, (1-aminocyclopropyl) carboxylic acid, or (1-aminocyclobutyl)carboxylic acid; $Xaa_{12}$ is Phe or Leu; $Xaa_{16}$ is Val or Leu; $Xaa_{18}$ is Ser, Arg, Lys, Val, or Leu; $Xaa_{19}$ is Tyr or Gln; $Xaa_{20}$ is Leu or Met; $Xaa_{22}$ is Gly or Glu; $Xaa_{23}$ is Gln, Glu, Lys, or Arg; $Xaa_{25}$ is Ala or Val; $Xaa_{26}$ is Arg or Lys; $Xaa_{27}$ is Glu, Lys, or Leu; $Xaa_{30}$ is Ala, Glu, or Arg; $Xaa_{31}$ is Trp, Lys, or His; $Xaa_{33}$ is Val, Lys, or Arg; $Xaa_{34}$ is Lys, Arg, His, Asn, or Gln; $Xaa_{35}$ is Gly or Ala; $Xaa_{36}$ is Arg, Lys, or Gly; $Xaa_{37}$ is Gly or Pro; $Xaa_{38}$ is Ser, Gly, Ala, Glu, Pro, or Lys; $Xaa_{39}$ is Ser, Gly, Ala, Glu, or Pro; $Xaa_{40}$ is Ser, Gly, Ala, Glu, or Pro; $Xaa_{41}$ is Ser, Gly, Ala, Glu, or Pro; and $Xaa_{42}$ is Lys; with the proviso that at least one of $Xaa_{18}$, $Xaa_{23}$, $Xaa_{27}$, $Xaa_{31}$, $Xaa_{36}$, or $Xaa_{38}$ is Lys; wherein Lys at $Xaa_{42}$ is a first K residue, and a Lys at one of $Xaa_{18}$, $Xaa_{23}$, $Xaa_{27}$, $Xaa_{31}$, $Xaa_{36}$, or $Xaa_{38}$ is a second K residue; which derivative comprises a first and a second protracting moiety connected to said first and second K residue, respectively, wherein the first and the second protracting moiety is of formula Chem. 1: HOOC—$(CH_2)_{18}$—CO—*, Chem. 1a: HOOC—$(CH_2)_{17}$ —CO—*, or Chem. 1b: HOOC—$(CH_2)_{20}$—CO—*; or a pharmaceutically acceptable salt, amide, or ester thereof.

In its second aspect, the invention relates to a pharmaceutical composition comprising a derivative of the invention and a pharmaceutically acceptable excipient; and the use of the derivative or analogue of the invention as a medicament, in particular for use in the (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C; (ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes; (iii) improving β-cell function, such as decreasing β-cell apoptosis, increasing β-cell function and/or β-cell mass, and/or for restoring glucose sensitivity to β-cells; (iv) prevention and/or treatment of cognitive disorders and/or neurodegenerative disorders, such as Alzheimer's disease, Parkinson's disease, and/or multiple sclerosis; (v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence; (vi) prevention and/or treatment of diabetic complications, such as angiopathy; neuropathy, including peripheral neuropathy; nephropathy; and/or retinopathy; (vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo; (viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure; (ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus; (x) prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness; (xi) prevention and/or treatment of polycystic ovary syndrome (PCOS); (xii) prevention and/or treatment of cerebral disease, such as cerebral ischemia, cerebral haemorrhage, and/or traumatic brain injury; (xiii) prevention and/or treatment of sleep apnoea; and/or (xiv) prevention and/or treatment of abuse, such as alcohol abuse and/or drug abuse.

In its third aspect, the invention relates to an intermediate product in the form of a GLP-1 analogue, which comprises the following amino acid changes when compared to GLP-1 (7-37) (SEQ ID NO: 1):

i) (8Aib, 22E, 26R, 27K, 34R, 38G, 39G, 40G, 41S, 42K);
ii) (8Aib, 22E, 26R, 31K, 34R, 38G, 39G, 40G, 41S, 42K);
iii) (8Aib, 22E, 26R, 34R, 38K, 39G, 40G, 41S, 42K); iv (8Aib, 22E, 23K, 26R, 34R, 38G, 39G, 40G, 41S, 42K); v) (8Aib, 22E, 26R, 34R, 36K, 38G, 39G, 40G, 41S, 42K); vi) (8Aib, 18K, 22E, 26R, 34R, 38G, 39G, 40G, 41S, 42K); vii) (7Imp, 8Aib, 22E, 26R, 34R, 38K, 39G, 40G, 41S, 42K); iix) (8Aib, 22E, 26R, 34R, 36K, 38A, 39E, 40S, 41P, 42K); ix) (8Aib, 22E, 26R, 34R, 36K, 38E, 39G, 40P, 41A, 42K); x) (8Aib, 22E, 26R, 34R, 36K, 38P, 39A, 40S, 41E, 42K); xi) (8Aib, 22E, 26R, 34R, 38K, 39P, 40E, 41G, 42K) (SEQ ID NO: 12); xii) (8Aib, 22E, 26R, 34R, 38K, 39S, 40A, 41E, 42K); or xiii) (8Aib, 22E, 26R, 34R, 38K, 39S, 40P, 41E, 42K); or which is selected from these analogues.

GLP-1 Receptor Agonist

A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to native GLP-1.

Structural Features

GLP-1 Like Peptides and Analogues of GLP-1

The term "GLP-1 like peptide" as used herein may be referred to as an analogue (or variant) of the human glucagon-like peptide-1 (GLP-1(7-37)), the sequence of which is included in the sequence listing as SEQ ID NO: 1. The peptide having the sequence of SEQ ID NO: 1 may also be designated "native" GLP-1.

The GLP-1 like peptide of the invention may be defined by the following formula I:

$Xaa_7$-$Xaa_8$-Glu-Gly-Thr-$Xaa_{12}$-Thr-Ser-Asp-$Xaa_{16}$-
Ser-$Xaa_{18}$-$Xaa_{19}$-$Xaa_{20}$-Glu-$Xaa_{22}$-$Xaa_{23}$-Ala-
$Xaa_{25}$-$Xaa_{26}$-$Xaa_{27}$-Phe-Ile-$Xaa_{30}$-$Xaa_{31}$-Leu-
$Xaa_{33}$-$Xaa_{34}$-$Xaa_{35}$-$Xaa_{36}$-$Xaa_{37}$-$Xaa_{38}$-$Xaa_{39}$-
$Xaa_{40}$-$Xaa_{41}$-$Xaa_{42}$, wherein $Xaa_7$ is L-histidine, (S)-2-Hydroxy-3-(1H-imidazol-4-yl)-propionic acid, D-histidine, desamino-histidine, homohistidine, $N^α$-acetyl-histidine, $N^α$-formyl-histidine, $N^α$-methyl-histidine, 3-pyridylalanine, 2-pyridylalanine, or 4-pyridylalanine; $Xaa_8$ is Ala, Gly, Ser, Aib, (1-aminocyclopropyl)carboxylic acid, or (1-aminocyclobutyl)carboxylic acid; $Xaa_{12}$ is Phe or Leu; $Xaa_{16}$ is Val or Leu; $Xaa_{18}$ is Ser, Arg, Lys, Val, or Leu; $Xaa_{19}$ is Tyr or Gln; $Xaa_{20}$ is Leu or Met; $Xaa_{22}$ is Gly or Glu; $Xaa_{23}$ is Gln, Glu, Lys, or Arg; $Xaa_{25}$ is Ala or Val; $Xaa_{26}$ is Arg or Lys; $Xaa_{27}$ is Glu, Lys, or Leu; $Xaa_{30}$ is Ala, Glu, or Arg; $Xaa_{31}$ is Trp, Lys, or His; $Xaa_{33}$ is Val, Lys, or Arg; $Xaa_{34}$ is Lys, Arg, His, Asn, or Gln;

Xaa$_{35}$ is Gly or Ala; Xaa$_{36}$ is Arg, Lys, or Gly; Xaa$_{37}$ is Gly or Pro; Xaa$_{38}$ is Ser, Gly, Ala, Glu, Pro, or Lys; Xaa$_{39}$ is Ser, Gly, Ala, Glu, or Pro; Xaa$_{40}$ is Ser, Gly, Ala, Glu, or Pro; Xaa$_{41}$ is Ser, Gly, Ala, Glu, or Pro; and Xaa$_{42}$ is Lys; with the proviso that at least one of Xaa$_{18}$, Xaa$_{23}$, Xaa$_{27}$, Xaa$_{31}$, Xaa$_{36}$, or Xaa$_{38}$ is Lys.

In this formula the numbering of the amino acid residues follows the established practice in the art for native GLP-1, namely that the first (N-terminal) amino acid residue is numbered or accorded position no. 7, and the subsequent amino acid residues downstream towards the C-terminus are numbered 8, 9, 10, and so on, until the last (C-terminal) amino acid residue, which in native GLP-1 is Gly with number 37, however the peptide of formula I has a C-terminal tail or extension, as defined in the formula, up to and including position 42.

The numbering is done differently in the sequence listing, where the first amino acid residue of (SEQ ID NO: 1 (His) is assigned no. 1, and the last (Gly) no. 31, and vice versa for the other GLP-1 sequences of the sequence listing. However, herein we follow the established numbering practice in the art, as explained above.

Each of the GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

In other words, the GLP-1 analogue of the invention may be described by reference to the native GLP-1(7-37) peptide, namely as a variant thereof in which a number of amino acid residues have been changed when compared to native GLP-1(7-37) (SEQ ID NO: 1). These changes may represent, independently, one or more amino acid substitutions, additions, and/or deletions.

The following are non-limiting examples of suitable analogue nomenclature:

The GLP-1 like peptide incorporated in the derivative of Example 3 herein may be referred to as the following GLP-1 analogue: (8Aib, 22E, 26R, 34R, 38K, 39G, 40G, 41S, 42K) GLP-1(7-37). This means that when this analogue is aligned with native GLP-1, it has i) an Aib at the position in the analogue which corresponds, according to the alignment, to position 8 in native GLP-1, ii) an E at the position in the analogue which corresponds to position 22 in native GLP-1, iii) an R at the position in the analogue which corresponds to position 26 in native GLP-1, iv) an R at the position in the analogue which corresponds to position 34 in native GLP-1, v) a K at the position in the analogue which would correspond to position 38 in native GLP-1 (if extended at the C-terminus), vi) a G at the position in the analogue which would correspond to position 39 in native GLP-1 (if extended at the C-terminus), vii) a G at the position in the analogue which would correspond to position 40 in native GLP-1 (if extended at the C-terminus), iix) an S at the position in the analogue which would correspond to position 41 in native GLP-1 (if extended at the C-terminus), and ix) a K at the position in the analogue which would correspond to position 42 in native GLP-1 (if extended at the C-terminus). All other amino acids in this analogue are identical to the corresponding amino acid in native GLP-1. As explained above, the GLP-1 like peptide of the invention may be defined by amino acid changes when and as compared to native GLP-1. The amino acid changes discussed above may be thought of as amino acid substitutions and amino acid additions, relative to native GLP-1. In this example the additions are at the C-terminus, and they may thus also be referred to as C-terminal extensions. For example, 38K refers to the amino acid K being found at the position C-terminally next to the position which corresponds to position 37 in native GLP-1, when the analogue is aligned with native GLP-1. And then follows at the next position C-terminally G at the position in the analogue which would correspond to position 39 of native GLP-1; and another G at the subsequent position C-terminally, in the position in the analogue which would correspond to position 40 of native GLP-1; and an S at the subsequent position C-terminally, in the position in the analogue which would correspond to position 41 of native GLP-1, and lastly a K at the position which would correspond to position 42 of native GLP-1.

The general formula I is to be understood in a similar manner.

In a particular embodiment at least one of Xaa$_{18}$, Xaa$_{23}$, Xaa$_{27}$, Xaa$_{31}$, Xaa$_{36}$, or Xaa$_{38}$ in formula I is Lys. The GLP-1 like peptide of the invention comprises at least one more Lys residue, namely at position 42 (Xaa$_{42}$). The latter (pos. 42) may be referred to as the first K residue, and the former, i.e. a Lys at one of Xaa$_{18}$, Xaa$_{23}$, Xaa$_{27}$, Xaa$_{31}$, Xaa$_{36}$, or Xaa$_{38}$, may be referred to as the second K residue. The first and the second K residue constitute two acylation sites of the double-acylated derivative of the invention. The GLP-1 like peptide of the invention may comprise additional Lys residues, as it is clear from Formula I. In a particular embodiment the GLP-1 like peptide of the invention has only two Lys residues.

Analogues "comprising" certain specified changes may comprise further changes, when compared to SEQ ID NO: 1. In a particular embodiment, the analogue "has" the specified changes.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a variant GLP-1(7-37) sequence by reference to a reference sequence such as native GLP-1(7-37) (SEQ ID NO: 1). Equivalent or corresponding positions, as well as the number of changes, are easily deduced, e.g. by simple handwriting and eyeballing; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted below, in which sequence no. 1 is SEQ ID NO: 1, and sequence no. 2 is the analogue (8Aib, 22E, 26R, 34R, 38K, 39G, 40G, 41S, 42K) SEQ ID NO: 4 thereof:

```
# Aligned_sequences: 2
# sequence 1: 1
# sequence 2: 2
# Matrix: EBLOSUM62
# Gap_penalty: 10.0
# Extend_penalty: 0.5

# Length: 36
# Identity:      27/36 (75.0%)
# Similarity:    29/36 (80.6%)
# Gaps:           5/36 (13.9%)
# Score: 143.0

1      1 HAEGTFTSDVSSYLEGQAAKEFIAWLVKGRG----- 31
             |.||||||||||||.|||:||||||:|||
  2      1 HXEGTFTSDVSSYLEEQAAREFIAWLVRGRGKGGSK 36
```

When 6 is added to the position numbers shown in this alignment (i.e., to "1" and "31" in sequence 1, and to "1" and "37" in sequence 2) one gets the position numbering as used herein. For example, in sequence 1 (which is identical to SEQ ID NO: 1), the N-terminal amino acid (H) has position number 7, and the C-terminal amino acid (G) has number 37. Regarding sequence 2, the N-terminal amino acid (H) has number 7 and the C-terminal amino acid (K) has number 42.

In case specific amino acid residues or the like with no one-letter codon (such as Aib) are included in the sequence these may, for alignment purposes, be replaced with, e.g., X, as shown in the above alignment. If desired, X can later be manually corrected.

The following are non-limiting examples of what can be inferred from the above alignment:

As one example it can be inferred that sequence 2 has 9 amino acid changes as compared to sequence 1 (namely at all those positions where a full stop ("."), a colon (":"), or a horizontal hyphen ("-") is shown in the alignment).

As another example it can be inferred that, e.g., sequence no. 2 comprises 38K, since it has a K at the position which corresponds, according to the alignment, to position 38 in the reference sequence (sequence 1, SEQ ID NO: 1).

And similarly all other changes in sequence 2 as compared to sequence 1 can be deduced from the alignment.

The term "peptide", as e.g. used in the context of the GLP-1 like peptide of the derivatives of the invention, refers to a compound which comprises a series of amino acids interconnected by amide (or peptide) bonds.

The peptide of the invention comprises at least 36 amino acids. In a particular embodiment the peptide is composed of 36 amino acids. In an additional particular embodiment the peptide consists of 36 amino acids.

In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid, or 2-Aminoisobutyric acid), des-aminohistidine (alternative name imidazopropionic acid or 3-(Imidazol-5-yl)propanoic acid, abbreviated Imp), as well as the D-isomers of the proteinogenic amino acids.

In what follows, each amino acid of the GLP-1 peptide for which the optical isomer is not stated is to be understood to mean the L-isomer (unless otherwise specified).

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assays described in Examples 29, 30, 32, or 33 herein.

Derivatives of GLP-1 Like Peptides

The term "GLP-1 derivative" generally refers to a compound which may be prepared from the native GLP-1 peptide or an analogue thereof by chemical modification, in particular by covalent attachment of one or more substituents. The derivative of a GLP-1 like peptide according to the invention comprises two such substituents. Each of these may, also or alternatively, be referred to as a side chain.

In a particular embodiment, the side chain is capable of forming non-covalent complexes with albumin, thereby promoting the circulation of the derivative with the blood stream, and also having the effect of protracting the time of action of the derivative, due to the fact that the complex of the GLP-1-derivative and albumin is only slowly disintegrated to release the active pharmaceutical ingredient. Thus, the substituent, or side chain, as a whole is preferably referred to as an albumin binding moiety.

In another particular embodiment the albumin binding moiety comprises a portion which is particularly relevant for the albumin binding and thereby the protraction, which portion may accordingly be referred to as a protracting moiety. The protracting moiety may be near, preferably at, the terminal (or distal, or free) end of the albumin binding moiety, relative to its point of attachment to the peptide. The albumin binding moiety is attached to the peptide by acylation of a lysine residue of the peptide, in particular by acylation to the epsilon-amino group of the lysine residue.

In a still further particular embodiment the albumin binding moiety comprises a portion between the protracting moiety and the point of attachment to the peptide, which portion may be referred to as a linker, linker moiety, spacer, or the like.

The derivatives of the invention comprise a first and a second protracting moiety of formula Chem. 1, Chem. 1a, or Chem. 1b:

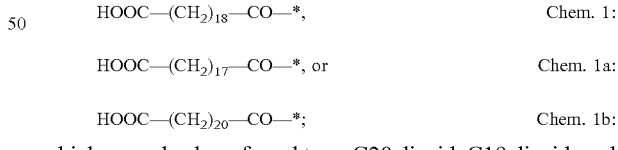

which may also be referred to as C20 diacid, C19 diacid, and C22 diacid, respectively. The first protracting moiety is connected to the first K residue, and the second protracting moiety is connected to the second K residue. The term "connected" is intended to include direct as well as indirect attachment. An example of indirect attachment is attachment via a linker placed between the protracting moiety and the K residue. An example of direct attachment is when there is no such intervening linker.

Thus, in a particular embodiment the first protracting moiety is attached to the first K residue, and the second protracting moiety is attached to the second K residue, optionally via a first and a second linker, respectively.

The first and the second linker may comprise an element_1, which is a Glu di-radical of formula Chem. 2:

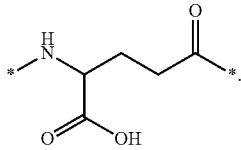

Chem. 2

This element may be referred to as gamma-Glu, or briefly gGlu, due to the fact that it is the gamma carboxy group of the amino acid glutamic acid which is here used for connection to another linker element, or to the epsilon-amino group of lysine, as the case may be.

Also, or alternatively, the first and the second linker may comprise an element_2 of formula Chem. 3:

Chem. 3

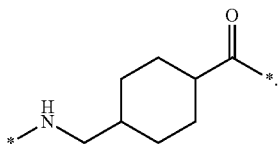

wherein k is an integer in the range of 1-5, and n is an integer in the range of 1-5. In a particular embodiment, when k=1 and n=1, the Chem. 3 element_2 may be designated OEG, or a di-radical of 8-amino-3,6-dioxaoctanoic acid. In an additional non-limiting particular embodiment k=3 and n=2, in which case the element_2 group of Chem. 3 may be designated dPEG4.

Also, or alternatively, the first and the second linker may comprise an element_3 of formula Chem. 4, which may be referred to as Trx (for tranexamic acid):

Chem. 4

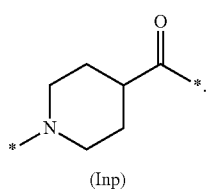

Also, or alternatively, the first and the second linker may comprise an element_4 of formula Chem. 5: *—NH—$(CH_2)_q$—CH[$(CH_2)_w$—$NH_2$]—CO—*, wherein q is an integer in the range of 0-5, and w is an integer in the range of 0-5, with the provisos that when w is 0 q is an integer in the range of 1-5, and when q is 0 w is an integer in the range of 1-5.

Also, or alternatively, the first and the second linker may comprise an element_5 of formula Chem. 6:

Chem. 6

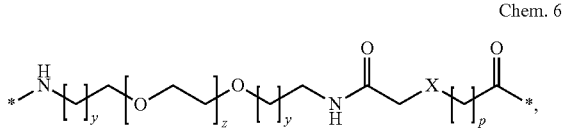

wherein y is 1 or 2, z is 1 or 2, p is 0 or 1, and X designates a carbon atom or an oxygen atom.

Particular non-limiting embodiments of element_5 are Chem. 7, Chem. 8, and Chem. 9:

Chem. 7

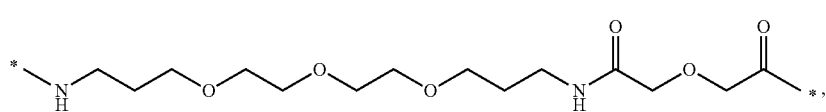

(TotaGlyc)

Chem. 8

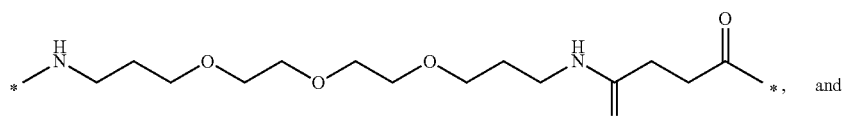

(TtdSuc), and

Chem. 9

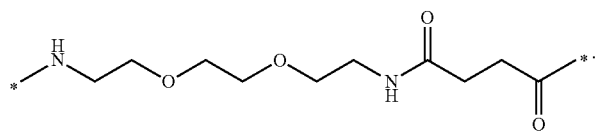

(DooaSuc)

Also, or alternatively, the first and the second linker may comprise an element_6 of formula Chem. 10:

Chem. 10

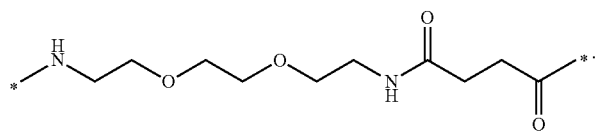

(Inp)

The first and the second protracting moieties are connected to the first and the second linkers, respectively, and in turn to the first and the second K residue, respectively, of the GLP-1 like peptide via amide bonds.

The first and the second linker may comprise one or more of the various elements as defined above (element_1 to element_6), each element may occur one or more times, and also the sequence of the elements may vary.

Whenever a linker is said to "comprise" a certain element, it may in addition contain other elements, whereas the term "incorporates" is intended to mean the same as "has" or "includes only". Therefore, a linker which "incorporates" two elements_2 of formula Chem. 3 has only two of these elements in its structure.

Various particular combinations of linker elements are described in more detail below in the section headed "Particular embodiments". The sequence in which the elements are indicated here is generally from the N-terminus to the C-terminus.

In a particular embodiment, the two albumin binding moieties (i.e. the two side chains) are similar, preferably substantially identical, or, most preferably, identical.

In another particular embodiment, the first and the second protracting moieties are similar, preferably substantially identical, or, most preferably, identical.

In a still further particular embodiment, the first and the second linkers are similar, preferably substantially identical, or, most preferably identical.

The term "substantially identical" includes differences from identity which are due to formation of one or more least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008-both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted below, in which a known entire side chain of a known GLP-1 derivative was compared with a methyl ester thereof:

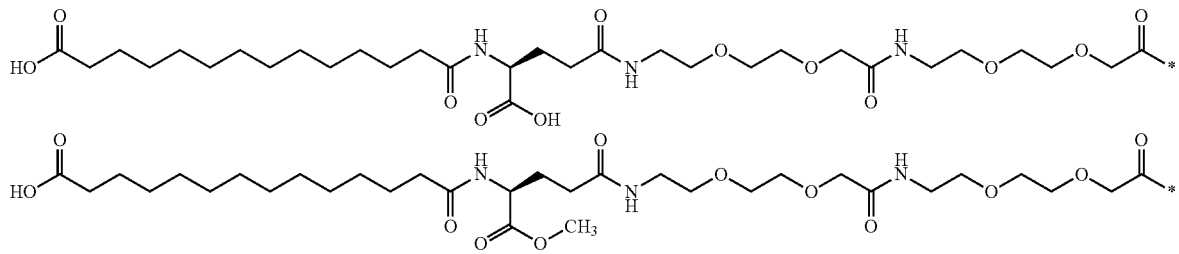

esters and/or amides; preferably formation of one or more methyl esters, and simple amides; more preferably formation of no more than two methyl esters, and/or simple amides; or most preferably formation of no more than one methyl ester, and/or simple amide.

In the context of chemical compounds such as the albumin binding moieties, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b), or c) is used, the two protracting moieties, the two linkers, and/or the two entire side chains, respectively, have a similarity of at least 0.5 (50%); preferably at least 0.6 (60%); more preferably at Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO 2009/030738 on p. 116-118. A preferred assay is the LOCI assay, where LOCI refers to Luminescence Oxygen Channeling Immunoasssay, which is generally described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immunocomplex. Illumination of the complex released singlet oxygen atoms from the donor beads, which were channelled into the acceptor beads and triggered chemiluminescence which was measured in an Envision plate reader. The amount of light was proportional to the concentration of the compound.

Pharmaceutically Acceptable Salt, Amide, or Ester

The derivatives, analogues, and intermediate products of the invention may be in the form of a pharmaceutically acceptable salt, amide, or ester.

Salts are e.g. formed by a chemical reaction between a base and an acid, e.g.: $2NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions between anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

In a particular embodiment the derivatives and analogues of the invention are basic salts. The salts may, e.g., be formed between anionic groups in the peptide moiety and added sodium or potassium cations.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a particular embodiment the derivatives of the invention have a very long half-life and at the same time a very good potency in vitro and in vivo, which makes them potentially suitable for once-monthly administration.

Thus, in a first functional aspect, the derivatives of the invention have a good potency. Also, or alternatively, in a second aspect, they bind very well to the GLP-1 receptor, e.g. at a high concentration of albumin. Preferably they are potent GLP-1 receptor agonists as is reflected by their ability to bind strongly to the GLP-1 receptor combined with the capacity to activate the receptor. Also, or alternatively, in a third functional aspect, they have improved pharmacokinetic properties.

Biological Activity—In Vitro Potency

According to the first functional aspect, the derivatives of the invention, as well as the constituent GLP-1 like peptides as such, are biologically active, or potent.

In a particular embodiment, potency and/or activity refers to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 29.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$ value, the better the potency.

In a particular embodiment, the derivatives of the invention are very potent, despite the fact that they have very long half-lives. In a particular embodiment, the derivative of the invention has an in vitro potency determined using the method of Example 29 corresponding to an $EC_{50}$ at or below 400 μM.

Biological Activity—In Vivo Pharmacology

In another particular embodiment the derivatives of the invention as well as the constituent GLP-1 like peptides as such are potent in vivo, which may be determined as is known in the art in any suitable animal model, as well as in clinical trials.

The diabetic db/db mouse is one example of a suitable animal model, and the blood glucose and/or body weight lowering effect may be determined in such mice in vivo, e.g. as described in Example 32. In a particular embodiment the derivatives of the invention are capable of lowering blood glucose and body weight in db/db mice for at least up to 96 hours.

The LYD pig is another example of a suitable animal model, and the reduction in food intake may be determined in a PD study in such pigs in vivo, e.g. as described in Example 33.

In a particular embodiment the derivatives of the invention are very potent in vivo and over a long time, which is evidenced by the results found in the experimental part and also referred to in the section headed "Particular embodiments".

Biological Activity—In Vitro Receptor Binding

According to the second functional aspect, the derivatives of the invention, as well as the constituent GLP-1 like peptides as such bind very well to the GLP-1 receptor, e.g. at a high concentration of albumin. This may be determined as described in Example 30.

Generally, the binding to the GLP-1 receptor at low albumin concentration should be as good as possible, corresponding to a low $IC_{50}$ value.

The $IC_{50}$ value at high albumin concentration reflects the influence of serum albumin on the binding of the derivative to the GLP-1 receptor. As is known, the GLP-1 derivatives can bind to serum albumin and if this is the case then the $IC_{50}$ value at high serum albumin will be higher than the $IC_{50}$ value at low albumin. An increased $IC_{50}$ value at high serum albumin represents a reduced binding to the GLP-1 receptor caused by serum albumin binding competing with the binding to the GLP-1 receptor.

In a particular embodiment, the derivatives of the invention bind very well to the GLP-1 receptor at a low albumin concentration, but they also bind very well at a high albumin concentration.

As an example, in a particular embodiment, the GLP-1 receptor binding affinity ($IC_{50}$) of the derivatives of the invention in the presence of a low concentration of HSA (low albumin) is at 5.0 nM or below.

Pharmacokinetics Profile

According to the third functional aspect, the derivatives of the invention have improved pharmacokinetic properties such as increased terminal half-life, and/or decreased clearance.

Increasing terminal half-life and/or decreasing of the clearance means that the compound in question is eliminated slower from the body. For the derivatives of the invention this entails an extended duration of pharmacological effect.

The pharmacokinetic properties of the derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

In such studies, animals are typically administered with a single dose of the drug, either intravenously (i.v.), subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half Life In Vivo in Minipigs

According to the third functional aspect, the derivatives of the invention have improved pharmacokinetic properties.

In a particular embodiment, the pharmacokinetic properties may be determined as terminal half-life ($T_{1/2}$) in vivo in minipigs after i.v. administration, e.g. as described in Example 31 herein.

In a particular embodiment the derivatives of the invention have an excellent terminal half-life in minipigs which makes them suitable for once-monthly administration. In a particular embodiment, the terminal half-life of the derivatives of the invention in minipigs after i.v. administration is at least 90 hours.

Additional particular embodiments of the derivatives of the invention are described in the section headed "Particular embodiments" before the experimental section.

Production Processes

The production of peptides like GLP-1(7-37) and GLP-1 analogues is well known in the art.

The GLP-1 like peptide moiety of the derivatives of the invention (or fragments thereof) may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

The invention also relates to pharmaceutical compositions comprising a derivative of the invention or a pharmaceutically acceptable salt, amide, or ester thereof, and a pharmaceutically acceptable excipient. Such compositions may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19$^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml. A pharmaceutical composition may comprise an isotonic agent. The isotonic agent may e.g. be selected from a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants. The term "surfactant" refers to any molecules or ions that are comprised of a water-soluble (hydrophilic) part, and a fat-soluble (lipophilic) part. The surfactant may e.g. be selected from anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

As stated above the present invention also relates to pharmaceutical compositions comprising a derivative of the invention or a pharmaceutically acceptable salt, amide, or ester thereof, and a pharmaceutically acceptable excipient.

In a particular embodiment, the excipient comprises a phosphate buffer and an isotonic agent.

In another particular embodiment, the excipient comprises a phosphate buffer and propylene glycol ad isotoni.

In a still further particular embodiment the invention relates to a single dose pharmaceutical composition for s.c. injection which comprises (i) a GLP-1 derivative of the invention or a pharmaceutically acceptable salt, amide, or ester thereof, in a suitable concentration, (ii) an 8 mM phosphate buffer (such as 1.42 mg/mL Disodium Phosphate Dihydrate), (iii) propylene glycol ad isotoni, and (iv) which has a pH of 7.4.

The term "suitable concentration" refers to a pharmaceutically relevant concentration, which may be determined as is known in the art.

Non-limiting examples of suitable concentrations correspond to the administered doses mentioned below, when contained in 1 mL of the composition (i.e., e.g. a suitable concentration may be from 0.1 mg/mL to 100 mg/mL of the composition).

In a particular embodiment, the suitable concentration is 3 mg/mL.

In another particular embodiment, the suitable concentration is 30 mg/mL.

In still further particular embodiments the GLP-1 derivative is (a) the compound of Example 1, (b) the compound of Example 2, (c) the compound of Example 3, (d) the compound of Example 5, or a pharmaceutically acceptable salt, amide, or ester of any of (a)-(d).

Still further, a pharmaceutical composition may be formulated as is known in the art of oral formulations of insulinotropic compounds, e.g. using any one or more of the formulations described in WO 2008/145728.

An administered dose may contain from 0.1 mg-100 mg of the derivative, from 1-100 mg of the derivative, or from 1-50 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. A composition may be an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon agonists, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, fibroblast growth factor 21 (FGF-21), galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention, for use as a medicament.

In particular embodiments, the derivative of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In a particular embodiment the indication is selected from the group consisting of (i)-(xiv), such as indications (i)-(viii), (x)-(xiii), and/or (xiv), and relates in one way or the other to diabetes.

In another particular embodiment, the indication is selected from the group consisting of (i)-(iii) and (v)-(viii), such as indications (i), (ii), and/or (iii); or indication (v), indication (vi), indication (vii), and/or indication (viii).

In a still further particular embodiment, the indication is (i). In a further particular embodiment the indication is (v). In a still further particular embodiment the indication is (viii).

The following indications are particularly preferred: Type 2 diabetes, and/or obesity.

Particular Embodiments

The following are particular embodiments of the invention:

1. A derivative of a GLP-1 like peptide, wherein the GLP-1 like peptide comprises a peptide of formula I:

$Xaa_7\text{-}Xaa_8\text{-}Glu\text{-}Gly\text{-}Thr\text{-}Xaa_{12}\text{-}Thr\text{-}Ser\text{-}Asp\text{-}Xaa_{16}\text{-}Ser\text{-}Xaa_{18}\text{-}Xaa_{19}\text{-}Xaa_{20}\text{-}Glu\text{-}Xaa_{22}\text{-}Xaa_{23}\text{-}Ala\text{-}Xaa_{25}\text{-}Xaa_{26}\text{-}Xaa_{27}\text{-}Phe\text{-}Ile\text{-}Xaa_{30}\text{-}Xaa_{31}\text{-}Leu\text{-}Xaa_{33}\text{-}Xaa_{34}\text{-}Xaa_{35}\text{-}Xaa_{36}\text{-}Xaa_{37}\text{-}Xaa_{38}\text{-}Xaa_{39}\text{-}Xaa_{40}\text{-}Xaa_{41}\text{-}Xaa_{42}$, Formula I:

wherein $Xaa_7$ is L-histidine, (S)-2-Hydroxy-3-(1H-imidazol-4-yl)-propionic acid, D-histidine, desamino-histidine, homohistidine, $N^\alpha$-acetyl-histidine, $N^\alpha$-formyl-histidine, $N^\alpha$-methyl-histidine, 3-pyridylalanine, 2-pyridylalanine, or 4-pyridylalanine;

$Xaa_8$ is Ala, Gly, Ser, Aib, (1-aminocyclopropyl) carboxylic acid, or (1-aminocyclobutyl) carboxylic acid;

$Xaa_{12}$ is Phe or Leu;
$Xaa_{16}$ is Val or Leu;
$Xaa_{18}$ is Ser, Arg, Lys, Val, or Leu;
$Xaa_{19}$ is Tyr or Gln;
$Xaa_{20}$ is Leu or Met;
$Xaa_{22}$ is Gly or Glu;
$Xaa_{23}$ is Gln, Glu, Lys, or Arg;
$Xaa_{25}$ is Ala or Val;
$Xaa_{26}$ is Arg or Lys;
$Xaa_{27}$ is Glu, Lys, or Leu;
$Xaa_{30}$ is Ala, Glu, or Arg;
$Xaa_{31}$ is Trp, Lys, or His;
$Xaa_{33}$ is Val, Lys, or Arg;
$Xaa_{34}$ is Lys, Arg, His, Asn, or Gln;
$Xaa_{35}$ is Gly or Ala;
$Xaa_{36}$ is Arg, Lys, or Gly;
$Xaa_{37}$ is Gly or Pro;
$Xaa_{38}$ is Ser, Gly, Ala, Glu, Pro, or Lys;
$Xaa_{39}$ is Ser, Gly, Ala, Glu, or Pro;
$Xaa_{40}$ is Ser, Gly, Ala, Glu, or Pro;
$Xaa_{41}$ is Ser, Gly, Ala, Glu, or Pro; and
$Xaa_{42}$ is Lys;

with the proviso that at least one of $Xaa_{18}$, $Xaa_{23}$, $Xaa_{27}$, $Xaa_{31}$, $Xaa_{36}$, or $Xaa_{38}$ is Lys;

wherein

Lys at $Xaa_{42}$ is a first K residue, and a Lys at one of $Xaa_{18}$, $Xaa_{23}$, $Xaa_{27}$, $Xaa_{31}$, $Xaa_{36}$, or $Xaa_{38}$ is a second K residue;

which derivative comprises a first and a second protracting moiety connected to said first and second K residue, respectively, wherein the first and the second protracting moiety is selected from Chem. 1, Chem. 1a, and Chem. 1b:

$HOOC\text{---}(CH_2)_{18}\text{---}CO\text{---}*$, Chem. 1:

$HOOC\text{---}(CH_2)_{17}\text{---}CO\text{---}*$, or Chem. 1a:

$HOOC\text{---}(CH_2)_{20}\text{---}CO\text{---}*$; Chem. 1b:

or a pharmaceutically acceptable salt, amide, or ester thereof.

2. The derivative of embodiment 1, wherein the GLP-1 like peptide comprises at least two Lys residues.
3. The derivative of any of embodiments 1-2, wherein the GLP-1 like peptide comprises two Lys residues.
4. The derivative of any of embodiments 1-3, wherein the GLP-1 like peptide has two Lys residues.
5. The derivative of any of embodiments 1-4, wherein the GLP-1 like peptide has only two Lys residues.
6. The derivative of any of embodiments 15, wherein one of $Xaa_{18}$, $Xaa_{23}$, $Xaa_{27}$, $Xaa_{31}$, $Xaa_{36}$, or $Xaa_{38}$ is Lys.
7. The derivative of any of embodiments 1-6, wherein only one of $Xaa_{18}$, $Xaa_{23}$, $Xaa_{27}$, $Xaa_{31}$, $Xaa_{36}$, or $Xaa_{38}$ is Lys.
8. The derivative of any of embodiments 1-7, wherein a Lys at $Xaa_{18}$ is the second K residue.
9. The derivative of any of embodiments 1-8, wherein a Lys at $Xaa_{23}$ is the second K residue.
10. The derivative of any of embodiments 1-9, wherein a Lys at $Xaa_{27}$ is the second K residue.
11. The derivative of any of embodiments 1-10, wherein a Lys at $Xaa_{31}$ is the second K residue.
12. The derivative of any of embodiments 1-11, wherein a Lys at $Xaa_{36}$ is the second K residue.
13. The derivative of any of embodiments 1-12, wherein a Lys at $Xaa_{38}$ is the second K residue.
14. The derivative of any of embodiments 1-4, wherein $Xaa_7$ is His.
15. The derivative of any of embodiments 1-14, wherein $Xaa_7$ is desamino-histidine.
16. The derivative of any of embodiments 1-15, wherein $Xaa_8$ is Aib.
17. The derivative of any of embodiments 1-16, wherein $Xaa_{12}$ is Phe.
18. The derivative of any of embodiments 1-17, wherein $Xaa_{16}$ is Val.
19. The derivative of any of embodiments 1-18, wherein $Xaa_{18}$ is Ser or Lys.
20. The derivative of any of embodiments 1-19, wherein $Xaa_{18}$ is Ser.
21. The derivative of any of embodiments 1-19, wherein $Xaa_{18}$ is Lys.
22. The derivative of any of embodiments 1-21, wherein $Xaa_{19}$ is Tyr.
23. The derivative of any of embodiments 1-22, wherein $Xaa_{20}$ is Leu.
24. The derivative of any of embodiments 1-23, wherein $Xaa_{22}$ is Glu.
25. The derivative of any of embodiments 1-24, wherein $Xaa_{23}$ is Gln or Lys.
26. The derivative of any of embodiments 1-25, wherein $Xaa_{23}$ is Gln.
27. The derivative of any of embodiments 1-25, wherein $Xaa_{23}$ is Lys.
28. The derivative of any of embodiments 1-27, wherein $Xaa_{25}$ is Ala.
29. The derivative of any of embodiments 1-28, wherein $Xaa_{26}$ is Arg.
30. The derivative of any of embodiments 1-29, wherein $Xaa_{27}$ is Glu or Lys.
31. The derivative of any of embodiments 1-30, wherein $Xaa_{27}$ is Glu.
32. The derivative of any of embodiments 1-30, wherein $Xaa_{27}$ is Lys.
33. The derivative of any of embodiments 1-32, wherein $Xaa_{30}$ is Ala.
34. The derivative of any of embodiments 1-33, wherein $Xaa_{31}$ is Trp or Lys.
35. The derivative of any of embodiments 1-34, wherein $Xaa_{31}$ is Lys.
36. The derivative of any of embodiments 1-34, wherein $Xaa_{31}$ is Trp.
37. The derivative of any of embodiments 1-36, wherein $Xaa_{33}$ is Val.
38. The derivative of any of embodiments 1-37, wherein $Xaa_{34}$ is Arg.
39. The derivative of any of embodiments 1-38, wherein $Xaa_{35}$ is Gly.

40. The derivative of any of embodiments 1-39, wherein $Xaa_{36}$ is Arg or Lys.
41. The derivative of any of embodiments 1-40, wherein $Xaa_{36}$ is Arg.
42. The derivative of any of embodiments 1-40, wherein $Xaa_{36}$ is Lys.
43. The derivative of any of embodiments 1-42, wherein $Xaa_{37}$ is Gly.
44. The derivative of any of embodiments 1-43, wherein $Xaa_{38}$ is Gly, Ala, Glu, Pro, or Lys.
45. The derivative of any of embodiments 1-44, wherein $Xaa_{38}$ is Gly.
46. The derivative of any of embodiments 1-44, wherein $Xaa_{38}$ is Ala.
47. The derivative of any of embodiments 1-44, wherein $Xaa_{38}$ is Glu.
48. The derivative of any of embodiments 1-44, wherein $Xaa_{38}$ is Pro.
49. The derivative of any of embodiments 1-44, wherein $Xaa_{38}$ is Lys.
50. The derivative of any of embodiments 1-49, wherein $Xaa_{39}$ is Ser, Gly, Ala, Glu, or Pro.
51. The derivative of any of embodiments 1-50, wherein $Xaa_{39}$ is Ser.
52. The derivative of any of embodiments 1-50, wherein $Xaa_{39}$ is Gly.
53. The derivative of any of embodiments 1-50, wherein $Xaa_{39}$ is Ala.
54. The derivative of any of embodiments 1-50, wherein $Xaa_{39}$ is Glu.
55. The derivative of any of embodiments 1-50, wherein $Xaa_{39}$ is Pro.
56. The derivative of any of embodiments 1-55, wherein $Xaa_{40}$ is Ser, Gly, Ala, Glu, or Pro.
57. The derivative of any of embodiments 1-56, wherein $Xaa_{40}$ is Ser.
58. The derivative of any of embodiments 1-56, wherein $Xaa_{40}$ is Gly.
59. The derivative of any of embodiments 1-56, wherein $Xaa_{40}$ is Ala.
60. The derivative of any of embodiments 1-56, wherein $Xaa_{40}$ is Glu.
62. The derivative of any of embodiments 1-56, wherein $Xaa_{40}$ is Pro.
63. The derivative of any of embodiments 1-62, wherein $Xaa_{41}$ is Ser, Gly, Ala, Glu, or Pro.
64. The derivative of any of embodiments 1-63, wherein $Xaa_{41}$ is Ser.
65. The derivative of any of embodiments 1-63, wherein $Xaa_{41}$ is Gly.
66. The derivative of any of embodiments 1-63, wherein $Xaa_{41}$ is Ala.
67. The derivative of any of embodiments 1-63, wherein $Xaa_{41}$ is Glu.
68. The derivative of any of embodiments 1-63, wherein $Xaa_{41}$ is Pro.
69. The derivative of any of embodiments 1-68, wherein the GLP-1 like peptide is a peptide of Formula I.
70. The derivative of any of embodiments 1-69, wherein in Formula I $Xaa_7$ is L-histidine, (S)-2-Hydroxy-3-(1H-imidazol-4-yl)-propionic acid, D-histidine, desamino-histidine, $N^\alpha$-acetyl-histidine, $N^\alpha$-formyl-histidine, $N^\alpha$-methyl-histidine; $Xaa_8$ is Ala, Gly, Ser, Aib, (1-aminocyclopropyl) carboxylic acid, or (1-aminocyclobutyl)carboxylic acid; $Xaa_{12}$ is Phe; $Xaa_{16}$ is Val or Leu; $Xaa_{18}$ is Ser, Arg, or Lys; $Xaa_{19}$ is Tyr or Gln; $Xaa_{20}$ is Leu or Met; $Xaa_{22}$ is Gly or Glu; $Xaa_{23}$ is Gln, Glu, Lys, or Arg; $Xaa_{25}$ is Ala or Val; $Xaa_{26}$ is Arg or Lys; $Xaa_{27}$ is Glu, Lys, or Leu; $Xaa_{30}$ is Ala or Glu; $Xaa_{31}$ is Trp, Lys, or His; $Xaa_{33}$ is Val, Lys, or Arg; $Xaa_{34}$ is Lys, Arg, or Asn; $Xaa_{35}$ is Gly; $Xaa_{36}$ is Arg, Lys, or Gly; $Xaa_{37}$ is Gly or Pro; $Xaa_{38}$ is Gly, Ala, Glu, Pro, or Lys; $Xaa_{39}$ is Ser, Gly, Ala, Glu, or Pro; $Xaa_{40}$ is Ser, Gly, Ala, Glu, or Pro; $Xaa_{41}$ is Ser, Gly, Ala, Glu, or Pro; and $Xaa_{42}$ is Lys.
71. The derivative of any of embodiments 1-70, wherein in Formula I $Xaa_7$ is L-histidine, desamino-histidine, $Xaa_8$ is Aib; $Xaa_{12}$ is Phe; $Xaa_{16}$ is Val; $Xaa_{18}$ is Ser or Lys; $Xaa_{19}$ is Tyr; $Xaa_{20}$ is Leu; $Xaa_{22}$ is Glu; $Xaa_{23}$ is Gln or Lys; $Xaa_{25}$ is Ala; $Xaa_{26}$ is Arg; $Xaa_{27}$ is Glu or Lys; $Xaa_{30}$ is Ala; $Xaa_{31}$ is Trp or Lys; $Xaa_{33}$ is Val; $Xaa_{34}$ is Arg; $Xaa_{35}$ is Gly; $Xaa_{36}$ is Arg or Lys; $Xaa_{37}$ is Gly; $Xaa_{38}$ is Gly, Ala, Glu, Pro, or Lys; $Xaa_{39}$ is Ser, Gly, Ala, Glu, or Pro; $Xaa_{40}$ is Ser, Gly, Ala, Glu, or Pro; $Xaa_{41}$ is Ser, Gly, Ala, Glu, or Pro; and $Xaa_{42}$ is Lys.
72. The derivative of any of embodiments 1-71, wherein the GLP-1 like peptide has a maximum of 12 amino acid changes, when compared with GLP-1(7-37) (SEQ ID NO: 1).
73. The derivative of any of embodiments 1-72, wherein the GLP-1 like peptide has a maximum of 11 amino acid changes, when compared with GLP-1(7-37) (SEQ ID NO: 1).
74. The derivative of any of embodiments 1-73, wherein the GLP-1 like peptide has a maximum of 10 amino acid changes, when compared with GLP-1(7-37) (SEQ ID NO: 1).
75. The derivative of any of embodiments 1-74, wherein the GLP-1 like peptide has a maximum of 9 amino acid changes, when compared with GLP-1(7-37) (SEQ ID NO: 1).
76. The derivative of any of embodiments 1-75, wherein the GLP-1 like peptide has a maximum of 8 amino acid changes, when compared with GLP-1(7-37) (SEQ ID NO: 1).
77. The derivative of any of embodiments 1-76, wherein the GLP-1 like peptide has a maximum of 7 amino acid changes, when compared with GLP-1(7-37) (SEQ ID NO: 1).
78. The derivative of any of embodiments 1-77, wherein the GLP-1 like peptide has a maximum of 6 amino acid changes, when compared with GLP-1(7-37) (SEQ ID NO: 1).
79. The derivative of any of embodiments 1-78, wherein the GLP-1 like peptide has a maximum of 5 amino acid changes, when compared with GLP-1(7-37) (SEQ ID NO: 1).
80. The derivative of any of embodiments 1-79, wherein the GLP-1 like peptide has a minimum of 5 amino acid changes, when compared with GLP-1(7-37) (SEQ ID NO: 1).
81. The derivative of any of embodiments 1-80, wherein the GLP-1 like peptide has a minimum of 6 amino acid changes, when compared with GLP-1(7-37) (SEQ ID NO: 1).
82. The derivative of any of embodiments 1-81, wherein the GLP-1 like peptide has a minimum of 7 amino acid changes, when compared with GLP-1(7-37) (SEQ ID NO: 1).
83. The derivative of any of embodiments 1-82, wherein the GLP-1 like peptide has a minimum of 8 amino acid changes, when compared with GLP-1(7-37) (SEQ ID NO: 1).
84. The derivative of any of embodiments 1-83, wherein the GLP-1 like peptide has a minimum of 9 amino acid changes, when compared with GLP-1(7-37) (SEQ ID NO: 1).
85. The derivative of any of embodiments 1-84, wherein the GLP-1 like peptide has a minimum of 10 amino acid changes, when compared with GLP-1(7-37) (SEQ ID NO: 1).
86. The derivative of any of embodiments 1-85, wherein the GLP-1 like peptide has 5 amino acid changes, when compared with GLP-1(7-37) (SEQ ID NO: 1).

87. The derivative of any of embodiments 1-85, wherein the GLP-1 like peptide has 6 amino acid changes, when compared with GLP-1(7-37) (SEQ ID NO: 1).
88. The derivative of any of embodiments 1-85, wherein the GLP-1 like peptide has 7 amino acid changes, when compared with GLP-1(7-37) (SEQ ID NO: 1).
89. The derivative of any of embodiments 1-85, wherein the GLP-1 like peptide has 8 amino acid changes, when compared with GLP-1(7-37) (SEQ ID NO: 1).
90. The derivative of any of embodiments 1-85, wherein the GLP-1 like peptide has 9 amino acid changes, when compared with GLP-1(7-37) (SEQ ID NO: 1).
91. The derivative of any of embodiments 1-85, wherein the GLP-1 like peptide has 10 amino acid changes, when compared with GLP-1(7-37) (SEQ ID NO: 1).
92. The derivative of any of embodiments 1-91, wherein the GLP-1 like peptide is selected from the following analogues of GLP-1 (7-37) (SEQ ID NO: 1): i) (8Aib, 22E, 26R, 27K, 34R, 38G, 39G, 40G, 41S, 42K) (SEQ ID NO: 2); ii) (8Aib, 22E, 26R, 31K, 34R, 38G, 39G, 40G, 41S, 42K) (SEQ ID NO: 3); iii) (8Aib, 22E, 26R, 34R, 38K, 39G, 40G, 41S, 42K) (SEQ ID NO: 4); iv (8Aib, 22E, 23K, 26R, 34R, 38G, 39G, 40G, 41S, 42K) (SEQ ID NO: 5); v) (8Aib, 22E, 26R, 34R, 36K, 38G, 39G, 40G, 41S, 42K) (SEQ ID NO: 6); vi) (8Aib, 18K, 22E, 26R, 34R, 38G, 39G, 40G, 41S, 42K) (SEQ ID NO: 7); vii) (7Imp, 8Aib, 22E, 26R, 34R, 38K, 39G, 40G, 41S, 42K) (SEQ ID NO: 8); iix) (8Aib, 22E, 26R, 34R, 36K, 38A, 39E, 40S, 41P, 42K) (SEQ ID NO: 9); ix) (8Aib, 22E, 26R, 34R, 36K, 38E, 39G, 40P, 41A, 42K) (SEQ ID NO: 10); x) (8Aib, 22E, 26R, 34R, 36K, 38P, 39A, 40S, 41E, 42K) (SEQ ID NO: 11); xi) (8Aib, 22E, 26R, 34R, 38K, 39P, 40E, 41G, 42K) (SEQ ID NO: 12); xii) (8Aib, 22E, 26R, 34R, 38K, 39S, 40A, 41E, 42K) (SEQ ID NO: 13); and xiii) (8Aib, 22E, 26R, 34R, 38K, 39S, 40P, 41E, 42K) (SEQ ID NO: 14).
93 The derivative of any of embodiments 1-92, wherein each of the first and the second protracting moiety is Chem. 1.
94. The derivative of any of embodiments 1-92, wherein each of the first and the second protracting moiety is Chem. 1a.
95. The derivative of any of embodiments 1-92, wherein each of the first and the second protracting moiety is Chem. 1b.
96. The derivative of any of embodiments 1-95, wherein each of the first and the second protracting moiety is attached to the first and the second K residue, respectively, optionally via a first and a second linker, respectively.
97. The derivative of embodiment 96, wherein each of the first and second protracting moiety is attached to the first and the second K residue, respectively, via a first and a second linker, respectively.
98. The derivative of any of embodiments 96-97, wherein the first and the second linker each incorporates an *—NH or *—N group, and a *—CO group.
99. The derivative of any of embodiments 96-98, wherein each of the first and the second linker comprises an element_1 of formula Chem. 2:

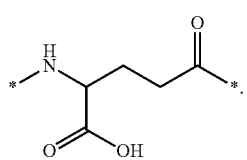

Chem. 2

100. The derivative of any of embodiments 96-99, wherein each of the first and the second linker incorporates one element_1 of formula Chem. 2.
101. The derivative of any of embodiments 99-100, wherein Chem. 2 represents a gGlu residue.
102. The derivative of any of embodiments 99-101, wherein element_1 is an L-gGlu residue.
103. The derivative of any of embodiments 96-102, wherein each of the first and the second linker comprises an element_2 of formula Chem. 3:

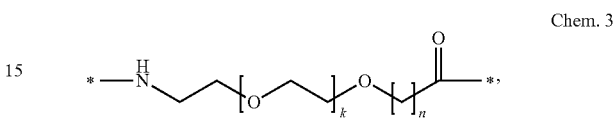

Chem. 3 wherein k is an integer in the range of 1-5, and n is an integer in the range of 1-5.
104. The derivative of embodiment 103, wherein each of the first and the second linker comprises at least one element_2 of formula Chem. 3.
105. The derivative of any of embodiments 103-104, wherein each of the first and the second linker comprises at least two elements_2 of formula Chem. 3.
106. The derivative of any of embodiments 103-105, wherein each of the first and the second linker comprises two elements_2 of formula Chem. 3.
107. The derivative of any of embodiments 103-106, wherein each of the first and the second linker incorporates two elements_2 of formula Chem. 3.
108. The derivative of any of embodiments 103-107, wherein each of the first and the second linker comprises four elements_2 of formula Chem. 3.
109. The derivative of any of embodiments 103-108, wherein each of the first and the second linker incorporates four elements_2 of formula Chem. 3.
110. The derivative of any of embodiments 103-109, wherein each of the first and the second linker comprises five elements_2 of formula Chem. 3.
111. The derivative of any of embodiments 103-110, wherein each of the first and the second linker incorporates five elements_2 of formula Chem. 3.
112. The derivative of any of embodiments 103-111, wherein each of the first and the second linker comprises six elements_2 of formula Chem. 3.
113. The derivative of any of embodiments 103-112, wherein each of the first and the second linker incorporates six elements_2 of formula Chem. 3.
114. The derivative of any of embodiments 103-113, wherein k=1 and n=1.
115. The derivative of any of embodiments 103-114, wherein Chem. 3 represents OEG.
116. The derivative of any of embodiments 103-104, wherein each of the first and the second linker comprises one element_2 of formula Chem. 3.
117. The derivative of any of embodiments 103-104 and 116, wherein each of the first and the second linker incorporates one element_2 of formula Chem. 3.
118. The derivative of any of embodiments 116-117, wherein k=3 and n=2.
119. The derivative of any of embodiments 116-118, wherein Chem. 3 represents dPEG4.
120. The derivative of any of embodiments 96-119, wherein each of the first and the second linker comprises an element_3 of formula Chem. 4:

Chem. 4

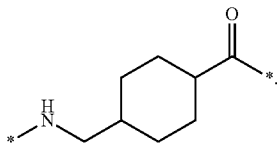

121. The derivative of any of embodiments 96-120, wherein each of the first and second linker each incorporates one element_3 of formula Chem. 4.
122. The derivative of any of embodiments 120-121, wherein Chem. 4 represents Trx.
123. The derivative of any of embodiments 96-122, wherein each of the first and the second linker comprises an element_4 of formula Chem. 5:

*—NH—(CH$_2$)$_q$—CH[(CH$_2$)$_w$—NH$_2$]—CO—*,  Chem. 5:

wherein q is an integer in the range of 0-5, and w is an integer in the range of 0-5, with the provisos that when w is 0 q is an integer in the range of 1-5, and when q is 0 w is an integer in the range of 1-5.
124. The derivative of embodiment 123, wherein each of the first and the second linker comprises at least one element_4 of formula Chem. 5.
125. The derivative of any of embodiments 123-124, wherein each of the first and the second linker comprises at least two elements_4 of formula Chem. 5.
126. The derivative of any of embodiments 123-125, wherein each of the first and the second linker comprises two elements_4 of formula Chem. 5.
127. The derivative of any of embodiments 123-126, wherein each of the first and the second linker incorporates two elements_4 of formula Chem. 5.
128. The derivative of any of embodiments 123-127, wherein q is 4 and w is 0.
129. The derivative of any of embodiments 123-127, wherein w is 4 and q is 0.
130. The derivative of any of embodiments 123-129, wherein Chem. 5 represents an eps-Lys residue.
131. The derivative of any of embodiments 123-130, wherein element_4 is an L-eps-Lys residue.
132. The derivative of any of embodiments 96-131, wherein each of the first and the second linker comprises an element_5 of formula Chem. 6:

Chem. 6

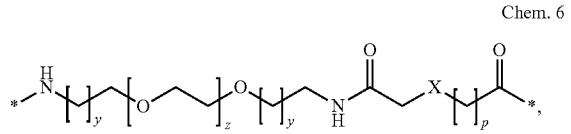

wherein y is 1 or 2, z is 1 or 2, p is 0 or 1, and X designates a carbon atom or an oxygen atom.

133. The derivative of embodiment 132, wherein each of the first and the second linker incorporates one element_5 of formula Chem. 6.
134. The derivative of any of embodiments 132-133, wherein y is 2, z is 2, p is 1, and X represents an oxygen atom.
135. The derivative of embodiment 134, wherein Chem. 6 represents a TotaGlyc residue or formula Chem. 7:

Chem. 7

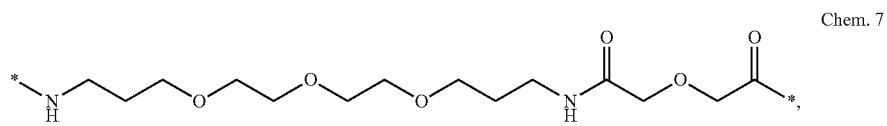

136. The derivative of any of embodiments 132-133, wherein y is 2, z is 2, p is 0, and X represents a carbon atom.
137. The derivative of embodiment 136, wherein Chem. 6 represents a TtdSuc.residue of formula Chem. 8:

Chem. 8

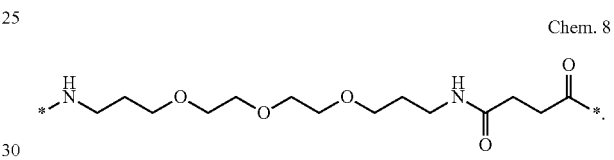

138. The derivative of any of embodiments 132-133, wherein y is 1, z is 1, p is 0, and X represents a carbon atom.
139. The derivative of embodiment 138, wherein Chem. 6 represents a DooaSuc residue of formula Chem. 9:

Chem. 9

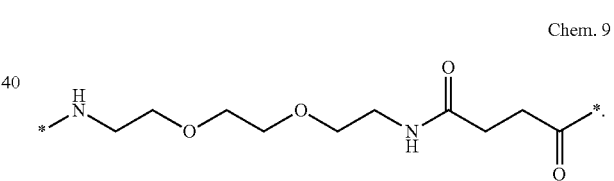

140. The derivative of any of embodiments 96-139, wherein each of the first and the second linker comprises an element_6 of formula Chem. 10:

Chem. 10

141. The derivative of any of embodiments 96-140, wherein each of the first and the second linker incorporates one element_6 of formula Chem. 10.
142. The derivative of any of embodiments 140-141, wherein Chem. 10 represents an Inp residue.
144. The derivative of any of embodiments 1-142 which comprises at least one of the linker elements element_1, element_2, element_3, element_4, element_5, and element_6.

145. The derivative of embodiment 144, wherein each of the linker elements is defined as in any of embodiments 99-142.

146. The derivative of any of embodiments 1-145, wherein each of the first and the second linker consists of one element_3 of formula Chem. 4, one element_1 of formula Chem. 2, and two elements_2 of formula Chem. 3 wherein k=1 and n=1, interconnected via amide bonds and in the sequence indicated.

147. The derivative of any of embodiments 1-145, wherein each of the first and the second linker consists of one element_3 of formula Chem. 4, one element_1 of formula Chem. 2, and four elements_2 of formula Chem. 3 wherein k=1 and n=1, interconnected via amide bonds and in the sequence indicated.

148. The derivative of any of embodiments 1-145, wherein each of the first and the second linker consists of one element_3 of formula Chem. 4, one element_1 of formula Chem. 2, and six elements_2 of formula Chem. 3 wherein k=1 and n=1, interconnected via amide bonds and in the sequence indicated.

149. The derivative of any of embodiments 1-145, wherein each of the first and the second linker consists of one element_3 of formula Chem. 4, one element_1 of formula Chem. 2, and one element_2 of formula Chem. 3 wherein k=3 and n=2, interconnected via amide bonds and in the sequence indicated.

150. The derivative of any of embodiments 1-145, wherein each of the first and the second linker consists of one element_3 of formula Chem. 4, one element_1 of formula Chem. 2, and two elements_4 of formula Chem. 5 wherein q=4 and w=0 (or w=4 and q=0), interconnected via amide bonds and in the sequence indicated.

151. The derivative of any of embodiments 1-145, wherein each of the first and the second linker consists of one element_3 of formula Chem. 4, one element_1 of formula Chem. 2, and one element_5 of formula Chem. 9, interconnected via amide bonds and in the sequence indicated.

152. The derivative of any of embodiments 1-145, wherein each of the first and the second linker consists of one element_1 of formula Chem. 2 and two elements_4 of formula Chem. 5 wherein q=4 and w=0 (or w=4 and q=0), interconnected via amide bonds and in the sequence indicated.

153. The derivative of any of embodiments 1-145, wherein each of the first and the second linker consists of one element_1 of formula Chem. 2 and four elements_2 of formula Chem. 3 wherein k=1 and n=1, interconnected via amide bonds and in the sequence indicated.

154. The derivative of any of embodiments 1-145, wherein each of the first and the second linker consists of one element_1 of formula Chem. 2 and one element_5 of formula Chem. 7, interconnected via amide bonds and in the sequence indicated.

155. The derivative of any of embodiments 1-145, wherein each of the first and the second linker consists of two elements_4 of formula Chem. 5 and four elements_2 of formula Chem. 3 wherein k=1 and n=1, interconnected via amide bonds and in the sequence indicated.

156. The derivative of any of embodiments 1-145, wherein each of the first and the second linker consists of two elements_4 of formula Chem. 5 and five elements_2 of formula Chem. 3 wherein k=1 and n=1, interconnected via amide bonds and in the sequence indicated.

157. The derivative of any of embodiments 1-145, wherein each of the first and the second linker consists of two elements_4 of formula Chem. 5 and six elements_2 of formula Chem. 3 wherein k=1 and n=1, interconnected via amide bonds and in the sequence indicated.

158. The derivative of any of embodiments 1-145, wherein each of the first and the second linker consists of one element_6 of formula Chem. 10, one element_1 of formula Chem. 2, and one element_5 of formula Chem. 8, interconnected via amide bonds and in the sequence indicated.

159. The derivative of any of embodiments 1-158, wherein the CO—* group of each of the first and second protracting moieties, such as Chem. 1, Chem. 1a, or Chem. 1b, is attached to the epsilon amino group of the first and second K residue, respectively, optionally via a first and a second linker, respectively.

160. The derivative of any of embodiments 1-159, wherein the CO—* group of each of the first and second protracting moieties, such as Chem. 1, Chem. 1a, or Chem. 1b, is attached to the epsilon amino group of the first and second K residue, respectively, via a first and a second linker, respectively.

161. The derivative of any of embodiments 1-160, wherein each of the first and the second protracting moiety is attached to the epsilon amino group of the first and the second K-residue, respectively, under the formation of an amide bond, optionally via a first and a second linker, respectively, which is connected via amide bonds to the first and the second protracting moiety as well as to the first and the second K residue.

162. The derivative of any of embodiments 1-161, wherein each of the first and the second protracting moiety is attached to the epsilon amino group of the first and the second K-residue, respectively, under the formation of an amide bond, via a first and a second linker, respectively, which is connected via amide bonds to the first and the second protracting moiety as well as to the first and the second K residue.

163. The derivative of any of embodiments 1-162, wherein the CO—* group of each of the first and the second protracting moieties is attached to an *—NH or *—N group of a first and a second linker, respectively, and a *—CO group of each of the first and the second linker is attached to the epsilon amino group of the first and the second K-residue, respectively.

164. The derivative of any of embodiments 1-163, in the form of an acid or basic salt.

165. The derivative of any of embodiments 1-164 in the form of an acid salt.

166. The derivative of any of embodiments 1-165 in the form of an acetate salt.

167. The derivative of any of embodiments 1-163 in the form of a basic salt.

168. The derivative of any of embodiments 1-167 in the form of a sodium or potassium salt.

169. The derivative of any of embodiments 1-168 in the form of a sodium salt.

170. The derivative of any of embodiments 1-169 in the form of a potassium salt.

171. The derivative of any of embodiments 1-170 which is a GLP-1 receptor agonist.

172. The derivative of any of embodiments 1-171, which is a full GLP-1 receptor agonist.

173. The derivative of any of embodiments 1-172, which is biologically active in vitro.

174. The derivative of any of embodiments 1-173, which is potent in vitro.

175. The derivative of any of embodiments 1-174, which is capable of activating the human GLP-1 receptor.

176. The derivative of any of embodiments 1-175 which is capable of activating the human GLP-1 receptor in an assay with whole cells expressing the human GLP-1 receptor, wherein the assay is performed in the absence of HSA (0% HSA), and/or in the presence of HSA (1% HSA)), preferably in the absence of HSA.
177. The derivative of any of embodiments 1-176, where the response of the human GLP-1 receptor is measured in a reporter gene assay, such as the assay of Example 29.
178. The derivative of any of embodiments 1-177, wherein the biological activity, or potency, in vitro is determined essentially as described in Example 29.
179. The derivative of any of embodiments 1-178, which has an in vitro potency corresponding to an $EC_{50}$ of 400 pM or below.
180. The derivative of any of embodiments 1-179, which has an in vitro potency corresponding to an $EC_{50}$ of 300 pM or below.
181. The derivative of any of embodiments 1-180, which has an in vitro potency corresponding to an $EC_{50}$ of 100 pM or below.
182. The derivative of any of embodiments 1-181, which has an in vitro potency corresponding to an $EC_{50}$ of 75 pM or below.
183. The derivative of any of embodiments 1-182, which has an in vitro potency corresponding to an $EC_{50}$ of 55 pM or below.
184. The derivative of any of embodiments 1-183, which has an in vitro potency corresponding to an $EC_{50}$ of 40 pM or below.
185. The derivative of any of embodiments 1-184, which has an in vitro potency corresponding to an $EC_{50}$ of 25 pM or below.
186. The derivative of any of embodiments 1-183, which has an in vitro potency corresponding to an $EC_{50}$ of 15 pM or below.
187. The derivative of any of embodiments 1-183, which has an in vitro potency corresponding to an $EC_{50}$ of 10 pM or below.
188. The derivative of any of embodiments 179-187, wherein the $EC_{50}$ is determined essentially as described in Example 29.
189. The derivative of any of embodiments 1-188, which has an in vitro potency corresponding to an $EC_{50}$ of less than 50 times the $EC_{50}$ of semaglutide, wherein the $EC_{50}$ of semaglutide is determined in the same way as the $EC_{50}$ of the derivative.
190. The derivative of any of embodiments 1-189, which has an in vitro potency corresponding to an $EC_{50}$ of less than 40 times the $EC_{50}$ of semaglutide, wherein the $EC_{50}$ of semaglutide is determined in the same way as the $EC_{50}$ of the derivative.
191. The derivative of any of embodiments 1-190, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.
192. The derivative of any of embodiments 1-191, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.
193. The derivative of any of embodiments 1-192, which has an in vitro potency corresponding to an $EC_{50}$ of less than 8 times the $EC_{50}$ of semaglutide, wherein the $EC_{50}$ of semaglutide is determined in the same way as the $EC_{50}$ of the derivative.
194. The derivative of any of embodiments 1-193, which has an in vitro potency corresponding to an $EC_{50}$ of less than 5 times the $EC_{50}$ of semaglutide, wherein the $EC_{50}$ of semaglutide is determined in the same way as the $EC_{50}$ of the derivative.
195. The derivative of any of embodiments 1-194, which has an in vitro potency corresponding to an $EC_{50}$ of less than 3.5 times the $EC_{50}$ of semaglutide, wherein the $EC_{50}$ of semaglutide is determined in the same way as the $EC_{50}$ of the derivative.
196. The derivative of any of embodiments 1-195, which has an in vitro potency corresponding to an $EC_{50}$ of less than 2 times the $EC_{50}$ of semaglutide, wherein the $EC_{50}$ of semaglutide is determined in the same way as the $EC_{50}$ of the derivative.
197. The derivative of any of embodiments 189-196, wherein the $EC_{50}$ is determined essentially as described in Example 29.
198. The derivative of any of embodiments 1-197, which is capable of binding to the GLP-1 receptor.
199. The derivative of any of embodiments 1-198, which is capable of binding to the GLP-1 receptor at a low concentration of HSA (max. 0.001% final assay concentration).
200. The derivative of any of embodiments 1-199, which is capable of binding to the GLP-1 receptor at a high concentration of HSA (2.0% final assay concentration).
201. The derivative of any of embodiments 1-200, wherein the binding to the human GLP-1 receptor is measured in a competitive binding assay, such as the assay of Example 30.
202. The derivative of any of embodiments 1-201, wherein the binding to the human GLP-1 receptor in vitro is determined essentially as described in Example 30.
203. The derivative of any of embodiments 1-202, which at a low concentration of HSA is capable of binding to the human GLP-1 receptor with an $IC_{50}$ of 5.0 nM or below.
204. The derivative of any of embodiments 1-203, which at a low concentration of HSA is capable of binding to the human GLP-1 receptor with an $IC_{50}$ of 4.0 nM or below.
205. The derivative of any of embodiments 1-204, which at a low concentration of HSA is capable of binding to the human GLP-1 receptor with an $IC_{50}$ of 3.0 nM or below.
206. The derivative of any of embodiments 1-205, which at a low concentration of HSA is capable of binding to the human GLP-1 receptor with an $IC_{50}$ of 2.0 nM or below.
207. The derivative of any of embodiments 1-206, which at a low concentration of HSA is capable of binding to the human GLP-1 receptor with an $IC_{50}$ of 1.0 nM or below.
208. The derivative of any of embodiments 1-207, which at a low concentration of HSA is capable of binding to the human GLP-1 receptor with an $IC_{50}$ of 0.8 nM or below.
209. The derivative of any of embodiments 203-208, wherein the $IC_{50}$ is determined essentially as described in Example 30, in a reaction with max. 0.001% HSA (final assay concentration).
210. The derivative of any of embodiments 1-209, which at a low concentration of HSA is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.
211. The derivative of any of embodiments 1-210, which at a low concentration of HSA is capable of binding to the human GLP-1 receptor with an $IC_{50}$ of less than 6 times the $IC_{50}$ of semaglutide, wherein the $IC_{50}$ of semaglutide is determined in the same way as the $IC_{50}$ of the derivative.
212. The derivative of any of embodiments 1-211, which at a low concentration of HSA is capable of binding to the human GLP-1 receptor with an $IC_{50}$ of less than 4.5 times the IC$_{50}$ of semaglutide, wherein the IC$_{50}$ of semaglutide is determined in the same way as the IC$_{50}$ of the derivative.

213. The derivative of any of embodiments 1-212, which at a low concentration of HSA is capable of binding to the human GLP-1 receptor with an IC$_{50}$ of less than 3 times the IC$_{50}$ of semaglutide, wherein the IC$_{50}$ of semaglutide is determined in the same way as the IC$_{50}$ of the derivative.

214. The derivative of any of embodiments 1-213, which at a low concentration of HSA is capable of binding to the human GLP-1 receptor with an IC$_{50}$ of less than 2 times the IC$_{50}$ of semaglutide, wherein the IC$_{50}$ of semaglutide is determined in the same way as the IC$_{50}$ of the derivative.

215. The derivative of any of embodiments 1-214, which at a low concentration of HSA is capable of binding to the human GLP-1 receptor with an IC$_{50}$ of less than 1.5 times the IC$_{50}$ of semaglutide, wherein the IC$_{50}$ of semaglutide is determined in the same way as the IC$_{50}$ of the derivative.

216. The derivative of any of embodiments 1-215, which at a low concentration of HSA is capable of binding to the human GLP-1 receptor with an IC$_{50}$ of less than 1 time the IC$_{50}$ of semaglutide, wherein the IC$_{50}$ of semaglutide is determined in the same way as the IC$_{50}$ of the derivative.

217. The derivative of any of embodiments 210-216, wherein the IC$_{50}$ is determined essentially as described in Example 30, in a reaction with max. 0.001% HSA (final assay concentration).

218. The derivative of any of embodiments 1-217, which at 2.0% HSA (final assay concentration) is capable of binding to the human GLP-1 receptor with an IC$_{50}$ of 950 nM or below.

219. The derivative of any of embodiments 1-218, which at 2.0% HSA (final assay concentration) is capable of binding to the human GLP-1 receptor with an IC$_{50}$ of 650 nM or below.

220. The derivative of any of embodiments 1-219, which at 2.0% HSA (final assay concentration) is capable of binding to the human GLP-1 receptor with an IC$_{50}$ of 550 nM or below.

221. The derivative of any of embodiments 1-220, which at 2.0% HSA (final assay concentration) is capable of binding to the human GLP-1 receptor with an IC$_{50}$ of 500 nM or below.

222. The derivative of any of embodiments 1-221, which at 2.0% HSA (final assay concentration) is capable of binding to the human GLP-1 receptor with an IC$_{50}$ of 400 nM or below.

223. The derivative of any of embodiments 1-222, which at 2.0% HSA (final assay concentration) is capable of binding to the human GLP-1 receptor with an IC$_{50}$ of 300 nM or below.

224. The derivative of any of embodiments 1-223, which at 2.0% HSA (final assay concentration) is capable of binding to the human GLP-1 receptor with an IC$_{50}$ of 200 nM or below.

225. The derivative of any of embodiments 1-224, which at 2.0% HSA (final assay concentration) is capable of binding to the human GLP-1 receptor with an IC$_{50}$ of 150 nM or below.

226. The derivative of any of embodiments 218-225, wherein the IC$_{50}$ is determined essentially as described in Example 30, in a reaction with 2.0% HSA (final assay concentration).

227. The derivative of any of embodiments 1-226, which at 2.0% HSA (final assay concentration) is capable of binding to the human GLP-1 receptor with an IC$_{50}$ of less than 3 times the IC$_{50}$ of semaglutide, wherein the IC$_{50}$ of semaglutide is determined in the same way as the IC$_{50}$ of the derivative.

228. The derivative of any of embodiments 1-227, which at 2.0% HSA (final assay concentration) is capable of binding to the human GLP-1 receptor with an IC$_{50}$ of less than 2 times the IC$_{50}$ of semaglutide, wherein the IC$_{50}$ of semaglutide is determined in the same way as the IC$_{50}$ of the derivative.

229. The derivative of any of embodiments 1-228, which at 2.0% HSA (final assay concentration) is capable of binding to the human GLP-1 receptor with an IC$_{50}$ of less than 1.5 times the IC$_{50}$ of semaglutide, wherein the IC$_{50}$ of semaglutide is determined in the same way as the IC$_{50}$ of the derivative.

230. The derivative of any of embodiments 1-229, which at 2.0% HSA (final assay concentration) is capable of binding to the human GLP-1 receptor with an IC$_{50}$ of less than 1 time the IC$_{50}$ of semaglutide, wherein the IC$_{50}$ of semaglutide is determined in the same way as the IC$_{50}$ of the derivative.

231. The derivative of any of embodiments 1-230, which at 2.0% HSA (final assay concentration) is capable of binding to the human GLP-1 receptor with an IC$_{50}$ of less than 0.8 times the IC$_{50}$ of semaglutide, wherein the IC$_{50}$ of semaglutide is determined in the same way as the IC$_{50}$ of the derivative.

232. The derivative of any of embodiments 1-231, which at 2.0% HSA (final assay concentration) is capable of binding to the human GLP-1 receptor with an IC$_{50}$ of less than 0.35 times the IC$_{50}$ of semaglutide, wherein the IC$_{50}$ of semaglutide is determined in the same way as the IC$_{50}$ of the derivative.

233. The derivative of any of embodiments 227-232, wherein the IC$_{50}$ is determined essentially as described in Example 30, in a reaction with 2.0% HSA (final assay concentration).

234. The derivative of any of embodiments 1-233, which has improved pharmacokinetic properties.

235. The derivative of any of embodiments 1-234, which has an increased half-life and/or a decreased clearance.

236. The derivative of any of embodiments 1-235, which is suitable for once-monthly administration.

237. The derivative of any of embodiments 1-236, for s.c. administration.

238. The derivative of any of embodiments 1-237, wherein the derivative is tested in vivo in pharmacokinetic (PK) studies.

239. The derivative of any of embodiments 1-238, wherein the derivative is tested in any suitable animal model, such as mouse, rat, monkey, dog, or pig.

240. The derivative of any of embodiments 1-239, which is compared with semaglutide.

241. The derivative of any of embodiments 1-240, which has an improved terminal half-life (T½) in vivo in minipigs after i.v. administration as compared to semaglutide.

242. The derivative of any of embodiments 1-241, wherein the terminal half-life is determined in vivo in minipigs after i.v. administration using any suitable study protocol, such as the one described in Example 31.

243. The derivative of any of embodiments 1-242, wherein the terminal half-life is determined in vivo in minipigs after i.v. administration, essentially as described in Example 31.

244. The derivative of any of embodiments 1-243, which has a terminal half-life (T½) in vivo in minipigs after i.v. administration of at least 90 hours.

245. The derivative of any of embodiments 1-244, which has a terminal half-life (T½) in vivo in minipigs after i.v. administration of at least 100 hours.
246. The derivative of any of embodiments 1-245, which has a terminal half-life (T½) in vivo in minipigs after i.v. administration of at least 125 hours.
247. The derivative of any of embodiments 1-246, which has a terminal half-life (T½) in vivo in minipigs after i.v. administration of at least 140 hours.
248. The derivative of any of embodiments 1-247, which has a terminal half-life (T½) in vivo in minipigs after i.v. administration of at least 1.5 times the terminal half-life of semaglutide, determined in the same way.
249. The derivative of any of embodiments 1-248, which has a terminal half-life (T½) in vivo in minipigs after i.v. administration of at least 2 times the terminal half-life of semaglutide, determined in the same way.
250. The derivative of any of embodiments 1-249, which has a terminal half-life (T½) in vivo in minipigs after i.v. administration of at least 2.3 times the terminal half-life of semaglutide, determined in the same way.
251. The derivative of any of embodiments 1-250, which has a terminal half-life (T½) in vivo in minipigs after i.v. administration of at least 2.6 times the terminal half-life of semaglutide, determined in the same way.
252. The derivative of any of embodiments 1-251, which is potent in vivo.
253. The derivative of any of embodiments 1-252, which is potent in vivo when determined in any suitable animal model, such as mouse or pig.
254. The derivative of any of embodiments 1-253, wherein the animal model is db/db mouse.
255. The derivative of any of embodiments 1-254, wherein the blood glucose lowering effect is determined.
256. The derivative of any of embodiments 1-255, wherein the body weight lowering effect is determined.
257. The derivative of any of embodiments 1-256, wherein blood glucose lowering effect and/or body weight lowering effect is determined in vivo in db/db mouse using any suitable study protocol and methodology, e.g. as described in Example 32.
258. The derivative of any of embodiments 1-257, wherein the blood glucose lowering effect and/or the body weight lowering effect is determined in vivo in db/db mouse, essentially as described in Example 32.
259. The derivative of any of embodiments 1-258, which has the effect in vivo of reducing blood glucose after 48 hours, determined in a single-dose study in a db/db mouse model.
260. The derivative of any of embodiments 1-259, wherein the blood glucose is reduced by at least 15%, as compared to the blood glucose level before administration of the derivative.
261. The derivative of any of embodiments 1-260, wherein the blood glucose is reduced by at least 25%, as compared to the blood glucose level before administration of the derivative.
262. The derivative of any of embodiments 1-261 wherein the blood glucose is reduced by at least 35%, as compared to the blood glucose level before administration of the derivative.
263. The derivative of any of embodiments 1-262, wherein the blood glucose is reduced by at least 50%, as compared to the blood glucose level before administration of the derivative.
264. The derivative of any of embodiments 1-263, which has the effect in vivo of reducing blood glucose after 72 hours, determined in a single-dose study in a db/db mouse model.
265. The derivative of any of embodiments 1-264, which has the effect in vivo of reducing blood glucose after 96 hours, determined in a single-dose study in a db/db mouse model.
266. The derivative of any of embodiments 1-265, wherein the blood glucose is reduced by at least 3%, as compared to the blood glucose level before administration of the derivative.
267. The derivative of any of embodiments 1-266, wherein the blood glucose is reduced by at least 5%, as compared to the blood glucose level before administration of the derivative.
268. The derivative of any of embodiments 1-267, wherein the blood glucose is reduced by at least 10%, as compared to the blood glucose level before administration of the derivative.
269. The derivative of any of embodiments 1-268, wherein the blood glucose is reduced by at least 15%, as compared to the blood glucose level before administration of the derivative.
270. The derivative of any of embodiments 1-269, wherein the blood glucose is reduced by at least 20%, as compared to the blood glucose level before administration of the derivative.
271. The derivative of any of embodiments 1-270, wherein the blood glucose is reduced by at least 25%, as compared to the blood glucose level before administration of the derivative.
272. The derivative of any of embodiments 1-271, which has the effect in vivo of reducing body weight after 48 hours, determined in a single-dose study in a db/db mouse model.
273. The derivative of any of embodiments 1-272, wherein the body weight is reduced by at least 3%, as compared to the body weight before administration of the derivative.
274. The derivative of any of embodiments 1-273, wherein the body weight is reduced by at least 4%, as compared to the body weight before administration of the derivative.
275. The derivative of any of embodiments 1-274, wherein the body weight is reduced by at least 5%, as compared to the body weight before administration of the derivative.
276. The derivative of any of embodiments 1-275, wherein the body weight is reduced by at least 6%, as compared to the body weight before administration of the derivative.
277. The derivative of any of embodiments 1-276, which has the effect in vivo of reduced body weight after 72 hours, determined in a single-dose study in a db/db mouse model.
278. The derivative of any of embodiments 1-277 which has the effect in vivo of reducing body weight after 96 hours, determined in a single-dose study in a db/db mouse model.
279. The derivative of any of embodiments 1-278, wherein the body weight is reduced by at least 1%, as compared to the body weight before administration of the derivative.
280. The derivative of any of embodiments 1-279, wherein the body weight is reduced by at least 2%, as compared to the body weight before administration of the derivative.
281. The derivative of any of embodiments 1-280, wherein the body weight is reduced by at least 3%, as compared to the body weight before administration of the derivative.
282. The derivative of any of embodiments 1-281, wherein the body weight is reduced by at least 4%, as compared to the body weight before administration of the derivative.
283. The derivative of any of embodiments 1-282, wherein the animal model is pig.
284. The derivative of any of embodiments 1-283, wherein the animal model is LYD pig.
285. The derivative of any of embodiments 1-284, wherein the reduction in food intake is determined in an in vivo pharmacodynamic (PD) study.

286. The derivative of any of embodiments 1-285, wherein the reduction in food intake is determined in vivo in pig using any suitable study protocol and methodology, e.g. as described in Example 33.

287. The derivative of any of embodiments 1-286, wherein the reduction in food intake is determined in vivo in pig using any suitable study protocol and methodology, essentially as described in Example 33.

288. The derivative of any of embodiments 1-287, which has the effect in vivo of reducing food intake during a first period of 24 hours (0-24 hours) after administration of a single dose of the derivative, wherein food intake is determined in a single-dose study in a LYD pig model.

289. The derivative of any of embodiments 1-288, which has the effect in vivo of reducing food intake during a second period of 24 hours (24-48 hours) after administration of a single dose of the derivative, wherein food intake is determined in a single-dose study in a LYD pig model.

290. The derivative of any of embodiments 1-289, which has the effect in vivo of reducing food intake during a third period of 24 hours (48-72 hours) after administration of a single dose of the derivative, wherein food intake is determined in a single-dose study in a LYD pig model.

291. The derivative of any of embodiments 1-290, which has the effect in vivo of reducing food intake during a fourth period of 24 hours (72-96 hours) after administration of a single dose of the derivative, wherein food intake is determined in a single-dose study in a LYD pig model.

292. A GLP-1 derivative selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, and Chem. 48; or a pharmaceutically acceptable salt, amide, or ester thereof.

293. A GLP-1 derivative selected from the chemical structures shown in any of Examples 1-28; or a pharmaceutically acceptable salt, amide, or ester thereof.

294. A GLP-1 derivative selected from the GLP-1 derivative names shown in any of Examples 1-28; or a pharmaceutically acceptable salt, amide, or ester thereof.

295. The derivative of any of embodiments 292-294, which is a derivative according to any of embodiments 1-291.

296. An intermediate product in the form of a GLP-1 analogue, which comprises the following amino acid changes when compared to GLP-1 (7-37) (SEQ ID NO: 1):
i) (8Aib, 22E, 26R, 27K, 34R, 38G, 39G, 40G, 41S, 42K);
ii) (8Aib, 22E, 26R, 31K, 34R, 38G, 39G, 40G, 41S, 42K);
iii) (8Aib, 22E, 26R, 34R, 38K, 39G, 40G, 41S, 42K); iv) (8Aib, 22E, 23K, 26R, 34R, 38G, 39G, 40G, 41S, 42K); v) (8Aib, 22E, 26R, 34R, 36K, 38G, 39G, 40G, 41S, 42K); vi) (8Aib, 18K, 22E, 26R, 34R, 38G, 39G, 40G, 41S, 42K); vii) (7Imp, 8Aib, 22E, 26R, 34R, 38K, 39G, 40G, 41S, 42K); iix) (8Aib, 22E, 26R, 34R, 36K, 38A, 39E, 40S, 41P, 42K); ix) (8Aib, 22E, 26R, 34R, 36K, 38E, 39G, 40P, 41A, 42K); x) (8Aib, 22E, 26R, 34R, 36K, 38P, 39A, 40S, 41E, 42K); xi) (8Aib, 22E, 26R, 34R, 38K, 39P, 40E, 41G, 42K) (SEQ ID NO: 12); xii) (8Aib, 22E, 26R, 34R, 38K, 39S, 40A, 41E, 42K); or xiii) (8Aib, 22E, 26R, 34R, 38K, 39S, 40P, 41E, 42K).

297. An intermediate product in the form of a GLP-1 analogue, selected from the following analogues of GLP-1 (7-37) (SEQ ID NO: 1):
i) (8Aib, 22E, 26R, 27K, 34R, 38G, 39G, 40G, 41S, 42K) (SEQ ID NO: 2); ii) (8Aib, 22E, 26R, 31K, 34R, 38G, 39G, 40G, 41S, 42K) (SEQ ID NO: 3); iii) (8Aib, 22E, 26R, 34R, 38K, 39G, 40G, 41S, 42K) (SEQ ID NO: 4); iv (8Aib, 22E, 23K, 26R, 34R, 38G, 39G, 40G, 41S, 42K) (SEQ ID NO: 5); v) (8Aib, 22E, 26R, 34R, 36K, 38G, 39G, 40G, 41S, 42K) (SEQ ID NO: 6); vi) (8Aib, 18K, 22E, 26R, 34R, 38G, 39G, 40G, 41S, 42K) (SEQ ID NO: 8), vii) (7Imp, 8Aib, 22E, 26R, 34R, 38K, 39G, 40G, 41S, 42K) (SEQ ID NO: 8); iix) (8Aib, 22E, 26R, 34R, 36K, 38A, 39E, 40S, 41P, 42K) (SEQ ID NO: 9); ix) (8Aib, 22E, 26R, 34R, 36K, 38E, 39G, 40P, 41A, 42K) (SEQ ID NO: 10); x) (8Aib, 22E, 26R, 34R, 36K, 38P, 39A, 40S, 41E, 42K) (SEQ ID NO: 11); xi) (8Aib, 22E, 26R, 34R, 38K, 39P, 40E, 41G, 42K) (SEQ ID NO: 12); xii) (8Aib, 22E, 26R, 34R, 38K, 39S, 40A, 41E, 42K) (SEQ ID NO: 13); and xiii) (8Aib, 22E, 26R, 34R, 38K, 39S, 40P, 41E, 42K) (SEQ ID NO: 14).

298. A pharmaceutical composition comprising a derivative according to any of embodiments 1-295, or an analogue according to any of embodiments 296-297, and a pharmaceutically acceptable excipient.

299. A derivative according to any of embodiments 1-295, or an analogue according to any of embodiments 296-297, for use as a medicament.

300. A derivative according to any of embodiments 1-295, or an analogue according to any of embodiments 296-297, for use in
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;
(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;
(iii) improving β-cell function, such as decreasing β-cell apoptosis, increasing β-cell function and/or β-cell mass, and/or for restoring glucose sensitivity to β-cells;
(iv) prevention and/or treatment of cognitive disorders and/or neurodegenerative disorders, such as Alzheimer's disease, Parkinson's disease, and/or multiple sclerosis;
(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;
(vi) prevention and/or treatment of diabetic complications, such as angiopathy; neuropathy, including peripheral neuropathy; nephropathy; and/or retinopathy;
(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;
(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

301. Use of a derivative according to any of embodiments 1-208, or an analogue according to any of embodiments 209-210, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

302. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/ or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative according to any of embodiments 1-295, or an analogue according to any of embodiments 296-297, is administered.

Additional Particular Embodiments

The following are additional particular embodiments of the invention:

1. A derivative of a GLP-1 like peptide of formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{33}$-Xaa$_{40}$-Xaa$_{41}$-Xaa$_{42}$, Formula I:

wherein

Xaa$_7$ is L-histidine, (S)-2-Hydroxy-3-(1H-imidazol-4-yl)-propionic acid, D-histidine, desamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;

Xaa$_8$ is Ala, Gly, Ser, Aib, (1-aminocyclopropyl)carboxylic acid, or (1-aminocyclobutyl)carboxylic acid;

Xaa$_{12}$ is Phe or Leu;

Xaa$_{16}$ is Val or Leu;

Xaa$_{18}$ is Ser, Arg, Lys, Val, or Leu;

Xaa$_{19}$ is Tyr or Gln;

Xaa$_{20}$ is Leu or Met;

Xaa$_{22}$ is Gly or Glu;

Xaa$_{23}$ is Gln, Glu, Lys, or Arg;

Xaa$_{25}$ is Ala or Val;

Xaa$_{26}$ is Arg or Lys;

Xaa$_{27}$ is Glu, Lys, or Leu;

Xaa$_{30}$ is Ala, Glu, or Arg;

Xaa$_{31}$ is Trp, Lys, or His;

Xaa$_{33}$ is Val, Lys, or Arg;

Xaa$_{34}$ is Lys, Arg, His, Asn, or Gln;

Xaa$_{35}$ is Gly or Ala;

Xaa$_{36}$ is Arg, Lys, or Gly;

Xaa$_{37}$ is Gly or Pro;

Xaa$_{38}$ is Ser, Gly, Ala, Glu, Pro, or Lys;

Xaa$_{39}$ is Ser, Gly, Ala, Glu, or Pro;

Xaa$_{40}$ is Ser, Gly, Ala, Glu, or Pro;

Xaa$_{41}$ is Ser, Gly, Ala, Glu, or Pro; and

Xaa$_{42}$ is Lys;

with the proviso that at least one of Xaa$_{18}$, Xaa$_{23}$, Xaa$_{27}$, Xaa$_{31}$, Xaa$_{36}$, or Xaa$_{38}$ is Lys;

wherein

Lys at Xaa$_{42}$ is a first K residue, and a Lys at one of Xaa$_{18}$, Xaa$_{23}$, Xaa$_{27}$, Xaa$_{31}$, Xaa$_{36}$, or Xaa$_{38}$ is a second K residue;

which derivative comprises a first and a second protracting moiety connected to said first and second K residue, respectively, wherein the first and second protracting moiety is of formula Chem. 1:

$$\text{HOOC—(CH}_2\text{)}_{18}\text{—CO—*}; \qquad \text{Chem. 1:}$$

or a pharmaceutically acceptable salt, amide, or ester thereof.

2. The derivative of embodiment 1, wherein each of the first and the second protracting moiety is attached to the first and the second K residue, respectively, optionally via a first and a second linker, respectively.

3. The derivative of embodiment 2, wherein the first and the second linker each incorporates an *—NH group, and a *—CO group.

4. The derivative of any of embodiments 2-3, wherein each of the first and the second linker comprises an element_1 of formula Chem. 2:

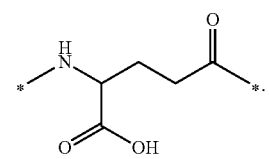

Chem. 2

5. The derivative of embodiment 4, wherein each of the first and the second linker incorporates one element_1 of formula Chem. 2.

6. The derivative of any of embodiments 4-5, wherein Chem. 2 represents a gGlu residue.

7. The derivative of any of embodiments 4-6, wherein element_1 is an L-gGlu residue.

8. The derivative of any of embodiments 2-7, wherein each of the first and the second linker comprises an element_2 of formula Chem. 3:

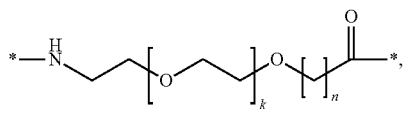

Chem. 3 wherein k is an integer in the range of 1-5, and n is an integer in the range of 1-5.

9. The derivative of embodiment 8, wherein each of the first and the second linker comprises at least one element_2 of formula Chem. 3.

10. The derivative of any of embodiments 8-9, wherein each of the first and the second linker comprises at least two elements_2 of formula Chem. 3.

11. The derivative of any of embodiments 8-10, wherein each of the first and the second linker comprises two elements_2 of formula Chem. 3.

12. The derivative of any of embodiments 8-11, wherein each of the first and the second linker incorporates two elements_2 of formula Chem. 3.

13. The derivative of any of embodiments 8-12, wherein k=1 and n=1.

14. The derivative of any of embodiments 8-13, wherein Chem. 3 represents OEG.

15. The derivative of any of embodiments 2-14, wherein each of the first and the second linker comprises an element_3 of formula Chem. 4:

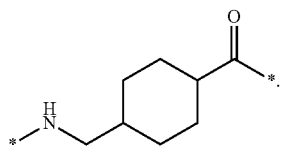

Chem. 4

16. The derivative of any of embodiments 2-15, wherein each of the first and second linker each incorporates one element_3 of formula Chem. 4.

17. The derivative of any of embodiments 15-16, wherein Chem. 4 represents Trx.

18. The derivative of any of embodiments 2-17, wherein each of the first and the second linker comprises an element_4 of formula Chem. 5:

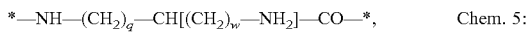

*—NH—(CH$_2$)$_q$—CH[(CH$_2$)$_w$—NH$_2$]—CO—*,    Chem. 5:

wherein q is an integer in the range of 0-5, and w is an integer in the range of 0-5, with the provisos that when w is 0 q is an integer in the range of 1-5, and when q is 0 w is an integer in the range of 1-5.

19. The derivative of embodiment 18, wherein each of the first and the second linker comprises at least one element_4 of formula Chem. 5.

20. The derivative of any of embodiments 18-19, wherein each of the first and the second linker comprises at least two elements_4 of formula Chem. 5.

21. The derivative of any of embodiments 18-20, wherein each of the first and the second linker comprises two elements_4 of formula Chem. 5.

22. The derivative of any of embodiments 18-21, wherein each of the first and the second linker incorporates two elements_4 of formula Chem. 5.

23. The derivative of any of embodiments 18-22, wherein q is 4 and w is 0.

24. The derivative of any of embodiments 18-22, wherein w is 4 and q is 0.

25. The derivative of any of embodiments 18-24, wherein Chem. 5 represents an eps-Lys residue.

25a. The derivative of any of embodiments 18-25, wherein element_4 is an L-eps-Lys residue.

26. The derivative of any of embodiments 2-25a, wherein each of the first and the second linker consists of one element_3 of formula Chem. 4, one element_1 of formula Chem. 2, and two elements_2 of formula Chem. 3 wherein k=1 and n=1, interconnected via amide bonds and in the sequence indicated.

27. The derivative of any of embodiments 2-25a, wherein each of the first and the second linker consists of one element_3 of formula Chem. 4, one element_1 of formula Chem. 2, and two elements_4 of formula Chem. 5 wherein q=4 and w=0 (or w=4 and q=0), interconnected via amide bonds and in the sequence indicated.

28. The derivative of any of embodiments 2-25a, wherein each of the first and the second linker consists of one element_1 of formula Chem. 2 and two elements_4 of formula Chem. 5 wherein q=4 and w=0 (or w=4 and q=0), interconnected via amide bonds and in the sequence indicated.

29. The derivative of any of embodiments 1-28, wherein the CO—* group of Chem. 1 of each of the first and second protracting moieties is attached to the epsilon amino group of the first and second K residue, respectively, optionally via a first and a second linker, respectively.

30. The derivative of any of embodiments 1-29, wherein each of the first and the second protracting moiety is attached to the epsilon amino group of the first and the second K-residue, respectively, under the formation of an amide bond, optionally via a first and a second linker, respectively, which is connected via amide bonds to the first and the second protracting moiety as well as to the first and the second K residue.

31. The derivative of any of embodiments 1-30, wherein the CO—* group of Chem. 1 of each of the first and second protracting moieties is attached to an *—NH group of a first and a second linker, respectively, and a *—CO group of each of the first and the second linker is attached to the epsilon amino group of the first and the second K-residue, respectively.

31a. The derivative of any of embodiments 1-31, wherein one of $Xaa_{18}$, $Xaa_{23}$, $Xaa_{27}$, $Xaa_{31}$, $Xaa_{36}$, or $Xaa_{38}$ is Lys.

31b. The derivative of any of embodiments 1-31a, wherein only one of $Xaa_{18}$, $Xaa_{23}$, $Xaa_{27}$, $Xaa_{31}$, $Xaa_{36}$, or $Xaa_{38}$ is Lys.

32. The derivative of any of embodiments 1-31b, wherein a Lys at $Xaa_{18}$ is the second K residue.

33. The derivative of any of embodiments 1-31b, wherein a Lys at $Xaa_{23}$ is the second K residue.

34. The derivative of any of embodiments 1-31b, wherein a Lys at $Xaa_{27}$ is the second K residue.

35. The derivative of any of embodiments 1-31b, wherein a Lys at $Xaa_{31}$ is the second K residue.

36. The derivative of any of embodiments 1-31b, wherein a Lys at $Xaa_{36}$ is the second K residue.

37. The derivative of any of embodiments 1-31b, wherein a Lys at $Xaa_{38}$ is the second K residue.

38. The derivative of any of embodiments 1-37, wherein $Xaa_7$ is His.
39. The derivative of any of embodiments 1-38, wherein $Xaa_8$ is Aib.
40. The derivative of any of embodiments 1-39, wherein $Xaa_{12}$ is Phe.
41. The derivative of any of embodiments 1-40, wherein $Xaa_{16}$ is Val.
42. The derivative of any of embodiments 1-41, wherein $Xaa_{18}$ is Ser or Lys.
43. The derivative of any of embodiments 1-42, wherein $Xaa_{18}$ is Ser.
44. The derivative of any of embodiments 1-42, wherein $Xaa_{18}$ is Lys.
45. The derivative of any of embodiments 1-44, wherein $Xaa_{19}$ is Tyr.
46. The derivative of any of embodiments 1-45, wherein $Xaa_{20}$ is Leu.
47. The derivative of any of embodiments 1-46, wherein $Xaa_{22}$ is Glu.
48. The derivative of any of embodiments 1-47, wherein $Xaa_{23}$ is Gln or Lys.
49. The derivative of any of embodiments 1-48, wherein $Xaa_{23}$ is Gln.
50. The derivative of any of embodiments 1-48, wherein $Xaa_{23}$ is Lys.
51. The derivative of any of embodiments 1-50, wherein $Xaa_{25}$ is Ala.
52. The derivative of any of embodiments 1-51, wherein $Xaa_{26}$ is Arg.
53. The derivative of any of embodiments 1-52, wherein $Xaa_{27}$ is Glu or Lys.
54. The derivative of any of embodiments 1-53, wherein $Xaa_{27}$ is Glu.
55. The derivative of any of embodiments 1-54, wherein $Xaa_{27}$ is Glu or Lys.
56. The derivative of any of embodiments 1-54, wherein $Xaa_{27}$ is Lys.
57. The derivative of any of embodiments 1-56, wherein $Xaa_{30}$ is Ala.
58. The derivative of any of embodiments 1-57, wherein $Xaa_{31}$ is Trp or Lys.
59. The derivative of any of embodiments 1-58, wherein $Xaa_{31}$ is Lys.
60. The derivative of any of embodiments 1-58, wherein $Xaa_{31}$ is Trp.
61. The derivative of any of embodiments 1-60, wherein $Xaa_{33}$ is Val.
62. The derivative of any of embodiments 1-61, wherein $Xaa_{34}$ is Arg.
63. The derivative of any of embodiments 1-62, wherein $Xaa_{35}$ is Gly.
64. The derivative of any of embodiments 1-63, wherein $Xaa_{36}$ is Arg or Lys.
65. The derivative of any of embodiments 1-64, wherein $Xaa_{36}$ is Arg.
66. The derivative of any of embodiments 1-64, wherein $Xaa_{36}$ is Lys.
67. The derivative of any of embodiments 1-66, wherein $Xaa_{37}$ is Gly.
68. The derivative of any of embodiments 1-70, wherein $Xaa_{37}$ is Lys.
73. The derivative of any of embodiments 1-72, wherein $Xaa_{38}$ is Gly or Lys.
74. The derivative of any of embodiments 1-73, wherein $Xaa_{38}$ is Gly.
75. The derivative of any of embodiments 1-73, wherein $Xaa_{38}$ is Lys.
76. The derivative of any of embodiments 1-75, wherein $Xaa_{39}$ is Gly.
77. The derivative of any of embodiments 1-76, wherein $Xaa_{40}$ is Gly.
78. The derivative of any of embodiments 1-77, wherein $Xaa_{41}$ is Ser.
79. The derivative of any of embodiments 1-78, wherein the GLP-1 like peptide has a maximum of 12 amino acid changes, when compared with GLP-1(7-37) (SEQ ID NO: 1).
80. The derivative of any of embodiments 1-79, wherein the GLP-1 like peptide has a maximum of 11 amino acid changes, when compared with GLP-1(7-37) (SEQ ID NO: 1).
81. The derivative of any of embodiments 1-80, wherein the GLP-1 like peptide has a maximum of 10 amino acid changes, when compared with GLP-1(7-37) (SEQ ID NO: 1).
82. The derivative of any of embodiments 1-81, wherein the GLP-1 like peptide has a maximum of 9 amino acid changes, when compared with GLP-1(7-37) (SEQ ID NO: 1).
83. The derivative of any of embodiments 1-82, wherein the GLP-1 like peptide has a maximum of 8 amino acid changes, when compared with GLP-1(7-37) (SEQ ID NO: 1).
84. The derivative of any of embodiments 1-83, wherein the GLP-1 like peptide has a maximum of 7 amino acid changes, when compared with GLP-1(7-37) (SEQ ID NO: 1).
85. The derivative of any of embodiments 1-84, wherein the GLP-1 like peptide has a maximum of 6 amino acid changes, when compared with GLP-1(7-37) (SEQ ID NO: 1).
86. The derivative of any of embodiments 1-85, wherein the GLP-1 like peptide has a maximum of 5 amino acid changes, when compared with GLP-1(7-37) (SEQ ID NO: 1).
87. The derivative of any of embodiments 1-86, wherein the GLP-1 like peptide has a minimum of 5 amino acid changes, when compared with GLP-1(7-37) (SEQ ID NO: 1).
88. The derivative of any of embodiments 1-87, wherein the GLP-1 like peptide has a minimum of 6 amino acid changes, when compared with GLP-1(7-37) (SEQ ID NO: 1).
89. The derivative of any of embodiments 1-88, wherein the GLP-1 like peptide has a minimum of 7 amino acid changes, when compared with GLP-1(7-37) (SEQ ID NO: 1).
90. The derivative of any of embodiments 1-89, wherein the GLP-1 like peptide has a minimum of 8 amino acid changes, when compared with GLP-1(7-37) (SEQ ID NO: 1).
91. The derivative of any of embodiments 1-90, wherein the GLP-1 like peptide has a minimum of 9 amino acid changes, when compared with GLP-1(7-37) (SEQ ID NO: 1).
92. The derivative of any of embodiments 1-91, wherein the GLP-1 like peptide has a minimum of 10 amino acid changes, when compared with GLP-1(7-37) (SEQ ID NO: 1).
93. The derivative of any of embodiments 1-92, wherein the GLP-1 like peptide has 5 amino acid changes, when compared with GLP-1(7-37) (SEQ ID NO: 1).
94. The derivative of any of embodiments 1-92, wherein the GLP-1 like peptide has 6 amino acid changes, when compared with GLP-1(7-37) (SEQ ID NO: 1).
95. The derivative of any of embodiments 1-92, wherein the GLP-1 like peptide has 7 amino acid changes, when compared with GLP-1(7-37) (SEQ ID NO: 1).
96. The derivative of any of embodiments 1-92, wherein the GLP-1 like peptide has 8 amino acid changes, when compared with GLP-1(7-37) (SEQ ID NO: 1).

97. The derivative of any of embodiments 1-92, wherein the GLP-1 like peptide has 9 amino acid changes, when compared with GLP-1(7-37) (SEQ ID NO: 1).
98. The derivative of any of embodiments 1-92, wherein the GLP-1 like peptide has 10 amino acid changes, when compared with GLP-1(7-37) (SEQ ID NO: 1).
99. The derivative of any of embodiments 1-98, wherein the GLP-1 like peptide comprises at least two Lys residues.
99a. The derivative of any of embodiments 1-99, wherein the GLP-1 like peptide comprises two Lys residues.
99b. The derivative of any of embodiments 1-99a, wherein the GLP-1 like peptide has two Lys residues.
99c. The derivative of any of embodiments 1-99b, wherein the GLP-1 like peptide has only two Lys residues.
100. The derivative of any of embodiments 1-99c, wherein the GLP-1 like peptide is selected from the following analogues of GLP-1 (7-37) (SEQ ID NO: 1): i) (8Aib, 22E, 26R, 27K, 34R, 38G, 39G, 40G, 41S, 42K); ii) (8Aib, 22E, 26R, 31K, 34R, 38G, 39G, 40G, 41S, 42K); iii) (8Aib, 22E, 26R, 34R, 38K, 39G, 40G, 41S, 42K); iv (8Aib, 22E, 23K, 26R, 34R, 38G, 39G, 40G, 41S, 42K); v) (8Aib, 22E, 26R, 34R, 36K, 38G, 39G, 40G, 41S, 42K); and vi) (8Aib, 18K, 22E, 26R, 34R, 38G, 39G, 40G, 41S, 42K).
101. The derivative of any of embodiments 1-100, in the form of a sodium or potassium salt thereof.
102. The derivative of any of embodiments 1-101 which is a GLP-1 receptor agonist.
103. The derivative of embodiment 102, which is a full GLP-1 receptor agonist.
104. The derivative of any of embodiments 1-103, which is biologically active in vitro.
105. The derivative of any of embodiments 1-104, which is potent in vitro.
106. The derivative of any of embodiments 1-105, which is capable of activating the human GLP-1 receptor.
107. The derivative of any of embodiments 1-106 which is capable of activating the human GLP-1 receptor in an assay with whole cells expressing the human GLP-1 receptor, wherein the assay is performed in the absence of HSA (0% HSA), and/or in the presence of HSA (1% HSA).
108. The derivative of embodiment 107, where the response of the human GLP-1 receptor is measured in a reporter gene assay, such as the assay of Example 9.
109. The derivative of any of embodiments 104-108, wherein the biological activity, or potency, in vitro is determined essentially as described in Example 9.
110. The derivative of any of embodiments 1-109, which has an in vitro potency corresponding to an $EC_{50}$ of 400 pM or below.
111. The derivative of any of embodiments 1-110, which has an in vitro potency corresponding to an $EC_{50}$ of 300 pM or below.
112. The derivative of any of embodiments 1-111, which has an in vitro potency corresponding to an $EC_{50}$ of 100 pM or below.
113. The derivative of any of embodiments 1-112, which has an in vitro potency corresponding to an $EC_{50}$ of 75 pM or below.
114. The derivative of any of embodiments 1-113, which has an in vitro potency corresponding to an $EC_{50}$ of 55 pM or below.
115. The derivative of any of embodiments 1-114, which has an in vitro potency corresponding to an $EC_{50}$ of 40 pM or below.
116. The derivative of any of embodiments 110-115, wherein the $EC_{50}$ is determined essentially as described in Example 9.
117. The derivative of any of embodiments 1-116, which has an in vitro potency corresponding to an $EC_{50}$ of less than 40 times the $EC_{50}$ of semaglutide, wherein the $EC_{50}$ of semaglutide is determined in the same way as the $EC_{50}$ of the derivative.
118. The derivative of any of embodiments 1-117, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.
119. The derivative of any of embodiments 1-118, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.
120. The derivative of any of embodiments 1-119, which has an in vitro potency corresponding to an $EC_{50}$ of less than 8 times the $EC_{50}$ of semaglutide, wherein the $EC_{50}$ of semaglutide is determined in the same way as the $EC_{50}$ of the derivative.
121. The derivative of any of embodiments 1-120, which has an in vitro potency corresponding to an $EC_{50}$ of less than 5 times the $EC_{50}$ of semaglutide, wherein the $EC_{50}$ of semaglutide is determined in the same way as the $EC_{50}$ of the derivative.
122. The derivative of any of embodiments 1-121, which has an in vitro potency corresponding to an $EC_{50}$ of less than 3.5 times the $EC_{50}$ of semaglutide, wherein the $EC_{50}$ of semaglutide is determined in the same way as the $EC_{50}$ of the derivative.
123. The derivative of any of embodiments 117-122, wherein the $EC_{50}$ is determined essentially as described in Example 9.
124. The derivative of any of embodiments 1-123, which is capable of binding to the GLP-1 receptor.
125. The derivative of any of embodiments 1-124, which is capable of binding to the GLP-1 receptor at a low concentration of HSA (max. 0.001% final assay concentration).
126. The derivative of any of embodiments 1-125, which is capable of binding to the GLP-1 receptor at a high concentration of HSA (2.0% final assay concentration).
127. The derivative of any of embodiments 124-126, wherein the binding to the human GLP-1 receptor is measured in a competitive binding assay, such as the assay of Example 10.
128. The derivative of any of embodiments 124-127, wherein the binding to the human GLP-1 receptor in vitro is determined essentially as described in Example 10.
129. The derivative of any of embodiments 1-128, which at a very low concentration of HSA is capable of binding to the human GLP-1 receptor with an $IC_{50}$ of 3.0 nM or below.
130. The derivative of any of embodiments 1-129, which at a very low concentration of HSA is capable of binding to the human GLP-1 receptor with an $IC_{50}$ of 2.0 nM or below.
131. The derivative of any of embodiments 1-130, which at a very low concentration of HSA is capable of binding to the human GLP-1 receptor with an $IC_{50}$ of 1.0 nM or below.
132. The derivative of any of embodiments 1-131, which at a very low concentration of HSA is capable of binding to the human GLP-1 receptor with an $IC_{50}$ of 0.8 nM or below.
133. The derivative of any of embodiments 129-132, wherein the $IC_{50}$ is determined essentially as described in Example 10, in a reaction with max. 0.001% HSA (final assay concentration).
134. The derivative of any of embodiments 1-133, which at a very low concentration of HSA is capable of binding to the human GLP-1 receptor with an $IC_{50}$ of less than 3 times the IC$_{50}$ of semaglutide, wherein the IC$_{50}$ of semaglutide is determined in the same way as the IC$_{50}$ of the derivative.
135. The derivative of any of embodiments 1-134, which at a very low concentration of HSA is capable of binding to the human GLP-1 receptor with an IC$_{50}$ of less than 2 times the IC$_{50}$ of semaglutide, wherein the IC$_{50}$ of semaglutide is determined in the same way as the IC$_{50}$ of the derivative.
136. The derivative of any of embodiments 1-135, which at a very low concentration of HSA is capable of binding to the human GLP-1 receptor with an IC$_{50}$ of less than 1.5 times the IC$_{50}$ of semaglutide, wherein the IC$_{50}$ of semaglutide is determined in the same way as the IC$_{50}$ of the derivative.
137. The derivative of any of embodiments 1-136, which at a very low concentration of HSA is capable of binding to the human GLP-1 receptor with an IC$_{50}$ of less than 1 time the IC$_{50}$ of semaglutide, wherein the IC$_{50}$ of semaglutide is determined in the same way as the IC$_{50}$ of the derivative.
138. The derivative of any of embodiments 134-137, wherein the IC$_{50}$ is determined essentially as described in Example 10, in a reaction with max. 0.001% HSA (final assay concentration).
139. The derivative of any of embodiments 1-138, which at 2.0% HSA (final assay concentration) is capable of binding to the human GLP-1 receptor with an IC$_{50}$ of 400 nM or below.
140. The derivative of any of embodiments 1-139, which at 2.0% HSA (final assay concentration) is capable of binding to the human GLP-1 receptor with an IC$_{50}$ of 300 nM or below.
141. The derivative of any of embodiments 1-140, which at 2.0% HSA (final assay concentration) is capable of binding to the human GLP-1 receptor with an IC$_{50}$ of 200 nM or below.
142. The derivative of any of embodiments 1-141, which at 2.0% HSA (final assay concentration) is capable of binding to the human GLP-1 receptor with an IC$_{50}$ of 150 nM or below.
143. The derivative of any of embodiments 139-142, wherein the IC$_{50}$ is determined essentially as described in Example 10, in a reaction with 2.0% HSA (final assay concentration).
144. The derivative of any of embodiments 1-143, which at 2.0% HSA (final assay concentration) is capable of binding to the human GLP-1 receptor with an IC$_{50}$ of less than 1.5 times the IC$_{50}$ of semaglutide, wherein the IC$_{50}$ of semaglutide is determined in the same way as the IC$_{50}$ of the derivative.
145. The derivative of any of embodiments 1-144, which at 2.0% HSA (final assay concentration) is capable of binding to the human GLP-1 receptor with an IC$_{50}$ of less than 1 time the IC$_{50}$ of semaglutide, wherein the IC$_{50}$ of semaglutide is determined in the same way as the IC$_{50}$ of the derivative.
146. The derivative of any of embodiments 1-145, which at 2.0% HSA (final assay concentration) is capable of binding to the human GLP-1 receptor with an IC$_{50}$ of less than 0.8 times the IC$_{50}$ of semaglutide, wherein the IC$_{50}$ of semaglutide is determined in the same way as the IC$_{50}$ of the derivative.
147. The derivative of any of embodiments 1-146, which at 2.0% HSA (final assay concentration) is capable of binding to the human GLP-1 receptor with an IC$_{50}$ of less than 0.35 times the IC$_{50}$ of semaglutide, wherein the IC$_{50}$ of semaglutide is determined in the same way as the IC$_{50}$ of the derivative.
148. The derivative of any of embodiments 144-147, wherein the IC$_{50}$ is determined essentially as described in Example 10, in a reaction with 2.0% HSA (final assay concentration).
149. The derivative of any of embodiments 1-148, which has improved pharmacokinetic properties.
150. The derivative of any of embodiments 1-149, which has an increased half-life and/or a decreased clearance.
151. The derivative of any of embodiments 1-150, which is suitable for once-monthly administration.
152. The derivative of embodiment 151, for s.c. administration.
153. The derivative of any of embodiments 149-152, wherein the derivative is tested in vivo in pharmacokinetic (PK) studies.
154. The derivative of embodiment 153, wherein the derivative is tested in any suitable animal model, such as mouse, rat, monkey, dog, or pig.
155. The derivative of any of embodiments 149-154, which is compared with semaglutide.
156. The derivative of any of embodiments 1-155, which has an improved terminal half-life (T½) in vivo in minipigs after i.v. administration as compared to semaglutide.
157. The derivative of any of embodiments 149-156, wherein the terminal half-life is determined in vivo in minipigs after i.v. administration using any suitable study protocol, such as the one described in Example 11.
158. The derivative of any of embodiments 149-157, wherein the terminal half-life is determined in vivo in minipigs after i.v. administration, essentially as described in Example 11.
159. The derivative of any of embodiments 1-158, which has a terminal half-life (T½) in vivo in minipigs after i.v. administration of at least 90 hours.
160. The derivative of any of embodiments 1-159, which has a terminal half-life (T½) in vivo in minipigs after i.v. administration of at least 100 hours.
161. The derivative of any of embodiments 1-160, which has a terminal half-life (T½) in vivo in minipigs after i.v. administration of at least 125 hours.
162. The derivative of any of embodiments 1-161, which has a terminal half-life (T½) in vivo in minipigs after i.v. administration of at least 140 hours.
163. The derivative of any of embodiments 1-162, which has a terminal half-life (T½) in vivo in minipigs after i.v. administration of at least 1.5 times the terminal half-life of semaglutide, determined in the same way.
164. The derivative of any of embodiments 1-163, which has a terminal half-life (T½) in vivo in minipigs after i.v. administration of at least 2 times the terminal half-life of semaglutide, determined in the same way.
165. The derivative of any of embodiments 1-164, which has a terminal half-life (T½) in vivo in minipigs after i.v. administration of at least 2.3 times the terminal half-life of semaglutide, determined in the same way.
166. The derivative of any of embodiments 1-165, which has a terminal half-life (T½) in vivo in minipigs after i.v. administration of at least 2.6 times the terminal half-life of semaglutide, determined in the same way.
167. The derivative of any of embodiments 1-166, which is potent in vivo.
168. The derivative of any of embodiments 1-167, which is potent in vivo when determined in any suitable animal model, such as mouse or pig.
169. The derivative of embodiment 168, wherein the animal model is db/db mouse.

170. The derivative of any of embodiments 167-169, wherein the blood glucose lowering effect is determined.
171. The derivative of any of embodiments 167-170, wherein the body weight lowering effect is determined.
172. The derivative of any of embodiments 1-171, wherein blood glucose lowering effect and/or body weight lowering effect is determined in vivo in db/db mouse using any suitable study protocol and methodology, e.g. as described in Example 12.
173. The derivative of any of embodiments 1-172, wherein the blood glucose lowering effect and/or the body weight lowering effect is determined in vivo in db/db mouse, essentially as described in Example 12.
174. The derivative of any of embodiments 1-173, which has the effect in vivo of decreasing blood glucose after 48 hours, determined in a single-dose study in a db/db mouse model.
175. The derivative of embodiment 174, wherein the blood glucose is decreased by at least 15%, as compared to the blood glucose level before administration of the derivative.
176. The derivative of any of embodiments 174-175, wherein the blood glucose is decreased by at least 25%, as compared to the blood glucose level before administration of the derivative.
177. The derivative of any of embodiments 174-176 wherein the blood glucose is decreased by at least 35%, as compared to the blood glucose level before administration of the derivative.
178. The derivative of any of embodiments 174-177, wherein the blood glucose is decreased by at least 50%, as compared to the blood glucose level before administration of the derivative.
179. The derivative of any of embodiments 1-178, which has the effect in vivo of decreasing blood glucose after 72 hours, determined in a single-dose study in a db/db mouse model.
180. The derivative of any of embodiments 1-179, which has the effect in vivo of decreasing blood glucose after 96 hours, determined in a single-dose study in a db/db mouse model.
181. The derivative of embodiment 180, wherein the blood glucose is decreased by at least 5%, as compared to the blood glucose level before administration of the derivative.
182. The derivative of any of embodiments 180-181, wherein the blood glucose is decreased by at least 10%, as compared to the blood glucose level before administration of the derivative.
183. The derivative of any of embodiments 180-182, wherein the blood glucose is decreased by at least 15%, as compared to the blood glucose level before administration of the derivative.
184. The derivative of any of embodiments 180-183, wherein the blood glucose is decreased by at least 20%, as compared to the blood glucose level before administration of the derivative.
185. The derivative of any of embodiments 180-184, wherein the blood glucose is decreased by at least 25%, as compared to the blood glucose level before administration of the derivative.
186. The derivative of any of embodiments 1-185, which has the effect in vivo of decreasing body weight after 48 hours, determined in a single-dose study in a db/db mouse model.
187. The derivative of embodiment 186, wherein the body weight is decreased by at least 3%, as compared to the body weight before administration of the derivative.
188. The derivative of any of embodiments 186-187, wherein the body weight is decreased by at least 4%, as compared to the body weight before administration of the derivative.
189. The derivative of any of embodiments 186-188, wherein the body weight is decreased by at least 5%, as compared to the body weight before administration of the derivative.
190. The derivative of any of embodiments 186-184, wherein the body weight is decreased by at least 6%, as compared to the body weight before administration of the derivative.
191. The derivative of any of embodiments 1-190, which has the effect in vivo of decreasing body weight after 72 hours, determined in a single-dose study in a db/db mouse model.
192. The derivative of any of embodiments 1-191 which has the effect in vivo of decreasing body weight after 96 hours, determined in a single-dose study in a db/db mouse model.
193. The derivative of embodiment 192, wherein the body weight is decreased by at least 2%, as compared to the body weight before administration of the derivative.
194. The derivative of any of embodiments 192-193, wherein the body weight is decreased by at least 3%, as compared to the body weight before administration of the derivative.
195. The derivative of any of embodiments 192-194, wherein the body weight is decreased by at least 4%, as compared to the body weight before administration of the derivative.
196. The derivative of embodiment 168, wherein the animal model is pig.
197. The derivative of embodiment 196, wherein the animal model is LYD pig.
198. The derivative of any of embodiments 196-197, wherein the reduction in food intake is determined in an in vivo pharmacodynamic (PD) study.
199. The derivative of any of embodiments 196-198, wherein the reduction in food intake is determined in vivo in pig using any suitable study protocol and methodology, e.g. as described in Example 13.
200. The derivative of any of embodiments 196-199, wherein the reduction in food intake is determined in vivo in pig using any suitable study protocol and methodology, essentially as described in Example 13.
201. The derivative of any of embodiments 1-200, which has the effect in vivo of reducing food intake during a first period of 24 hours (0-24 hours) after administration of a single dose of the derivative, wherein food intake is determined in a single-dose study in a LYD pig model.
202. The derivative of any of embodiments 1-201, which has the effect in vivo of reducing food intake during a second period of 24 hours (24-48 hours) after administration of a single dose of the derivative, wherein food intake is determined in a single-dose study in a LYD pig model.
203. The derivative of any of embodiments 1-202, which has the effect in vivo of reducing food intake during a third period of 24 hours (48-72 hours) after administration of a single dose of the derivative, wherein food intake is determined in a single-dose study in a LYD pig model.
204. The derivative of any of embodiments 1-203, which has the effect in vivo of reducing food intake during a fourth period of 24 hours (72-96 hours) after administration of a single dose of the derivative, wherein food intake is determined in a single-dose study in a LYD pig model.
205. A GLP-1 derivative selected from the following: Chem. 21, Chem. 22, Chem. 23, Chem. 24, Chem. 25, Chem. 26, Chem. 27, and Chem. 28; or a pharmaceutically acceptable salt, amide, or ester thereof.
206. A GLP-1 derivative selected from the chemical structures shown in any of Examples 1-8; or a pharmaceutically acceptable salt, amide, or ester thereof.

207. A GLP-1 derivative selected from the GLP-1 derivative names shown in any of Examples 1-8; or a pharmaceutically acceptable salt, amide, or ester thereof.

208. The derivative of any of embodiments 205-207, which is a derivative according to any of embodiments 1-204.

209. An intermediate product in the form of a GLP-1 analogue, which comprises the following amino acid changes when compared to GLP-1 (7-37) (SEQ ID NO: 1):
i) (8Aib, 22E, 26R, 27K, 34R, 38G, 39G, 40G, 41S, 42K);
ii) (8Aib, 22E, 26R, 31K, 34R, 38G, 39G, 40G, 41S, 42K);
iii) (8Aib, 22E, 26R, 34R, 38K, 39G, 40G, 41S, 42K); iv (8Aib, 22E, 23K, 26R, 34R, 38G, 39G, 40G, 41S, 42K); v) (8Aib, 22E, 26R, 34R, 36K, 38G, 39G, 40G, 41S, 42K); or
vi) (8Aib, 18K, 22E, 26R, 34R, 38G, 39G, 40G, 41S, 42K).

210. An intermediate product in the form of a GLP-1 analogue, selected from the following analogues of GLP-1 (7-37) (SEQ ID NO: 1):
i) (8Aib, 22E, 26R, 27K, 34R, 38G, 39G, 40G, 41S, 42K);
ii) (8Aib, 22E, 26R, 31K, 34R, 38G, 39G, 40G, 41S, 42K);
iii) (8Aib, 22E, 26R, 34R, 38K, 39G, 40G, 41S, 42K); iv (8Aib, 22E, 23K, 26R, 34R, 38G, 39G, 40G, 41S, 42K); v) (8Aib, 22E, 26R, 34R, 36K, 38G, 39G, 40G, 41S, 42K); and
vi) (8Aib, 18K, 22E, 26R, 34R, 38G, 39G, 40G, 41S, 42K).

211. A pharmaceutical composition comprising a derivative according to any of embodiments 1-208, or an analogue according to any of embodiments 209-210, and a pharmaceutically acceptable excipient.

212. A derivative according to any of embodiments 1-208, or an analogue according to any of embodiments 209-210, for use as a medicament.

213. A derivative according to any of embodiments 1-208, or an analogue according to any of embodiments 209-210, for use in
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;
(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;
(iii) improving β-cell function, such as decreasing β-cell apoptosis, increasing β-cell function and/or β-cell mass, and/or for restoring glucose sensitivity to β-cells;
(iv) prevention and/or treatment of cognitive disorders and/or neurodegenerative disorders, such as Alzheimer's disease, Parkinson's disease, and/or multiple sclerosis;
(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;
(vi) prevention and/or treatment of diabetic complications, such as angiopathy; neuropathy, including peripheral neuropathy; nephropathy; and/or retinopathy;
(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;
(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;
(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;
(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;
(xi) prevention and/or treatment of polycystic ovary syndrome (PCOS);
(xii) prevention and/or treatment of cerebral disease, such as cerebral ischemia, cerebral haemorrhage, and/or traumatic brain injury;
(xiii) prevention and/or treatment of sleep apnoea; and/or
(xiv) prevention and/or treatment of abuse, such as alcohol abuse and/or drug abuse.

214. Use of a derivative according to any of embodiments 1-208, or an analogue according to any of embodiments 209-210, in the manufacture of a medicament for
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;
(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;
(iii) improving β-cell function, such as decreasing β-cell apoptosis, increasing β-cell function and/or β-cell mass, and/or for restoring glucose sensitivity to β-cells;
(iv) prevention and/or treatment of cognitive disorders and/or neurodegenerative disorders, such as Alzheimer's disease, Parkinson's disease, and/or multiple sclerosis;
(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

215. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative according to any of embodiments 1-208, or an analogue according to any of embodiments 209-210, is administered.

The following is a further set of particular embodiments of the invention:

1. A derivative of a GLP-1 like peptide of formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$, Formula I:

wherein

Xaa$_7$ is L-histidine, (S)-2-Hydroxy-3-(1H-imidazol-4-yl)-propionic acid, D-histidine, desamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;

Xaa$_8$ is Ala, Gly, Ser, Aib, (1-aminocyclopropyl)carboxylic acid, or (1-aminocyclobutyl)carboxylic acid;

Xaa$_{12}$ is Phe or Leu;

Xaa$_{16}$ is Val or Leu;

Xaa$_{18}$ is Ser, Arg, Lys, Val, or Leu;

Xaa$_{19}$ is Tyr or Gln;

Xaa$_{20}$ is Leu or Met;

Xaa$_{22}$ is Gly or Glu;

Xaa$_{23}$ is Gln, Glu, Lys, or Arg;

Xaa$_{25}$ is Ala or Val;

Xaa$_{26}$ is Arg or Lys;

Xaa$_{27}$ is Glu, Lys, or Leu;

Xaa$_{30}$ is Ala, Glu, or Arg;

Xaa$_{31}$ is Trp, Lys, or His;

Xaa$_{33}$ is Val, Lys, or Arg;

Xaa$_{34}$ is Lys, Arg, His, Asn, or Gln;

Xaa$_{35}$ is Gly or Ala;

Xaa$_{36}$ is Arg, Lys, or Gly;

Xaa$_{37}$ is Gly or Pro;

Xaa$_{38}$ is Ser, Gly, Ala, Glu, Pro, or Lys;

Xaa$_{39}$ is Ser, Gly, Ala, Glu, or Pro;

Xaa$_{40}$ is Ser, Gly, Ala, Glu, or Pro;

Xaa$_{41}$ is Ser, Gly, Ala, Glu, or Pro; and

Xaa$_{42}$ is Lys;

with the proviso that at least one of Xaa$_{18}$, Xaa$_{23}$, Xaa$_{27}$, Xaa$_{31}$, Xaa$_{36}$, or Xaa$_{38}$ is Lys;

wherein

Lys at Xaa$_{42}$ is a first K residue, and a Lys at one of Xaa$_{18}$, Xaa$_{23}$, Xaa$_{27}$, Xaa$_{31}$, Xaa$_{36}$, or Xaa$_{38}$ is a second K residue;

which derivative comprises a first and a second protracting moiety connected to said first and second K residue, respectively, wherein the first and second protracting moiety is of formula Chem. 1:

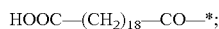

HOOC—(CH$_2$)$_{18}$—CO—*;  Chem. 1:

or a pharmaceutically acceptable salt, amide, or ester thereof.

2. The derivative of embodiment 1, wherein each of the first and the second protracting moiety is attached to the first and the second K residue, respectively, optionally via a first and a second linker, respectively.

3. The derivative of embodiment 2, wherein the first and the second linker each incorporates an *—NH group, and a *—CO group.

4. The derivative of any of embodiments 2-3, wherein each of the first and the second linker comprises an element_1 of formula Chem. 2:

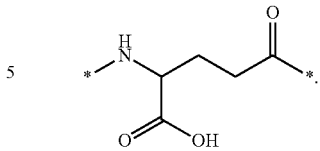

Chem. 2

5. The derivative of any of embodiments 1-4, wherein a Lys at Xaa$_{18}$ is the second K residue.

6. The derivative of any of embodiments 1-4, wherein a Lys at Xaa$_{23}$ is the second K residue.

7. The derivative of any of embodiments 1-4, wherein a Lys at Xaa$_{27}$ is the second K residue.

8. The derivative of any of embodiments 1-4, wherein a Lys at Xaa$_{31}$ is the second K residue.

9. The derivative of any of embodiments 1-4, wherein a Lys at Xaa$_{36}$ is the second K residue.

10. The derivative of any of embodiments 1-4, wherein a Lys at Xaa$_{38}$ is the second K residue.

11. A GLP-1 derivative selected from the following: Chem. 21, Chem. 22, Chem. 23, Chem. 24, Chem. 25, Chem. 26, Chem. 27, and Chem. 28; or a pharmaceutically acceptable salt, amide, or ester thereof.

12. An intermediate product in the form of a GLP-1 analogue, which comprises the following amino acid changes when compared to GLP-1 (7-37) (SEQ ID NO: 1):

i) (8Aib, 22E, 26R, 27K, 34R, 38G, 39G, 40G, 41S, 42K);
ii) (8Aib, 22E, 26R, 31K, 34R, 38G, 39G, 40G, 41S, 42K);
iii) (8Aib, 22E, 26R, 34R, 38K, 39G, 40G, 41S, 42K); iv) (8Aib, 22E, 23K, 26R, 34R, 38G, 39G, 40G, 41S, 42K); v) (8Aib, 22E, 26R, 34R, 36K, 38G, 39G, 40G, 41S, 42K); or
vi) (8Aib, 18K, 22E, 26R, 34R, 38G, 39G, 40G, 41S, 42K).

13. A pharmaceutical composition comprising a derivative according to any of embodiments 1-11, or an analogue according to embodiment 12, and a pharmaceutically acceptable excipient.

14. A derivative according to any of embodiments 1-11, or an analogue according to embodiment 12, for use as a medicament.

15. A derivative according to any of embodiments 1-11, or an analogue according to embodiment 12, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/ or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods). The examples serve to illustrate the invention.
Materials and Methods
List of Abbreviations
Aib: α-aminoisobutyric acid (2-Aminoisobutyric acid)
AcOH: acetic acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
Bzl: benzyl
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DesH: des-amino histidine (imidazopropionic acid or 3-(Imidazol-5-yl)propanoic acid), Imp)
DIC: diisopropylcarbodiimide
DIPEA: diisopropylethylamine
DMAP: 4-dimethylaminopyridine
DMEM: Dulbecco's Modified Eagle's Medium (DMEM)
DooaSuc: 8-amino-3,6-dioxaoctyl succinamic acid
EDTA: ethylenediaminetetraacetic acid
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexa fluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid or 3-(Imidazol-5-yl)propanoic acid) (also referred to as des-amino histidine, DesH)
Inp: isonipecotic acid
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NMP: N-methylpyrrolidone
OBz: benzoyl ester
OEG: 8-amino-3,6-dioxaoctanoic acid
OPfp: pentafluorophenoxy
OPnp: para-nitrophenoxy
OSu: O-succinimidyl esters (hydroxysuccinimide esters)
OtBu: tert butyl ester
Oxyma Pure®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
Pen/Strep: Penicllin/Streptomycin
PK: Pharmacokinetic
RP: Reverse Phase RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
TBME: tert-butyl methyl ether
tBu: tert. butyl
TFA: trifluoroacetic acid
TIS: triisopropylsilane
TLC: Thin Layer Chromatography
Tos: tosylate (or pare-toluenesulfonyl)
TotaGlyc: 13-amino-4,7,10-trioxamidecayl diglycolamic acid
Tris: tris(hydroxymethyl)aminomethane or 2-amino-2-hydroxymethyl-propane-1,3-diol
Trt: triphenylmethyl (trityl)
Trx: tranexamic acid
TtdSuc: 13-amino-4,7,10-trioxamidecayl succinamic acid
UPLC: Ultra Performance Liquid Chromatography
Special Materials
Eicosanedioic acid mono-tert-butyl ester
Docosanedioic acid mono-tert-butyl ester
Nonadecanedioic acid mono-tert-butyl esterNonadecanedioic acid
Fmoc-8-amino-3,6-dioxaoctanoic acid
Fmoc-8-amino-3,6-dioxaoctyl succinamic acid
Fmoc-13-amino-4,7,10-trioxamidecayl succinamic acid
Fmoc-13-amino-4,7,10-trioxamidecayl diglycolamic acid
Fmoc-tranexamic acid
Fmoc-Lys(Mtt)-OH
Fmoc-Glu-OtBu
Boc-Lys(Fmoc)-OH
4-Dimethylaminopyridine (DMAP)
tert-Butyl methyl ether (TBME)

The preparation of eicosanedioic acid mono-tert-butyl ester, docosanedioic acid mono-tert-butyl ester, and nonadecanedioic acid mono-tert-butyl ester is described in section 2 below, and the eleven last-mentioned materials are commercially available.

Chemical Methods

This section is divided in two: Section A relating to general methods (of preparation (A1); and of detection and characterisation (A2)), and section B, in which the preparation and characterisation of a number of specific example compounds is described.

A. General Methods

A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-isonipecotic acid, Fmoc-Glu-OtBu, Fmoc-Lys(Fmoc)-OH were used supplied from e.g. Anaspec, Bachem, Iris Biotech, or Novabiochem. Eicosanedioic acid mono-tert-butyl ester, docosanedioic acid mono-tert-butyl ester, and nonadecanedioic acid mono-tert-butyl ester can be prepared as described below. All operations stated below were performed at 250-µmol synthesis scale.

1. Synthesis of Resin Bound Protected Peptide Backbone
Method: SPPS_P

SPPS_P was performed on a Prelude Solid Phase Peptide Synthesizer from Protein Technologies (Tucson, Ariz. 85714 U.S.A.) at 250-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) at 250-µmol or 100-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

2. Synthesis of Albumin Binder

Eicosanedioic acid mono-tert-butyl ester can be prepared as is known in the art, e.g. as described in WO 2010102886 A1. Docosanedioic acid mono-tert-butyl ester can be prepared as described in the following:

1 M solution of borane-tetrahydrofuran complex in tetrahydrofuran (94.1 mL, 94.1 mmol) was added dropwise to a solution of icosanedioic acid mono-tert-butyl ester (25.0 g, 62.7 mmol) in dry tetrahydrofuran (140 mL) at 0 C under argon. The resulting solution was stirred at 0 C for 2 hrs, then the cooling bath was removed and the mixture stirred at room temperature overnight. Saturated aqueous solution of sodium bicarbonate (300 mL) and water (100 mL) were added and the resulting mixture was extracted with dichloromethane (250 mL, 2×100 mL). Combined organic extracts were dried over anhydrous sodium sulfate and evaporated to dryness. The residue was purified by column chromatography on silicagel (eluent: dichloromethane/methanol 99:1). Fractions with pure product were evaporated, residue was chromatographed again (eluent: dichloromethane/methanol 99:1). Products were combined and dried in vacuo yielding 20-hydroxy-icosanoic acid tert-butyl ester as white solid.

Yield: 16.50 g (68%).

$^1$H NMR spectrum (300 MHz, CDCl$_3$, delta$_H$): 3.64 (t, J=6.6 Hz, 2H), 2.20 (t, J=7.5 Hz, 2H); 1.65-1.51 (m, 4H); 1.45 (s, 9H); 1.36-1.21 (m, 30H).

The above prepared alcohol (16.5 g, 42.9 mmol) was dissolved in dry dichloromethane (90 mL). Triethylamine (9.00 mL, 64.4 mmol) was added, reaction mixture was cooled to 0 C and mesyl chloride (4.00 mL, 51.5 mmol) was added dropwise. After 1 hr the reaction mixture was allowed to warm to room temperature and has been stirred overnight. Water (1.5 mL) was added and the mixture was stirred 30 minutes. Solvents were evaporated, ethyl acetate was added (200 mL) and the mixture was extracted with 1 M hydrochloric acid (2×100 mL), 5% solution of sodium carbonate (2×100 mL) and water (100 mL). After drying with anhydrous sodium sulfate, filtration and evaporation of solvents 20-methanesulfonyloxy-icosanoic acid tert-butyl ester was obtained as white solid.

Yield: 19.80 g (100%).

$^1$H NMR spectrum (300 MHz, CDCl$_3$, delta$_H$): 4.22 (t, J=6.6 Hz, 2H); 3.01 (s, 3H); 2.20 (t, J=7.5 Hz, 2H); 1.81-1.68 (m, 2H); 1.63-1.51 (m, 2H); 1.44 (s, 9H); 1.34-1.22 (m, 30H).

The above prepared mesylate (17.8 g, 38.5 mmol) was dissolved in acetone (250 mL) and lithium bromide (6.69 g, 77.0 mmol) was added and the reaction mixture was refluxed overnight. After cooling down solvent was evaporated, ethyl acetate (300 mL) was added and the mixture was extracted with 5% solution of sodium bicarbonate (3×170 mL). Combined organic extracts were dried over anhydrous sodium sulfate and evaporated. Product was dried in vacuo to yield 20-bromo-icosanoic acid tert-butyl ester as white solid.

Yield: 17.10 g (99%).

$^1$H NMR spectrum (300 MHz, CDCl$_3$, delta$_H$): 3.41 (t, J=6.9 Hz, 2H); 2.20 (t, J=7.4 Hz, 2H); 1.90-1.77 (m, 2H); 1.64-1.50 (m, 2H); 1.43 (s, 9H); 1.34-1.13 (m, 30H).

Sodium hydride (60% dispersion in mineral oil, 3.96 g, 99.0 mmol) was dissolved in N,N-dimethylformamide (100 mL) under nitrogen. Dimethyl malonate (22.6 mL, 198 mmol) was added and the reaction mixture was heated briefly at 100 C, then cooled to room temperature and the solution of above prepared 20-bromo-icosanoic acid tert-butyl ester (14.8 g, 33.0 mmol) in N,N-dimethylformamide (150 mL) was added. The reaction mixture was heated at 100 C for 4 hrs. After cooling to room temperature, ethyl acetate (150 mL) was added and the organic solution was washed with saturated aqueous ammonium chloride (3×100 mL) and brine (100 mL), dried over anhydrous sodium sulfate and evaporated to dryness. Residue was purified by column chromatography on silicagel (eluent: hexane/ethyl acetate 96:4 to 93:7) giving 2-methoxycarbonyl-docosanedioic acid 22-tert-butyl ester 1-methyl ester as white solid.

Yield: 16.10 g (97%).

$^1$H NMR spectrum (300 MHz, CDCl$_3$, delta$_H$): 3.74 (s, 6H); 3.36 (t, J=7.5 Hz, 1H); 2.20 (t, J=7.5 Hz, 2H); 1.95-1.84 (m, 2H); 1.64-1.51 (m, 2H); 1.44 (s, 9H); 1.34-1.21 (m, 32H).

The above prepared 2-methoxycarbonyl-docosanedioic acid 22-tert-butyl ester 1-methyl ester (16.1 g, 32.3 mmol) was dissolved in tetrahydrofuran (85 mL) and solution of lithium hydroxide monohydrate (4.07 g, 96.9 mmol) in water (75 mL) was added. The reaction mixture was stirred at room temperature overnight, then it was acidified with 1 M hydrochloric acid and extracted with ethyl acetate (4×150 mL). Organic extracts were combined, dried over anhydrous sodium sulfate and evaporated. Product was dried in vacuo to yield 2-carboxy-docosanedioic acid 22-tert-butyl ester as white solid.

Yield: 14.50 g (95%).

$^1$H NMR spectrum (300 MHz, CDCl$_3$, delta$_H$): 3.44 (t, J=7.4 Hz, 1H); 2.22 (t, J=7.5 Hz, 2H); 2.00-1.89 (m, 2H); 1.63-1.52 (m, 2H); 1.45 (s, 9H); 1.37-1.20 (m, 32H).

2-Carboxy-docosanedioic acid 22-tert-butyl ester (14.5 g, 30.8 mmol) was dissolved in toluene (170 mL) and refluxed at 110 C for 48 hrs. Solvent was evaporated, residue was purified by column chromatography on silicagel (eluent: dichloromethane/methanol 97:3) giving the titled compound as white solid.

Yield: 5.25 g (40%).

Total yield: 5.25 g (25%)

$^1$H NMR spectrum (300 MHz, CDCl$_3$, delta$_H$): 2.35 (t, J=7.5 Hz, 2H); 2.21 (t, J=7.5 Hz, 2H); 1.68-1.53 (m, 4H); 1.45 (s, 9H); 1.35-1.22 (m, 32H).

Nonadecanedioic acid mono-tert-butyl ester can be prepared as described in the following:

A suspension of nonadecanedioic acid (26.1 g, 79.5 mmol) in mixture of toluene (140 mL) and t-butanol (32 mL, 334.8 mmol, 4.4 eq.) was heated to reflux temperature (97° C.). The mixture became a clear yellow solution. DMAP (1.9 g, 15.2 mmol, 0.2 eq.) was added, followed by the dropwise addition of Boc$_2$O in toluene (75 mL) over 90 minutes. Heavy CO$_2$-evolution was observed. The mixture was stirred at reflux temperature overnight and concentrated to a white slurry. Cold toluene (200 mL) was added and the solids were removed via filtration, washed with toluene and dried in vacuo (45° C.) (6.2 g, starting material). The filtrate was concentrated (45° C.) and heptane (350 mL) was added to the oily residue. The white suspension was stirred for 1 hour at 0° C. and the solids were isolated via filtration. The buttery-like filter residue was dissolved in TBME and rinsed through the filter. The heptane filtrate and TBME filtrate were concentrated separately. Heptane residue (10 g) contained mostly di-ester (ca. 80%) and the TBME residue (13.3 g) contained mostly mono-ester (ca. 80%). The TBME residue was purified by flash chromatography (Silica: 500 g, eluent: CH$_2$Cl$_2$/IPA 98:2 to 97:3). The title compound was obtained as a white solid (10.3 g, 33%).

$^1$H NMR spectrum (300 MHz, CDCl$_3$, delta$_H$): 2.35 (t, J=7.6 Hz, 2H); 2.20 (t, J=7.6 Hz, 2H); 1.68-1.53 (m, 4H); 1.43 (s, 9H); 1.39-1.22 (m, 26H).

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

The N-ε-lysine protection group was removed as described above and the chemical modification of the lysine was performed by one or more automated steps on the Prelude peptide synthesiser using suitably protected building blocks as described above. Double couplings were performed as described in SPPS_P with 3 hours per coupling.

Method: SC_L

The N-ε-lysine protection group was removed as described above and the chemical modification of the lysine was performed by one or more automated steps on the Liberty peptide synthesiser using suitably protected building blocks as described above. Double couplings were performed as described in SPPS_L.

4. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 µm column, using acetonitrile/water/TFA. The fractions were analysed by a combination of UPLC, MALDI and LCMS methods, and the appropriate fractions were pooled and lyophilised.

If desired the peptide counter ion can be exchanged to sodium using methods known in the art. As an example approx. 2 g peptide was dissolved in 250 ml acetonitrile/water (50/50) and loaded onto a Waters X-Bridge C8, 5 µM, 50×250 mm column on a preparative RP-HPLC system. Following loading, the column was washed with water for 8 min at a flow rate of 60 ml/min and 0.01 N NaOH pH 11 at a flow rate of 60 ml/min for 2×8 min. The sodium salt of the peptide was eluted using an isocratic flow of water at 60 ml/min for 10 min followed by a linear gradient of 5% to 85% acetonitrile over 30 min.

Method: CP_M2

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a Kinetex C18, 5 µm column, eluting with a binary mixture of 0.09M diammoniumhydrogenphosphate in water/acetonitrile (90:10, pH 3.0) and acetonitrile/2-propanol/water (60:20:20). The peptide was then further purified by standard RP-HPLC on a C18, 5 µm column, using acetonitrile/water/TFA. The fractions were analysed by a combination of UPLC, MALDI and LCMS methods, and the appropriate fractions were pooled and lyophilised.

If desired the peptide counter ion can be exchanged to sodium using the methods known in the art. As an example approx. 2 g peptide was dissolved in 250 ml acetonitrile/water (50/50) and loaded onto a Waters X-Bridge C8, 5 µM, 50×250 mm column on a preparative RP-HPLC system. Following loading, the column was washed with water for 8 min at a flow rate of 60 ml/min and 0.01 N NaOH pH 11 at a flow rate of 60 ml/min for 2×8 min. The sodium salt of the peptide was eluted using an isocratic flow of water at 60 ml/min for 10 min followed by a linear gradient of 5% to 85% acetonitrile over 30 min.

A2. General Methods for Detection and Characterisation

1. LC-MS Methods

Method: LCMS01

LCMS01v1 was performed on a setup consisting of Waters Acquity UPLC system and LCT Premier XE mass spectrometer from Micromass. Eluents: A: 0.1% Formic acid in water; B: 0.1% Formic acid in acetonitrile. The analysis was performed at RT by injecting an appropriate volume of the sample (preferably 2-10 µl) onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES. Scan: 100-2000 amu (alternatively 500-2000 amu), step 0.1 amu.

2. UPLC Method

Method: UPLC02

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% H$_2$O, 0.05% TFA; B: 99.95% CH$_3$CN, 0.05% TFA. The following linear gradient was used: 95% A, 5% B to 95% A, 5% B over 16 minutes at a flow-rate of 0.40 ml/min.

3. MALDI-MS Method

Method: MALDI01v01

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

B. Preparation of Example Compounds

Example 1

N{Epsilon-27}-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Aib8,Glu22,Arg26,Lys27,Arg34]-GLP-1-(7-37)-peptidyl-Gly-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl] Lys Chem. 21
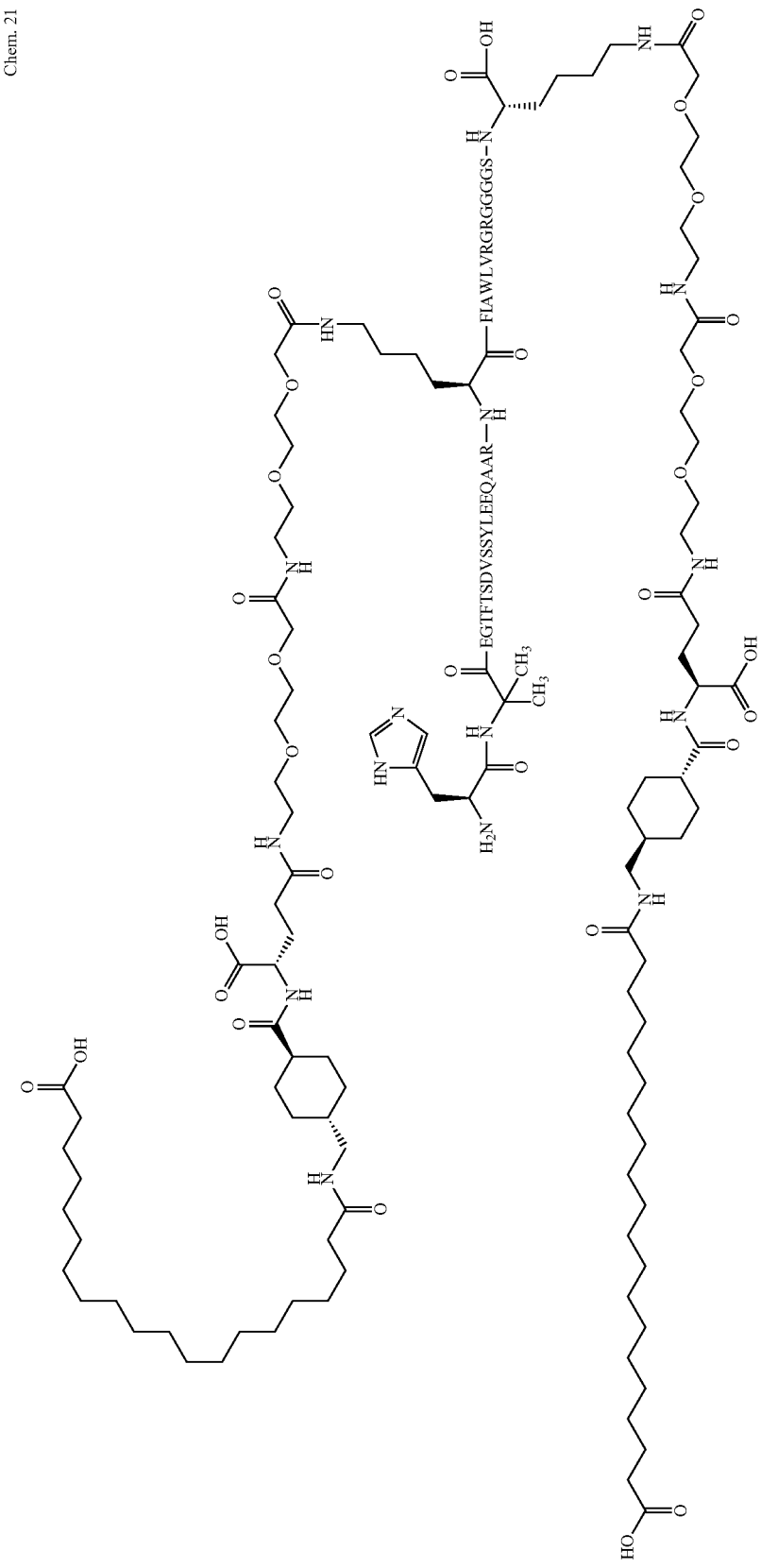

The peptide is SEQ ID NO: 2.
Synthesis method: SPPS_P; SC_P; CP_M1
UPLC02: Rt=10.6 min
MALDI01v01: calc. m/z=5649. found m/z=5648.

Example 2

N{Epsilon-31}-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl)-[Aib8,Glu22,Arg26,Lys31,Arg34]-GLP-1-(7-37)-peptidyl-Gly-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl] Lys Chem. 22
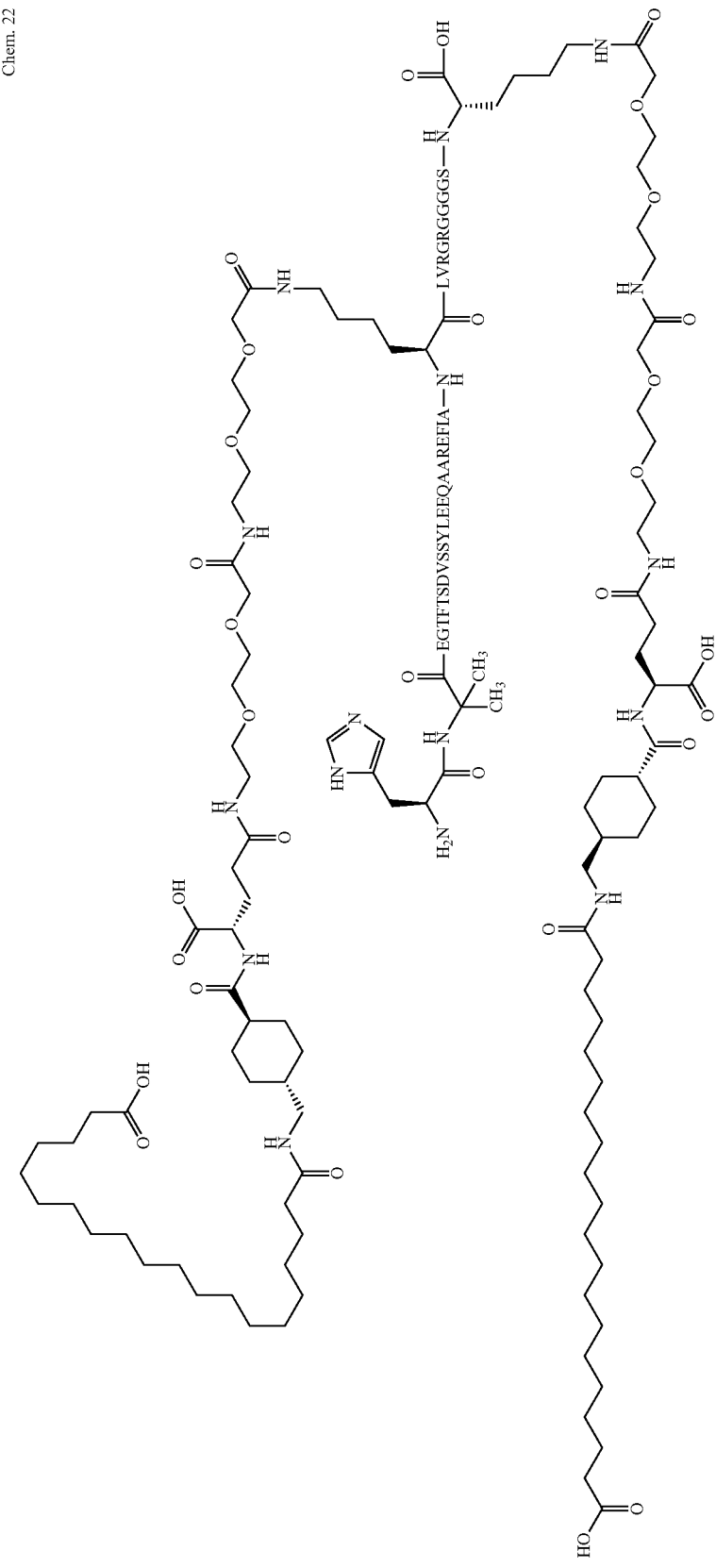

The peptide is SEQ ID NO: 3.
Synthesis method: SPPS_P; SC_P; CP_M1
UPLC02: Rt=10.6 min
MALDI01v01: calc. m/z=5593. found m/z=5590.

Example 3

N{Alpha}([Aib8,Glu22,Arg26,Arg34]-GLP-1-(7-37)-peptidyl)-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys Chem. 23
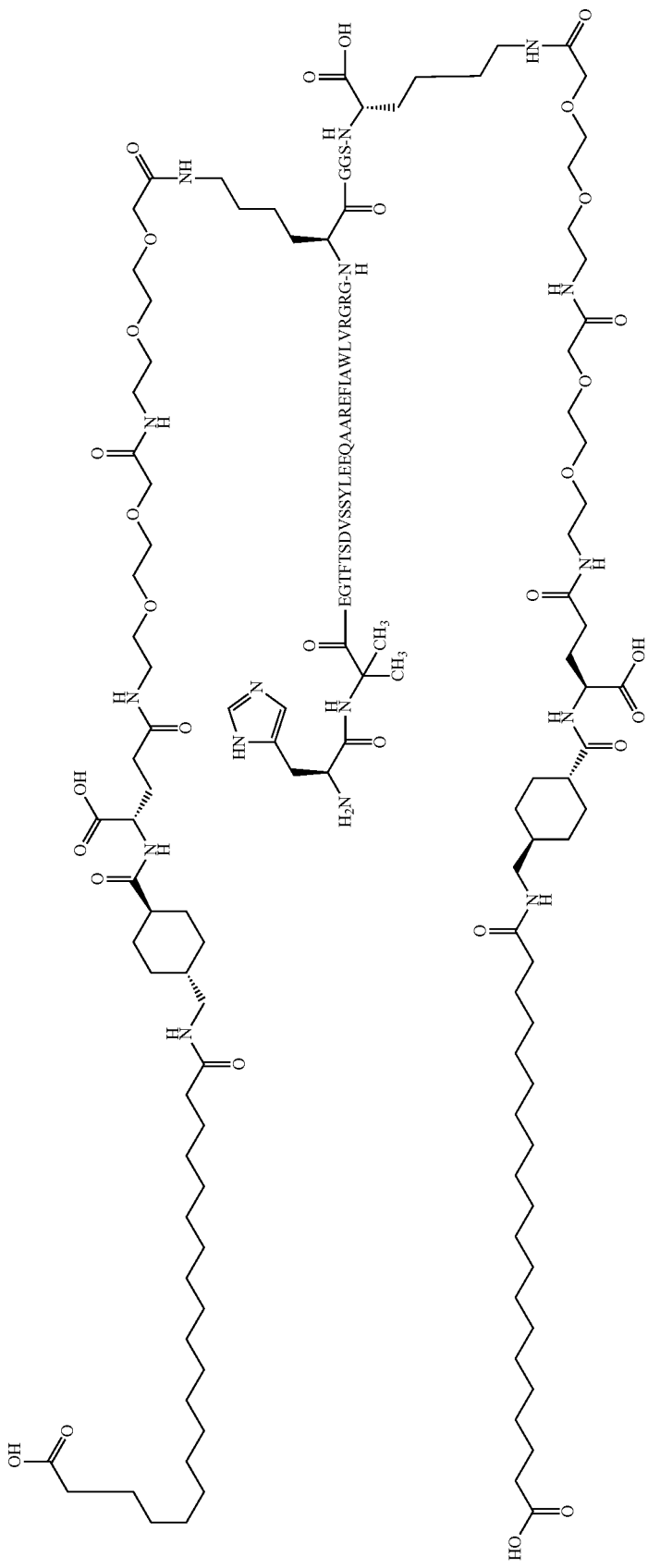

The peptide is SEQ ID NO: 4.
Synthesis method: SPPS_P; SC_P; CP_M1
UPLC02: Rt=10.8 min
MALDI01v01: calc. m/z=5722. found m/z=5720.

Example 4

N{Epsilon-23}-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Aib8,Glu22,Lys23,Arg26,Arg34]-GLP-1-(7-37)-peptidyl-Gly-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys

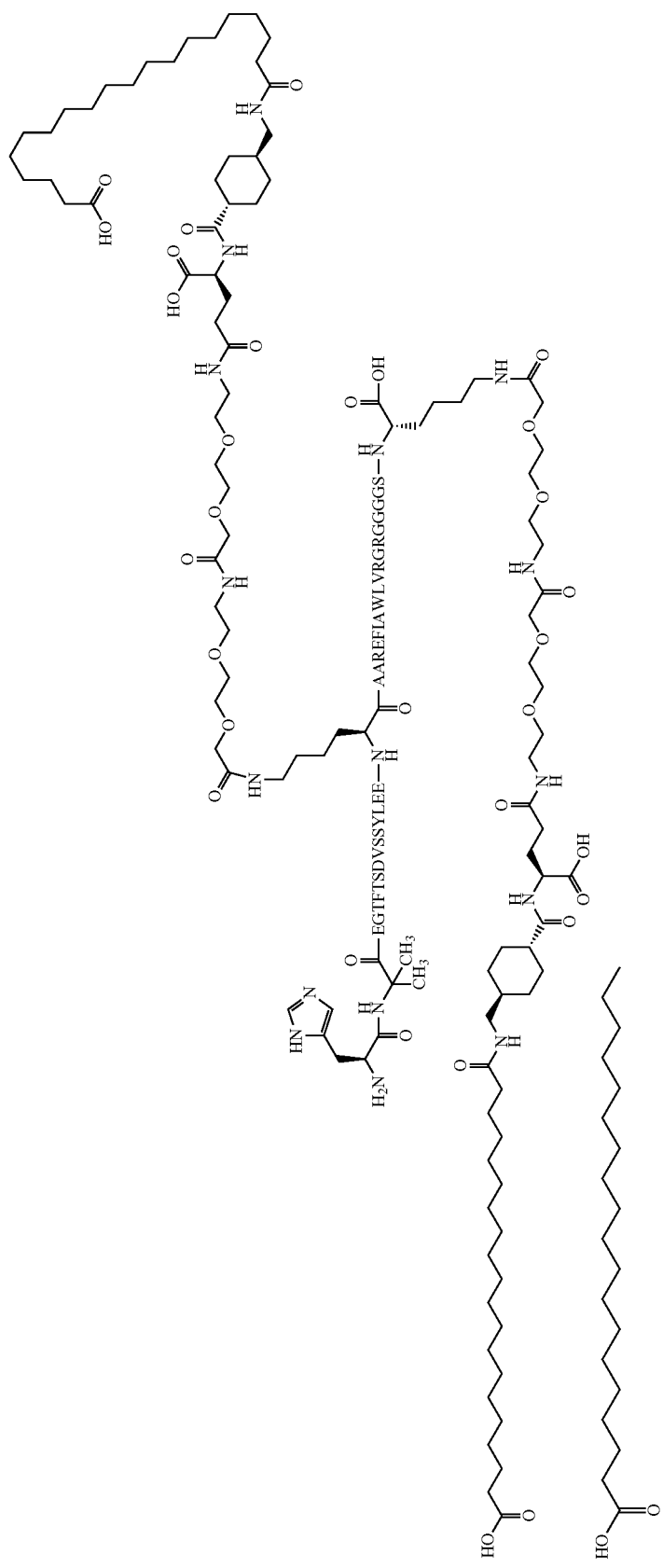

The peptide is SEQ ID NO: 5.
Synthesis method: SPPS_P; SC_P; CP_M1
UPLC02: Rt=10.6 min
MALDI01v01: calc. m/z=5651. found m/z=5649.

Example 5

N{Epsilon-36}-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Aib8,Glu22,Arg26,Arg34,Lys36]-GLP-1-(7-37)-peptidyl-Gly-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl] Lys Chem. 25
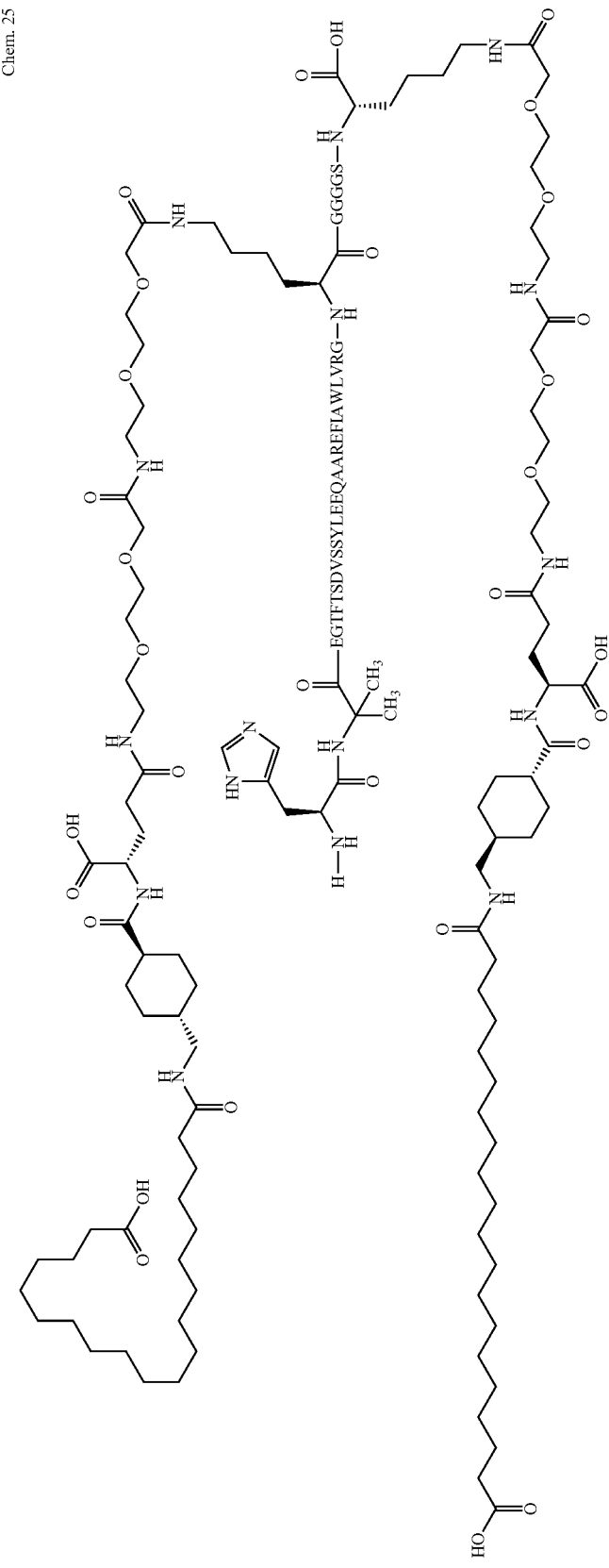

The peptide is SEQ ID NO: 6.
Synthesis method: SPPS_P; SC_P; CP_M1
UPLC02: Rt=11.3 min
MALDI01v01: calc. m/z=5623. found m/z=5621.

Example 6

N{Epsilon-18}-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Aib8,Lys18,Glu22,Arg26,Arg34]-GLP-1-(7-37)-peptidyl-Gly-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl] Lys

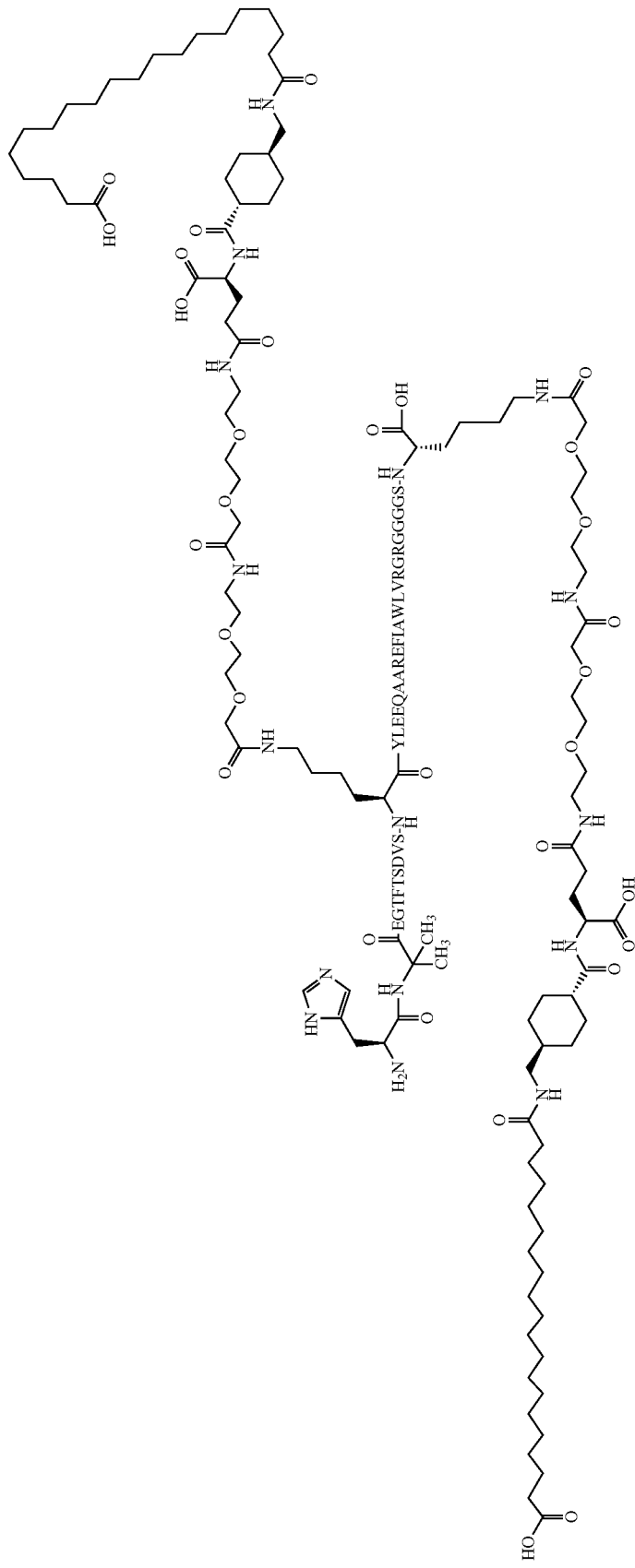

The peptide is SEQ ID NO: 7.
Synthesis method: SPPS_P; SC_P; CP_M1
UPLC02: Rt=10.8 min
LCMS01: Rt=2.6 min, m/3=1898; m/4=1424; m/3=1139

Example 7

N{Alpha}([Aib8,Glu22,Arg26,Arg34]-GLP-1-(7-37)-peptidyl)-N{Epsilon}[(2S)-2-amino-6-[[(2S)-2-amino-6-[[(4S)-4-carboxy-4-[[4-[(19-carboxynonadecanoylamino)methyl]cyclohexanecarbonyl]amino]butanoyl]amino]hexanoyl]amino]hexanoyl]Lys-Gly-Gly-Ser-N{Epsilon}[(2S)-2-amino-6-[[(2S)-2-amino-6-[[(4S)-4-carboxy-4-[[4-[(19-carboxynonadecanoylamino)methyl]cyclohexanecarbonyl]amino]butanoyl]amino]hexanoyl]amino]hexanoyl]Lys

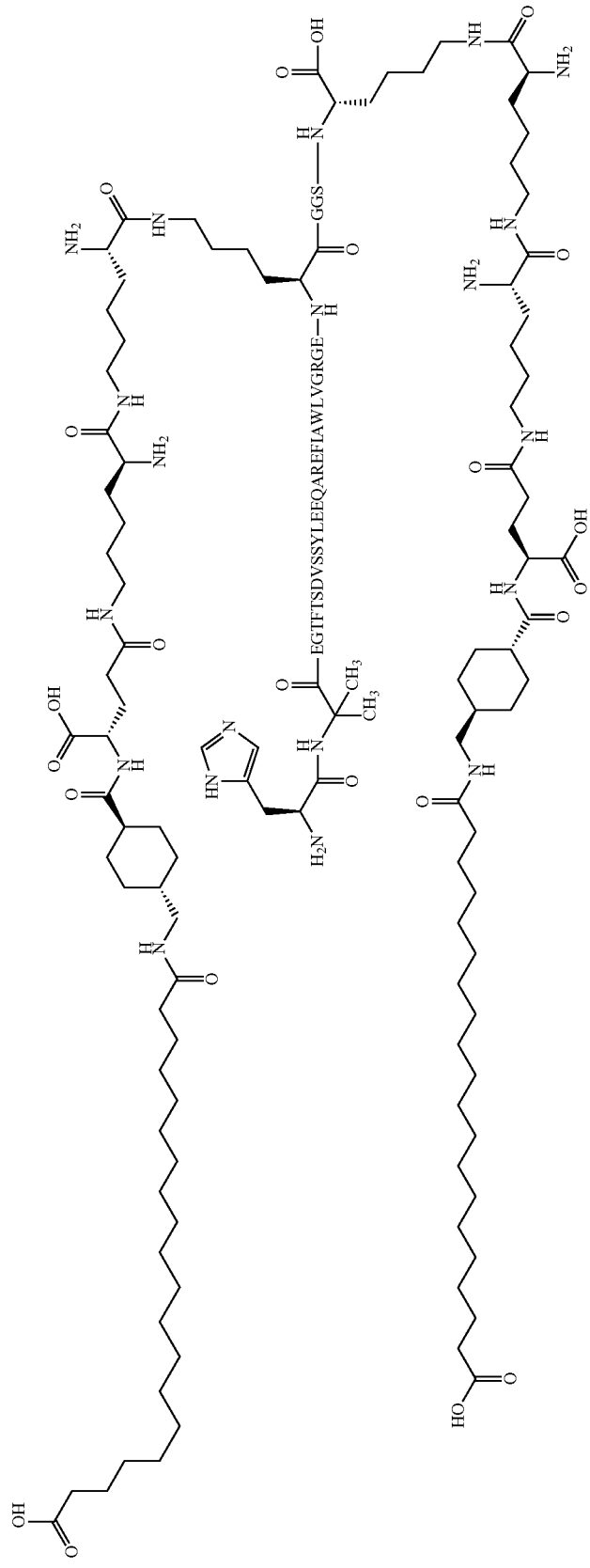

The peptide is SEQ ID NO: 4.
Synthesis method: SPPS_P; SC_P; CP_M1
UPLC02: Rt=9.8 min
LCMS01: Rt=2.3 min, m/3=1885; m/4=1415; m/5=1131; m/6=943

Example 8

N{Epsilon-27}-[(2S)-2-amino-6-[[(2S)-2-amino-6-[[(4S)-4-carboxy-4-(19-carboxynonadecanoylamino)butanoyl]amino]hexanoyl]amino]hexanoyl]-[Aib8,Glu22,Arg26,Lys27,Arg34]-GLP-1-(7-37)-peptidyl-Gly-Gly-Gly-Ser-N{Epsilon}R2S)-2-amino-6-[[(2S)-2-amino-6-[[(4S)-4-carboxy-4-(19-carboxynonadecanoylamino)butanoyl]amino]hexanoyl]amino]hexanoyl]Lys Chem. 28

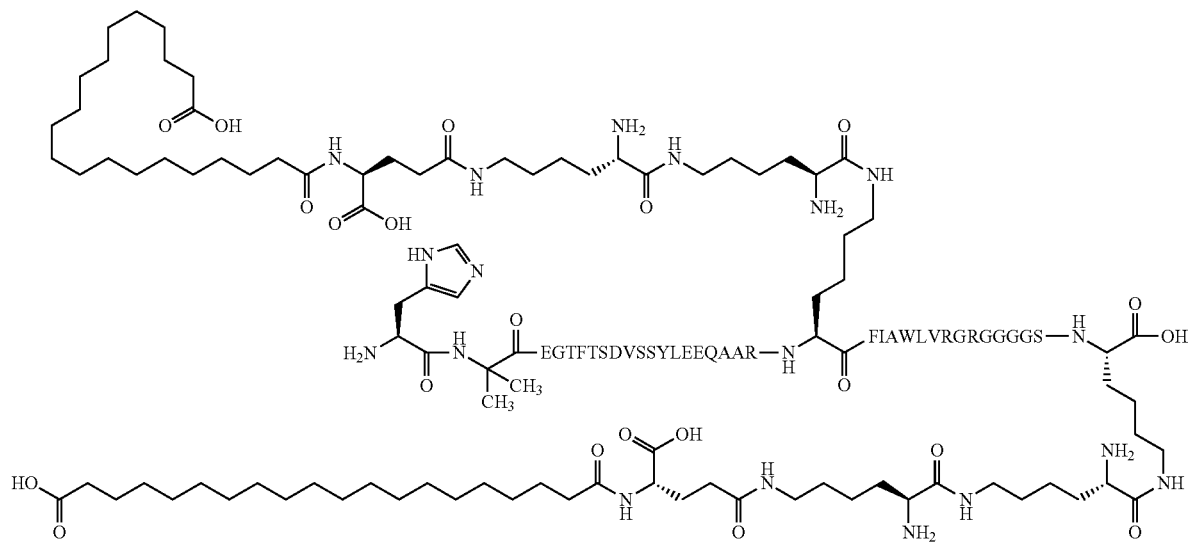

The peptide is SEQ ID NO: 2.
Synthesis method: SPPS_P; SC_P; CP_M1
UPLC02: Rt=8.9 min
MALDI01: calc. m/z=5303. found m/z=5302.

Example 9

N{Alpha}Aib8,Glu22,Arg26,Arg34]-GLP-1-(7-37)-peptidyl)-N{Epsilon}[2-[2-[2-[[2-[2-[2-[[(4S)-4-carboxy-4-[[4-[(21-carboxyhenicosanoylamino)methyl]cyclohexanecarbonyl]amino]butanoyl]amino]ethoxy]ethoxy]acetyl]amino]ethoxy]ethoxy]acetyl]Lys-Gly-Gly-Ser-N{Epsilon}[2-[2-[2-[[2-[2-[2-[[(4S)-4-carboxy-4-[[4-[(21-carboxyhenicosanoylamino)methyl]cyclohexanecarbonyl]amino]butanoyl]amino]ethoxy]ethoxy]acetyl]amino]ethoxy]ethoxy]acetyl]Lys

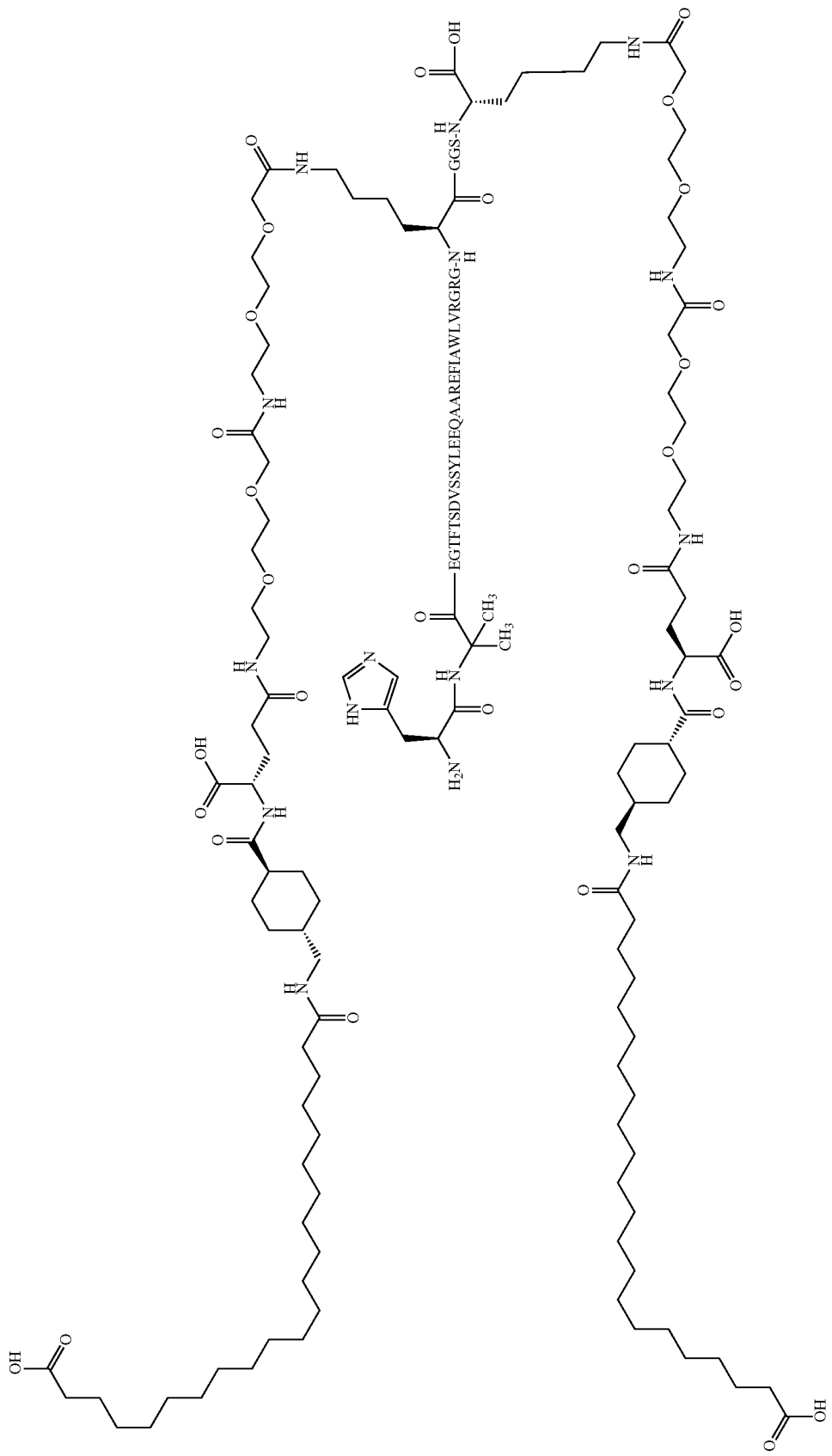
Chem. 29

The peptide is SEQ ID NO: 4.
Synthesis method: SPPS_P; SC_P; CP_M1
UPLC02: Rt=12.3 min
LCMS01: Rt=2.7; m/3=1927; m/4=1444; m/5=1156

Example 10

N{Alpha}([Aib8,Glu22,Arg26,Arg34]-GLP-1-(7-37)-peptidyl)-N{Epsilon}3-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]ethoxy]ethoxy]propanoylLys-Gly-Gly-Ser-N{Epsilon}3-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]ethoxy]ethoxy]propanoylLys

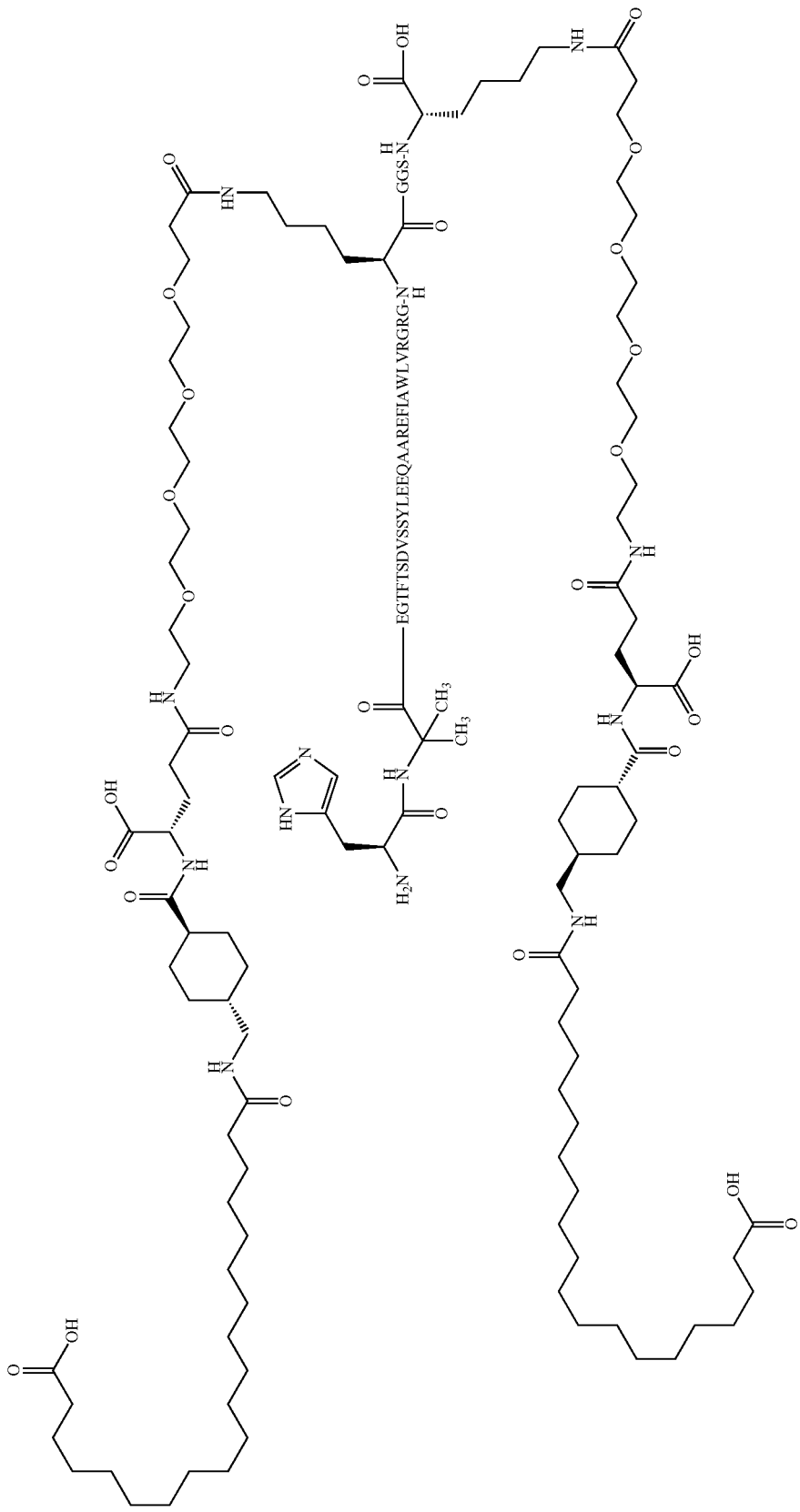
Chem. 30

The peptide is SEQ ID NO: 4.
Synthesis method: SPPS_P; SC_P; CP_M2
UPLC02: Rt=11.2 min
LCMS01: Rt=2.7; m/3=1880; m/4=1410; m/5=1128

Example 11

N{Alpha}([Aib8,Glu22,Arg26,Arg34]-GLP-1-(7-37)-peptidyl)-N{Epsilon}[2-[2-[2-[[2-[2-[2-[[(4S)-4-carboxy-4-[[4-[(19-carboxynonadecanoylamino) methyl]cyclohexanecarbonyl]amino]butanoyl] amino]ethoxy]ethoxy]acetyl]amino]ethoxy]ethoxy] acetyl]Lys-Ser-Pro-Glu-N{Epsilon}[2-[2-[2-[[2-[2-[2-[[(4S)-4-carboxy-4-[[4-[(19-carboxynonadecanoylamino)methyl] cyclohexanecarbonyl]amino]butanoyl]amino] ethoxy]ethoxy]acetyl]amino]ethoxy]ethoxy]acetyl] Lys Chem. 31
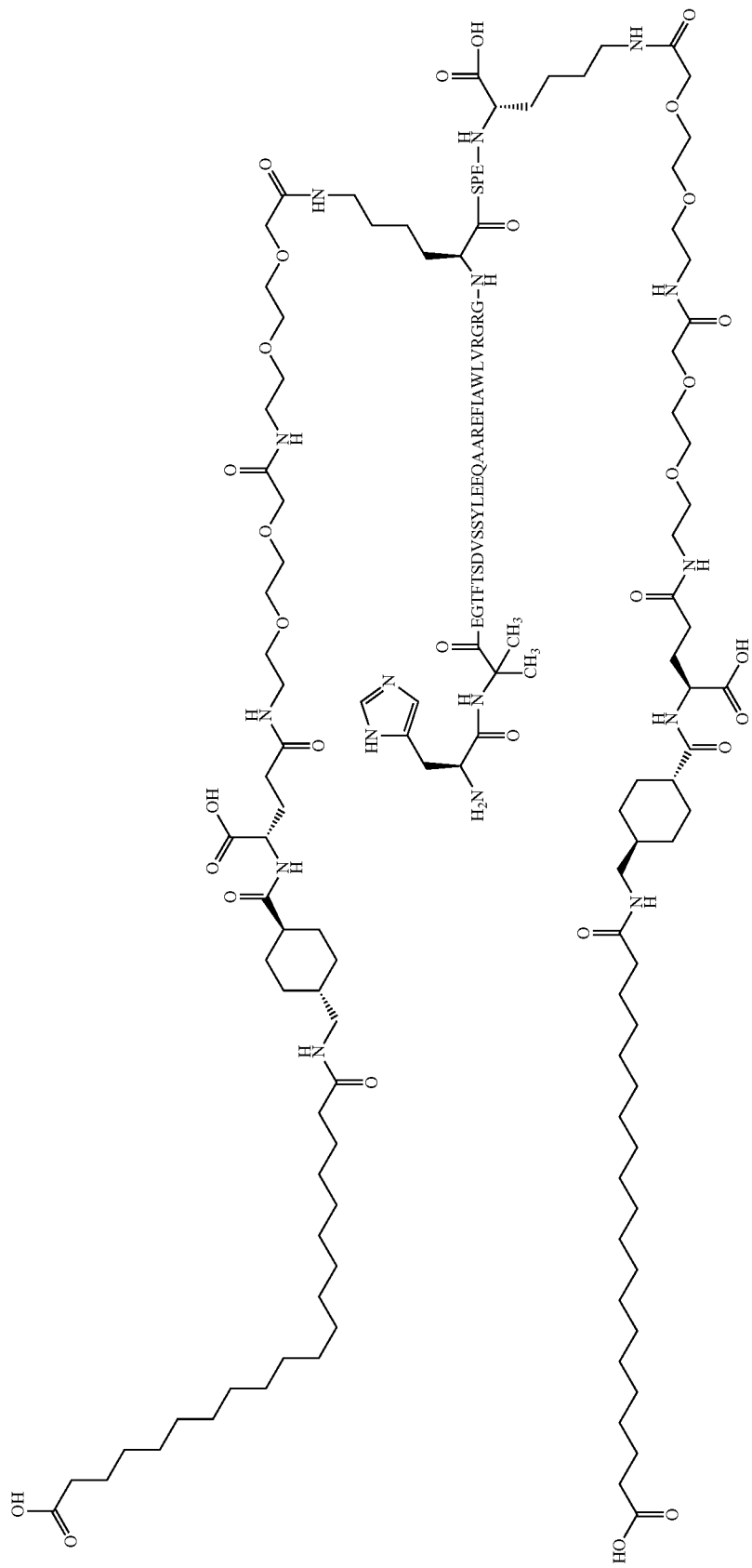

The peptide is SEQ ID NO: 14.
Synthesis method: SPPS_P; SC_P; CP_M1
UPLC02: Rt=11.7 min
LCMS01: Rt=2.7 min; m/3=1945; m/4=1460; m/5=1168

Example 12

N{Alpha}([Aib8,Glu22,Arg26,Arg34]-GLP-1-(7-37)-peptidyl)-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys-Pro-Glu-Gly-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys Chem. 32
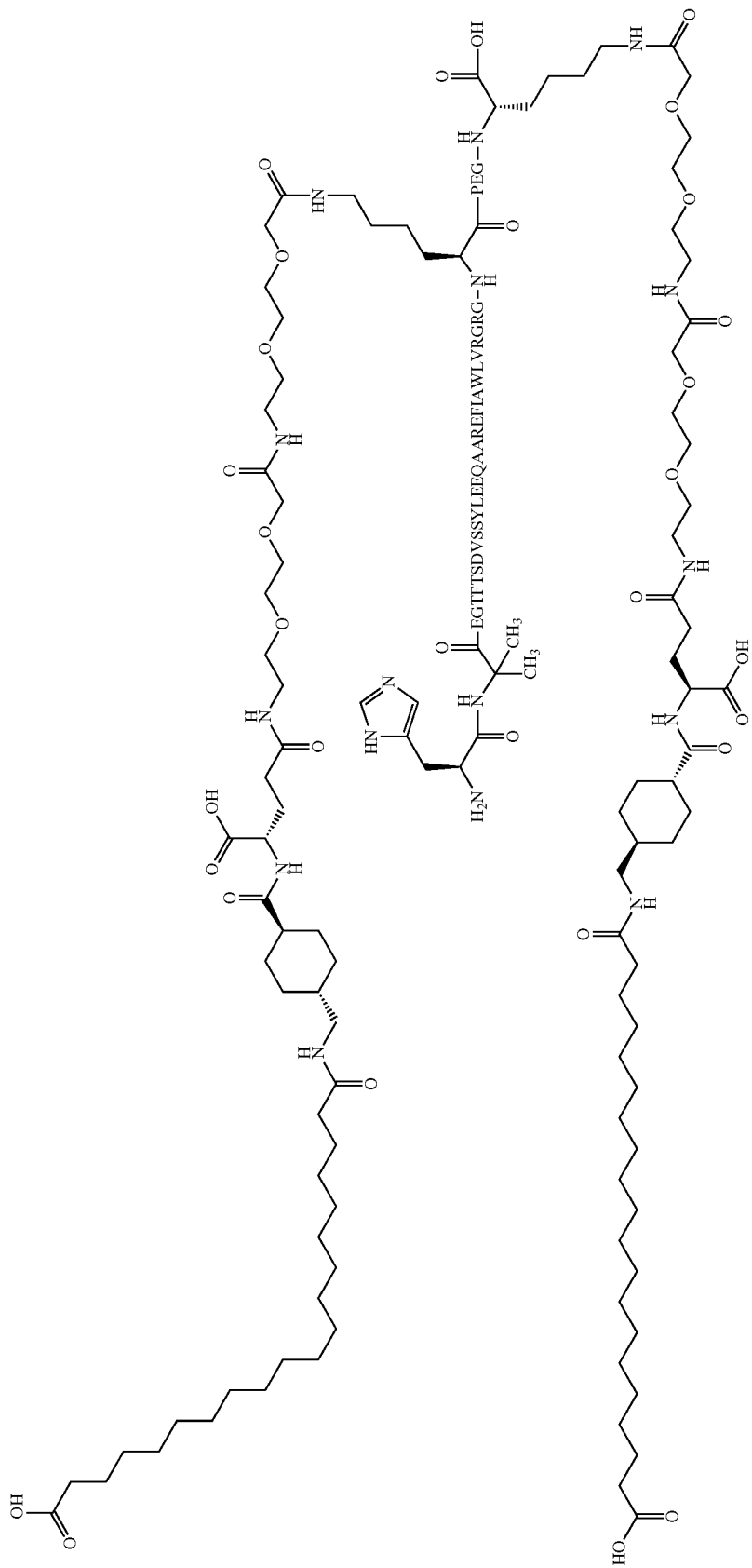

The peptide is SEQ ID NO: 12.
Synthesis method: SPPS_P; SC_P; CP_M1
UPLC02: Rt=11.8 min
LCMS01: Rt=2.7 min; m/3=1935 m/4=1452; m/5=1162

Example 13

N{Alpha}([Aib8,Glu22,Arg26,Arg34]-GLP-1-(7-37)-peptidyl)-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys-Ser-Ala-Glu-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys

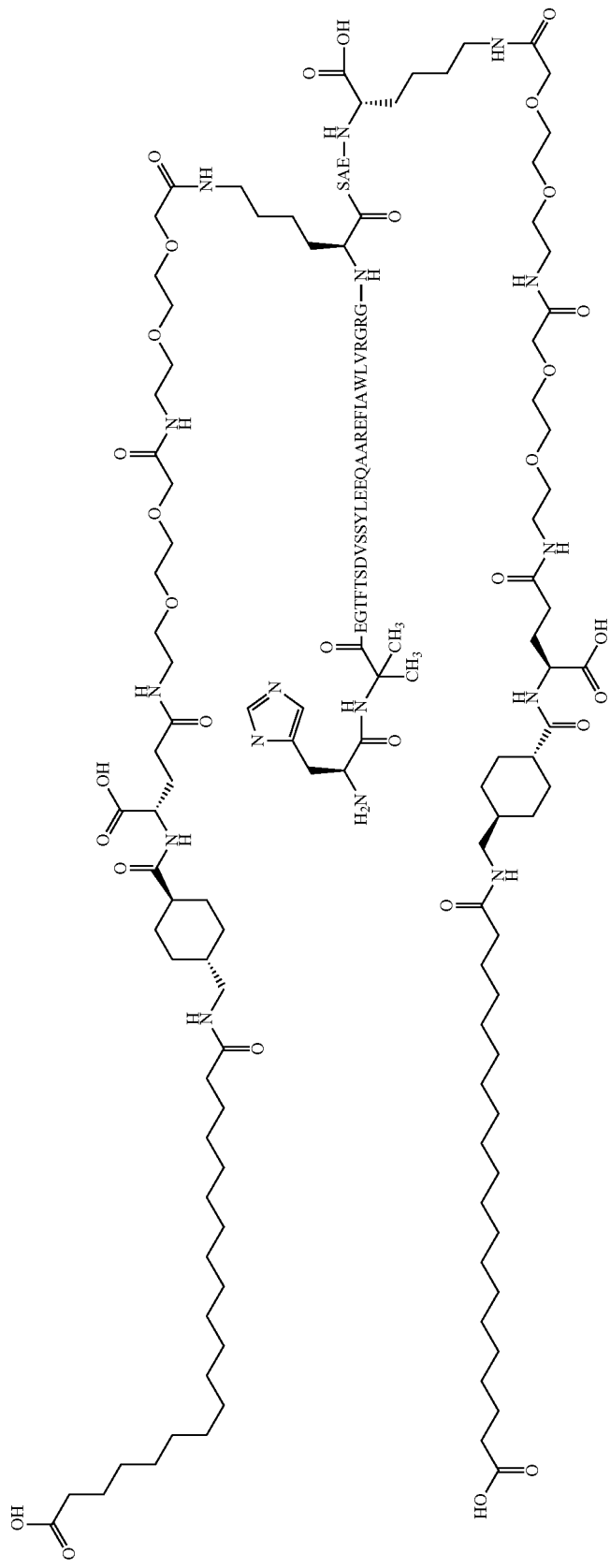
Chem. 33

The peptide is SEQ ID NO: 13.
Synthesis method: SPPS_P; SC_P; CP_M1
UPLC02: Rt=11.7 min
LCMS01: Rt=2.7 min; m/3=1937; m/4=1453; m/5=1162

Example 14

N{Epsilon-36}-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Aib8,Glu22,Arg26,Arg34,Lys36]-GLP-1-(7-37)-peptidyl-Ala-Glu-Ser-Pro-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys Chem. 34
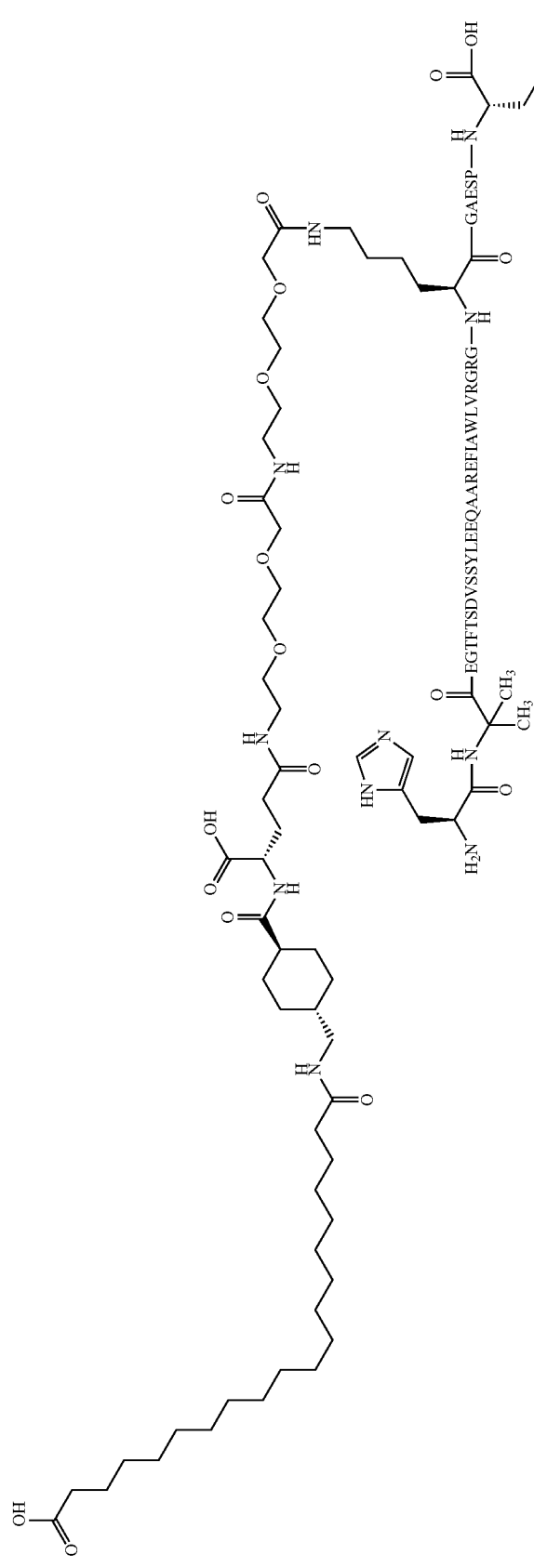
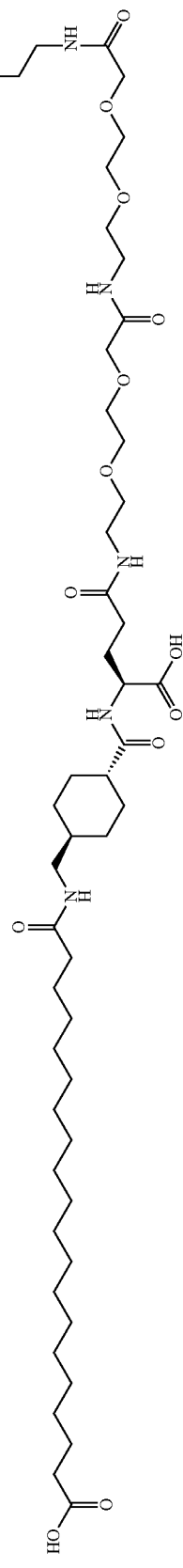

The peptide is SEQ ID NO: 9.
Synthesis method: SPPS_P; SC_P; CP_M1
UPLC02: Rt=12 min
LCMS01: Rt=2.8 min; m/3=1917; m/4=1438; m/5=1151

Example 15

N{Epsilon-36}-[2-[2-[2-[[2-[2-[2-[[(4S)-4-carboxy-
4-[[4-[(19-carboxynonadecanoylamino)methyl]cy-
clohexanecarbonyl]amino]butanoyl]amino]ethoxy]
ethoxy]acetyl]amino]ethoxy]ethoxy]acetyl]-[Aib8,
Glu22,Arg26,Arg34,Lys36]-GLP-1-(7-37)-peptidyl-
Pro-Ala-Ser-Glu-N{Epsilon}[2-[2-[2-[[2-[2-[2-
[[(4S)-4-carboxy-4-[[4-[(19-
carboxynonadecanoylamino)methyl]
cyclohexanecarbonyl]amino]butanoyl]amino]
ethoxy]ethoxy]acetyl]amino]ethoxy]ethoxy]acetyl]
Lys

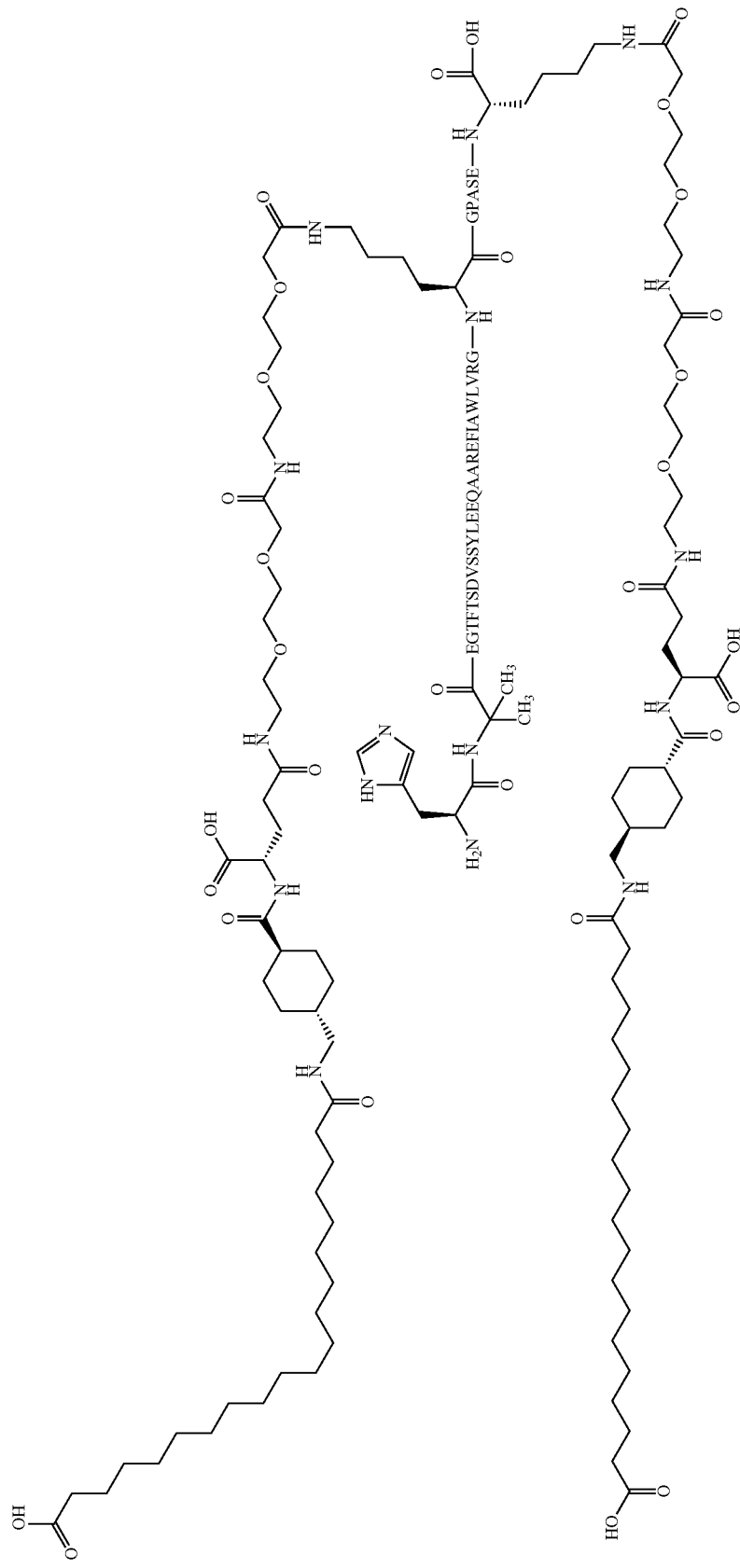
Chem. 35

The peptide is SEQ ID NO: 11.
Synthesis method: SPPS_P; SC_P; CP_M1
UPLC02: Rt=12 min
LCMS01: Rt=2.8 min; m/3=1917; m/4=1438; m/5=1151

Example 16

N{Epsilon-36}-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-[Aib8,Glu22,Arg26,Arg34,Lys36]-GLP-1-(7-37)-peptidyl-Glu-Gly-Pro-Ala-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl] Lys

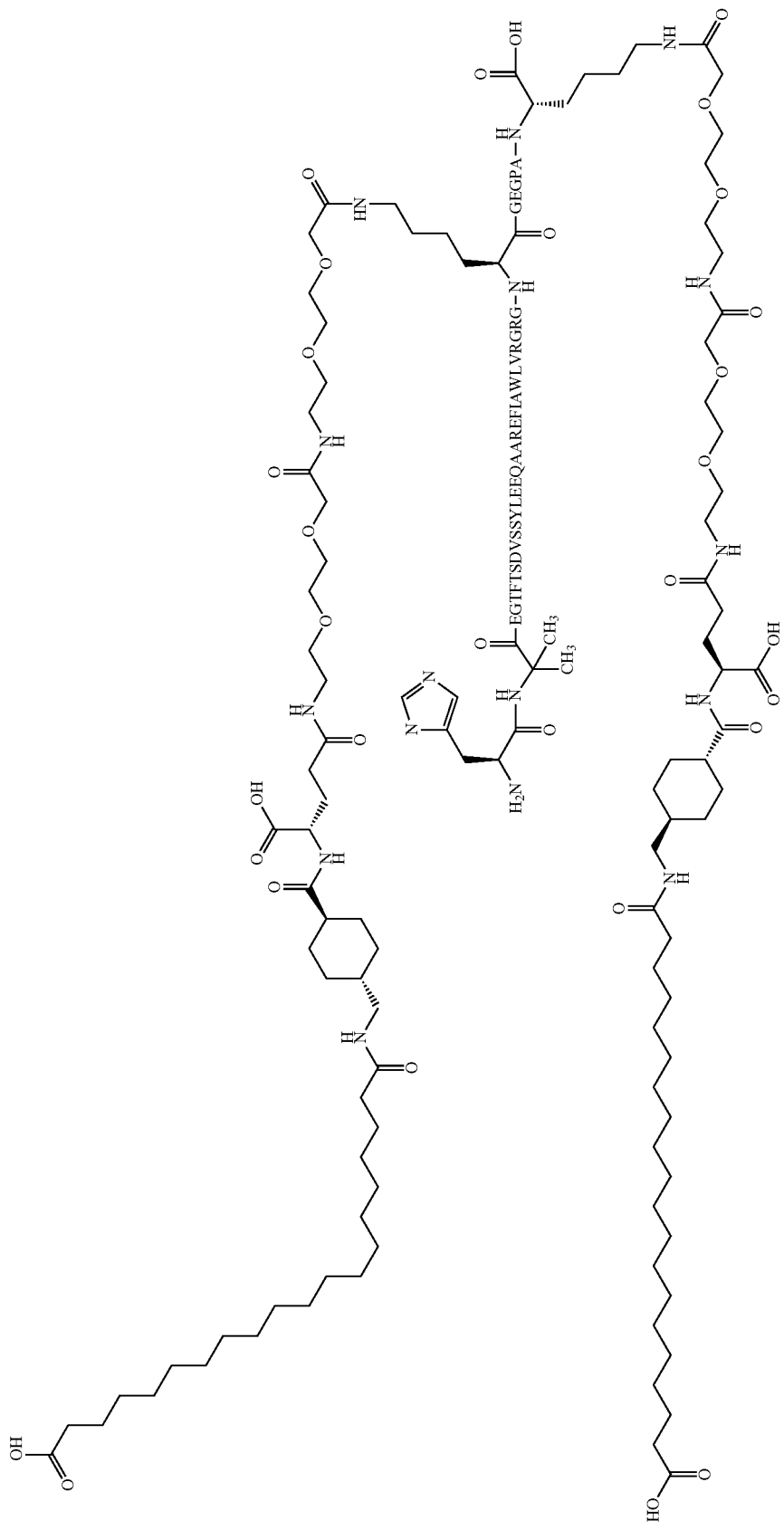

The peptide is SEQ ID NO: 10.
Synthesis method: SPPS_P; SC_P; CP_M1
UPLC02: Rt=12 min
LCMS01: Rt=2.8 min; m/3=1907; m/4=1431; m/5=1145

Example 17

N{Alpha}([Aib8,Glu22,Arg26,Arg34]-GLP-1-(7-37)-peptidyl)-N{Epsilon}[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]Lys-Gly-Gly-Ser-N{Epsilon}[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]Lys Chem. 37
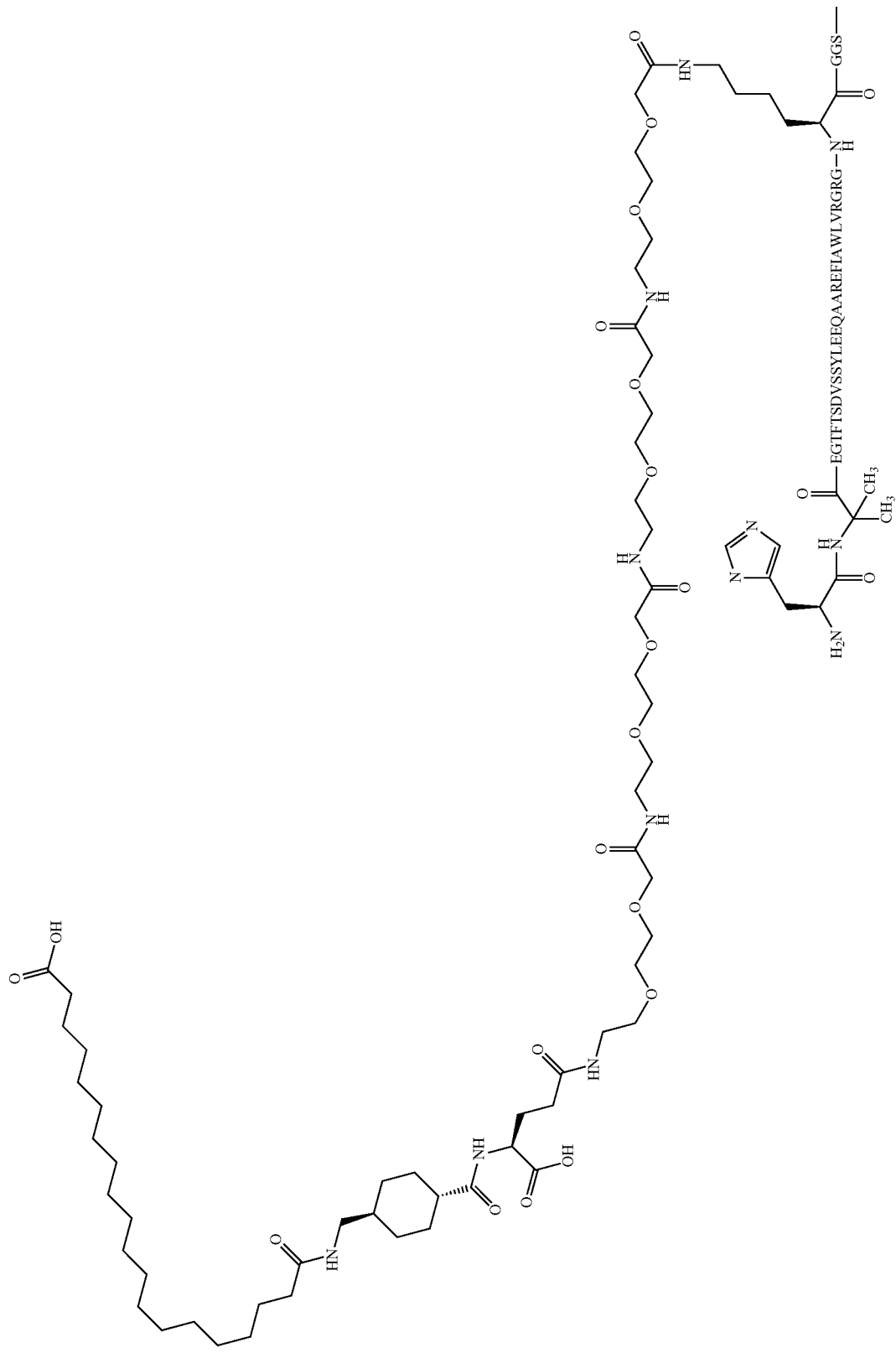

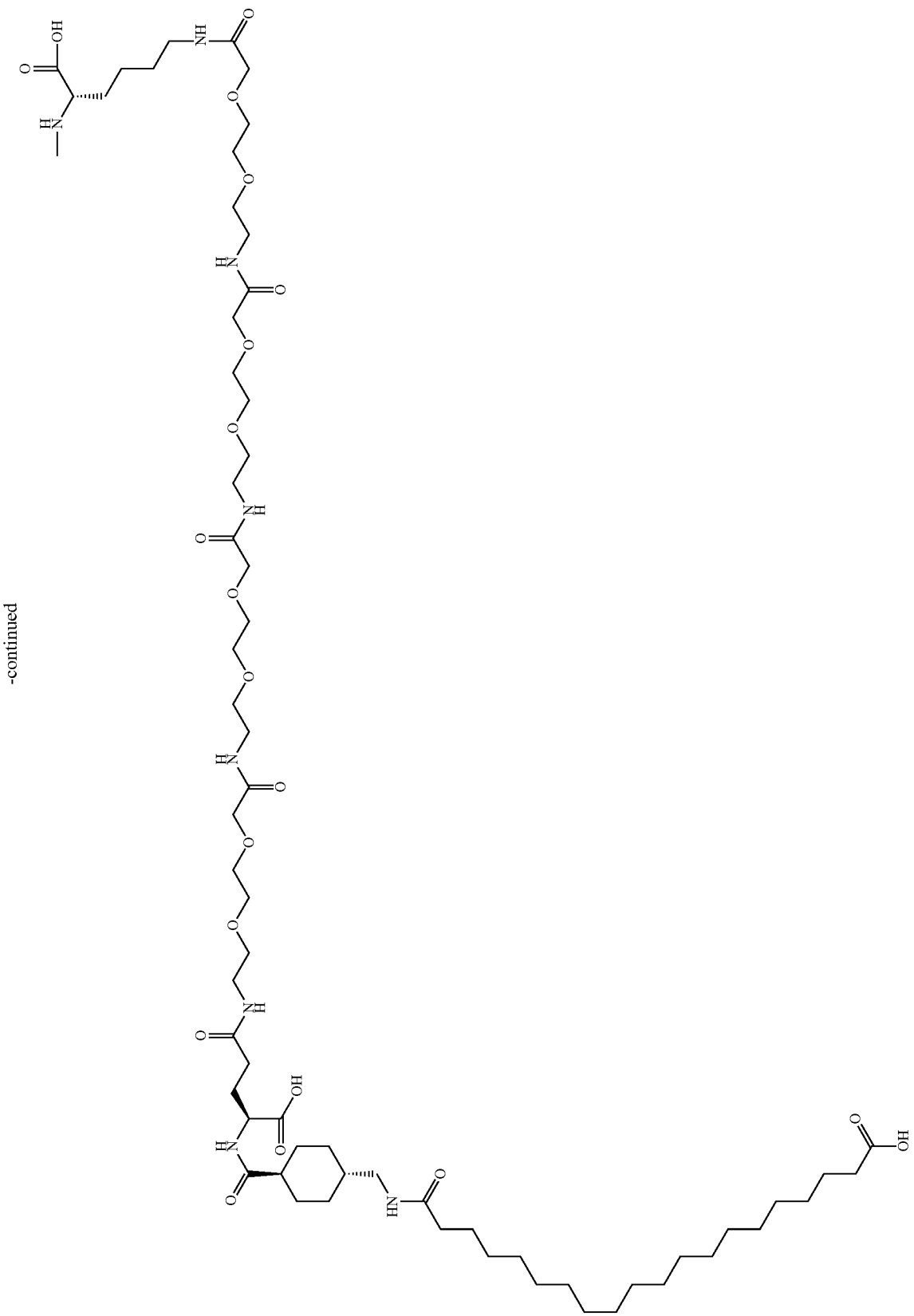

The peptide is SEQ ID NO: 4.
Synthesis method: SPPS_P; SC_P; CP_M1
UPLC02: Rt=11.3 min
LCMS01: Rt=2.7 min; m/4=1577; m/5=1262

Example 18

N{Alpha}([Imp 7,Aib8,Glu22,Arg26,Arg34]-GLP-1-(7-37)-peptidyl)-N{Epsilon}[2-[2-[2-[[2-[2-[2-[[2-[2-[2-[[2-[2-[2-[[(4S)-4-carboxy-4-[[4-[(19-carboxynonadecanoylamino)methyl] cyclohexanecarbonyl]amino]butanoyl]amino] ethoxy]ethoxy]acetyl]amino]ethoxy]ethoxy]acetyl]amino]ethoxy]ethoxy]acetyl]amino]ethoxy]ethoxy]acetyl]Lys-Gly-Gly-Ser-N{Epsilon}[2-[2-[2-[[2-[2-[2-[[2-[2-[2-[[2-[2-[2-[[(4S)-4-carboxy-4-[[4-[(19-carboxynonadecanoylamino)methyl] cyclohexanecarbonyl]amino]butanoyl]amino] ethoxy]ethoxy]acetyl]amino]ethoxy]ethoxy]acetyl]amino]ethoxy]ethoxy]acetyl]amino]ethoxy]ethoxy] acetyl]Lys Chem. 38
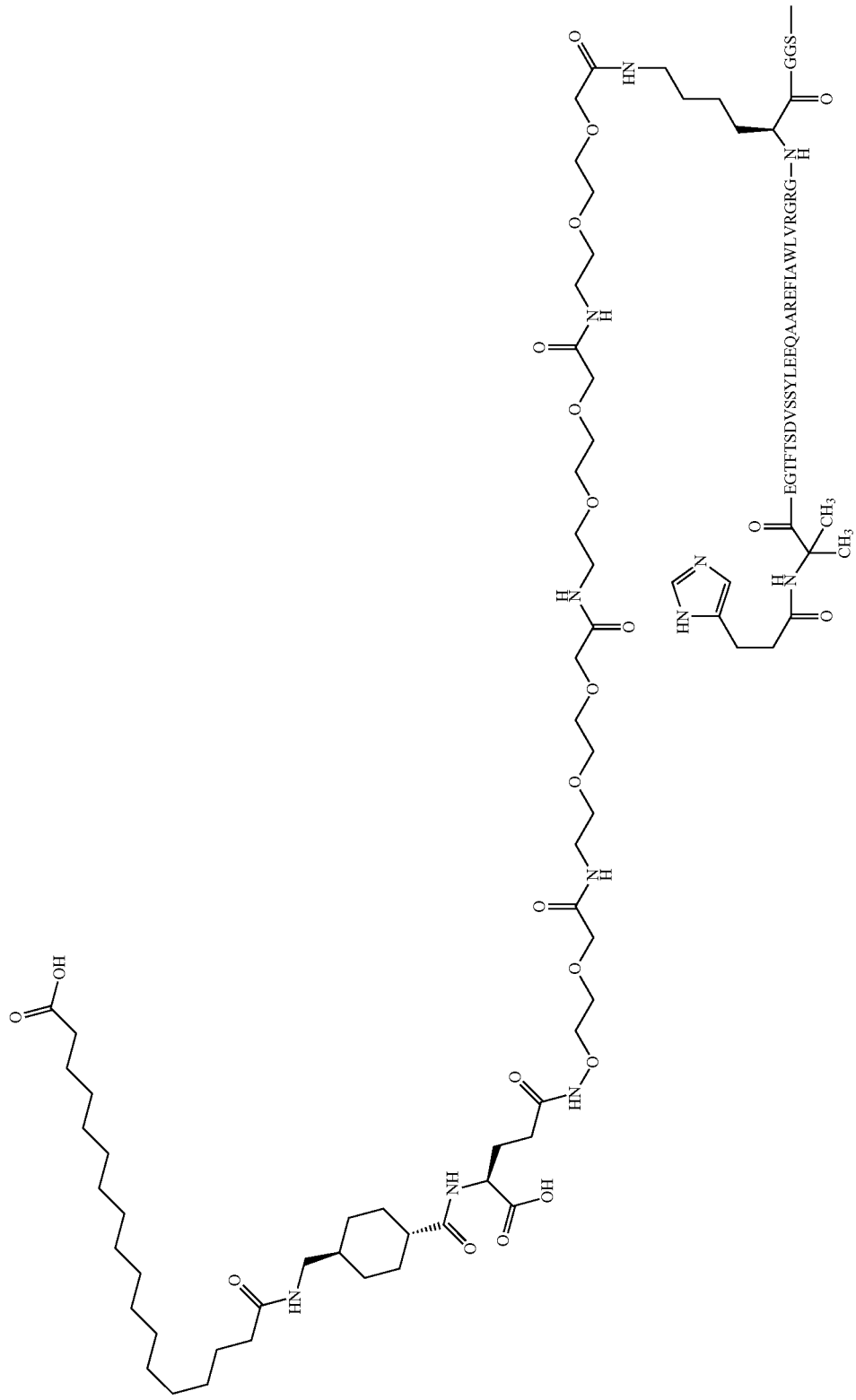

-continued
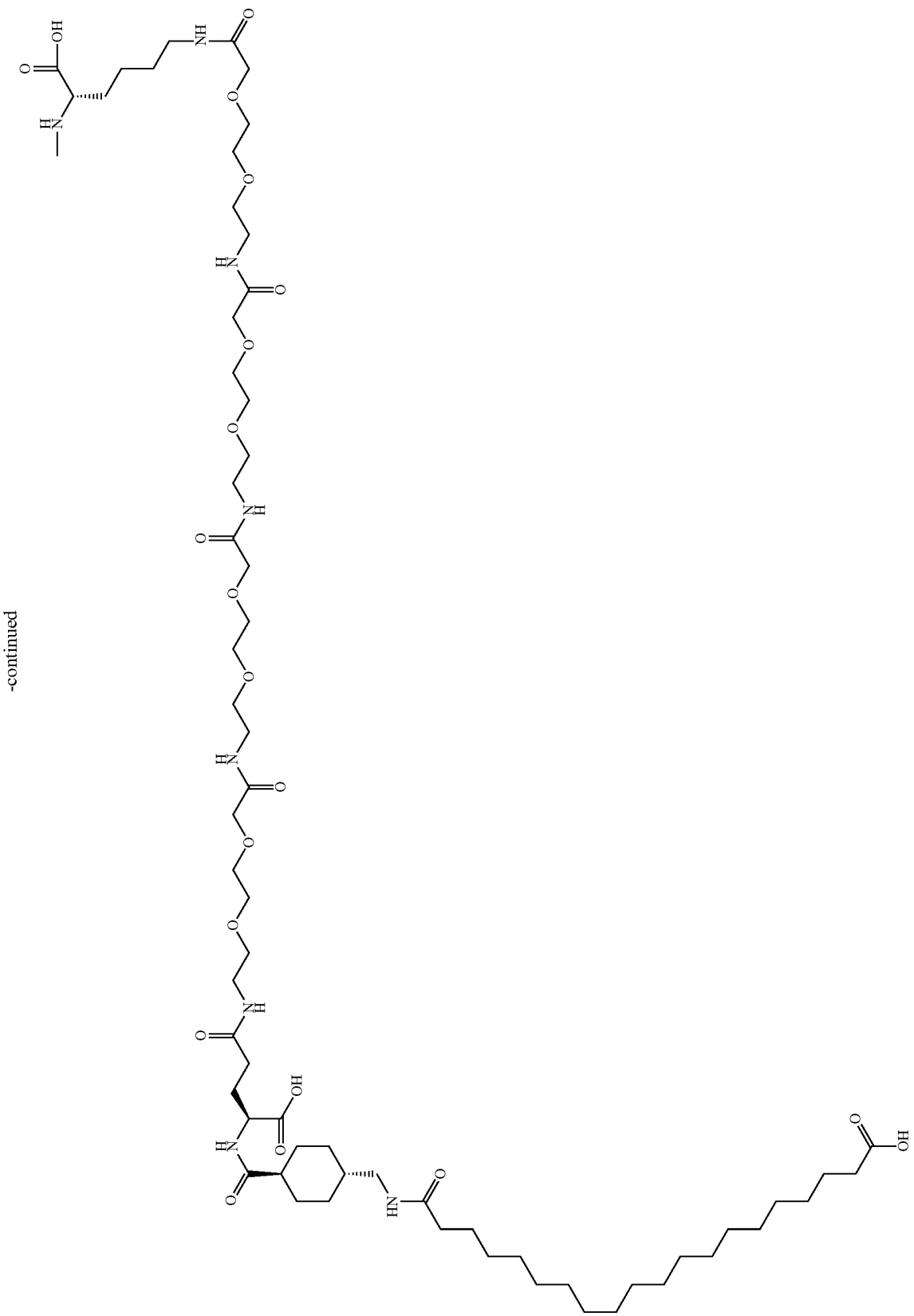

The peptide is SEQ ID NO: 8.
Synthesis method: SPPS_P; SC_P; CP_M1
UPLC02: Rt=11.5 min
LCMS01: Rt=2.7 min; m/4=1572; m/5=1258

Example 19

N{Alpha}([Aib8,Glu22,Arg26,Arg34]-GLP-1-(7-37)-peptidyl)-N{Epsilon}[2-[2-[2-[[2-[2-[2-[[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]Lys-Gly-Gly-Ser-N{Epsilon}[2-[2-[2-[[2-[2-[2-[[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]Lys Chem. 39

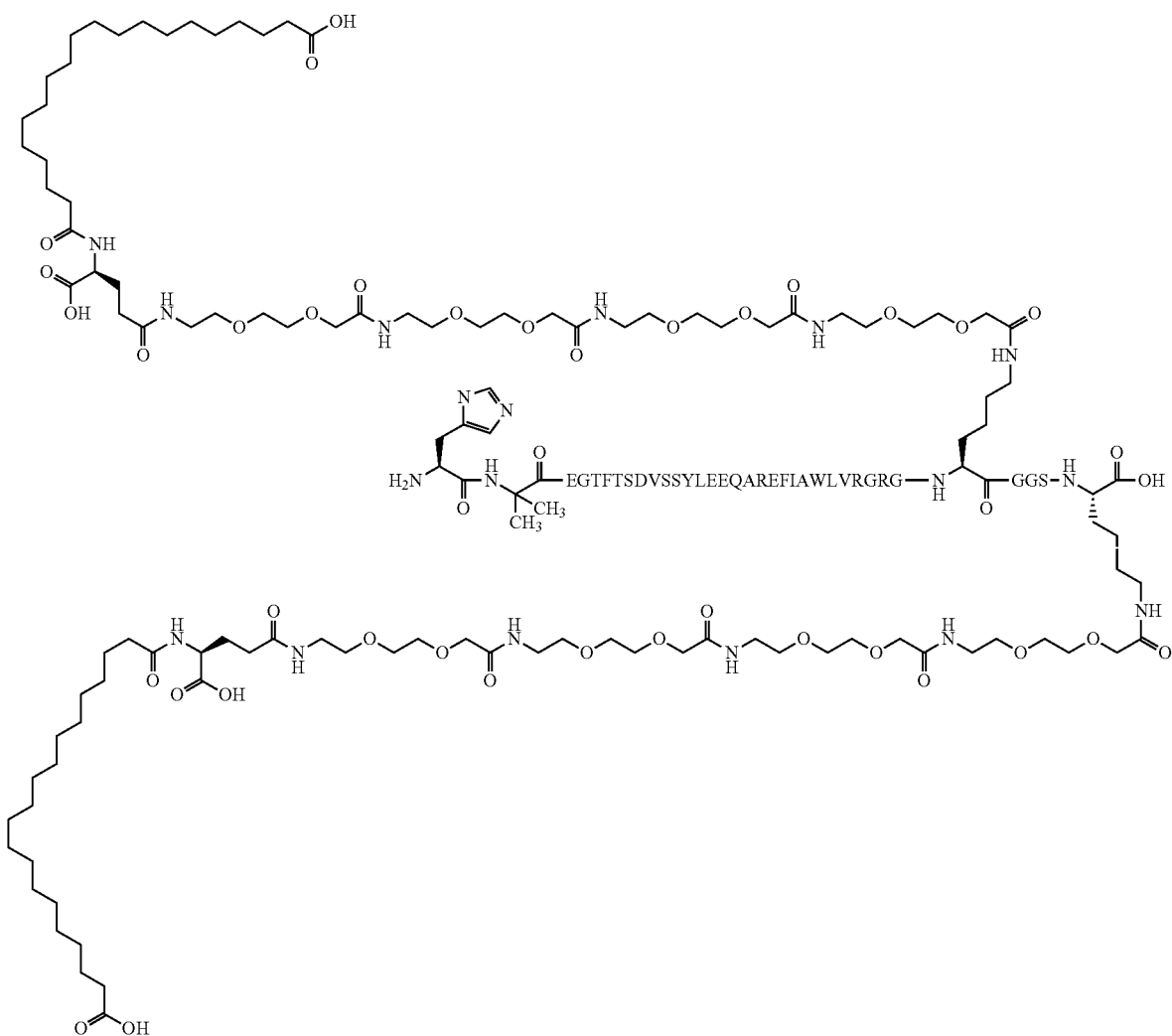

The peptide is SEQ ID NO: 4.
Synthesis method: SPPS_P; SC_P; CP_M1
UPLC02: Rt=10.7 min
LCMS01: Rt=2.6 min; m/4=1507; m/5=1206

Example 20
N{Alpha}([Imp 7,Aib8,Glu22,Arg26,Arg34]-GLP-1-(7-37)-peptidyl)-N{Epsilon}[2-[2-[2-[[2-[2-[2-[[2-[2-[2-[[2-[2-[[(4S)-4-carboxy-4-(19-carboxynon-adecanoylamino)butanoyl]amino]ethoxy]ethoxy]acetyl]amino]ethoxy]ethoxy]acetyl]amino]ethoxy]ethoxy]acetyl]Lys-Gly-Gly-Ser-N{Epsilon}[2-[2-[2-[[2-[2-[2-[[2-[2-[2-[[2-[2-[[(4S)-4-carboxy-4-(19-carboxynonadecanoylamino)butanoyl]amino]ethoxy]ethoxy]acetyl]amino]ethoxy]ethoxy]acetyl]amino]ethoxy]ethoxy]acetyl]Lys
Chem. 40
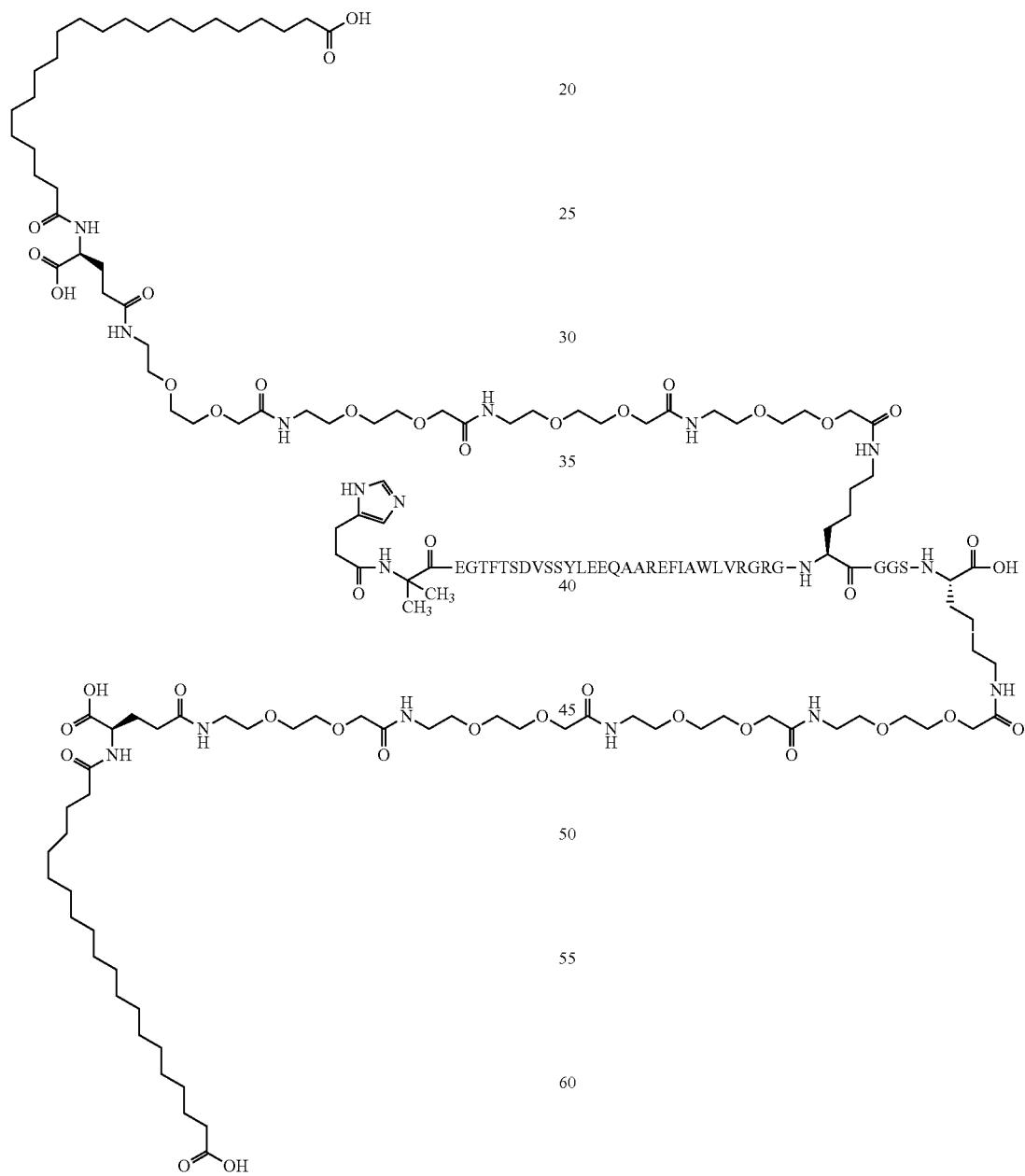

The peptide is SEQ ID NO: 8.
Synthesis method: SPPS_P; SC_P; CP_M1
UPLC02: Rt=10.9 min
LCMS01: Rt=2.6 min; m/4=1503; m/5=1203

Example 21

N{Alpha}([Aib8,Glu22,Arg26,Arg34]-GLP-1-(7-37)-peptidyl)-N{Epsilon}[4-[3-[2-[2-[3-[[(4S)-4-carboxy-4-[[1-(19-carboxynonadecanoyl)piperidine-4-carbonyl]amino]butanoyl]amino]propoxy]ethoxy]ethoxy]propylamino]-4-oxobutanoyl]Lys-Gly-Gly-Ser-N{Epsilon}[4-[3-[2-[2-[3-[[(4S)-4-carboxy-4-[[1-(19-carboxynonadecanoyl)piperidine-4-carbonyl]amino]butanoyl]amino]propoxy]ethoxy]ethoxy]propylamino]-4-oxobutanoyl]Lys Chem. 41
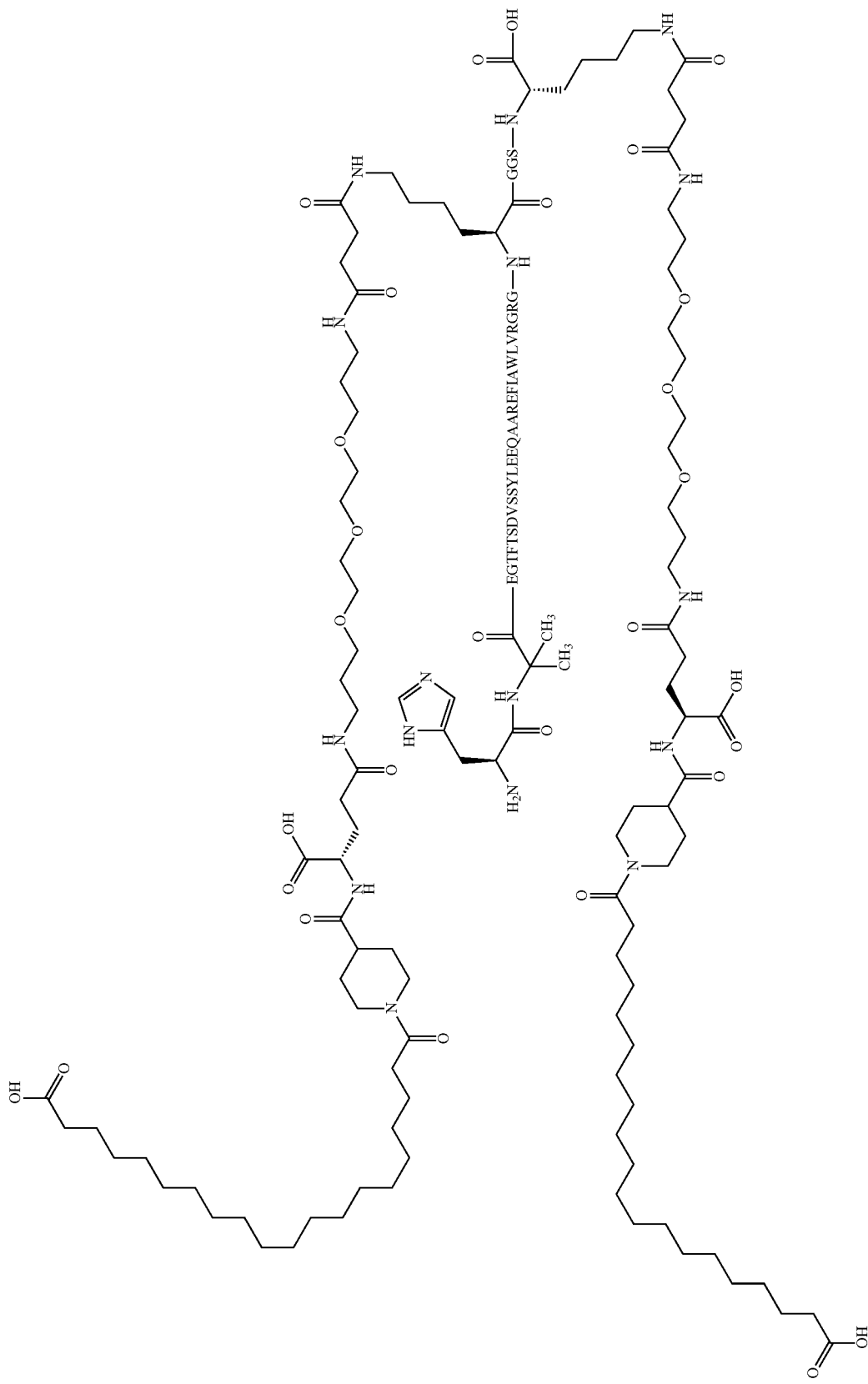

The peptide is SEQ ID NO: 4.
Synthesis method: SPPS_P; SC_P; CP_M1
UPLC02: Rt=11.1 min
LCMS01: Rt=2.7 min; m/3=1897; m/4=1423; m/5=1139

Example 22

N{Alpha}([Aib8,Glu22,Arg26,Arg34]-GLP-1-(7-37)-peptidyl)-N{Epsilon}[2-[2-[3-[2-[2-[3-[[(4S)-4-carboxy-4-(19-carboxynonadecanoylamino)butanoyl]amino]propoxy]ethoxy]ethoxy]propylamino]-2-oxoethoxy]acetyl]Lys-Gly-Gly-Ser-N{Epsilon}[2-[2-[3-[2-[2-[3-[[(4S)-4-carboxy-4-(19-carboxynonadecanoylamino)butanoyl]amino]propoxy]ethoxy]ethoxy]propylamino]-2-oxoethoxy]acetyl]Lys Chem. 42
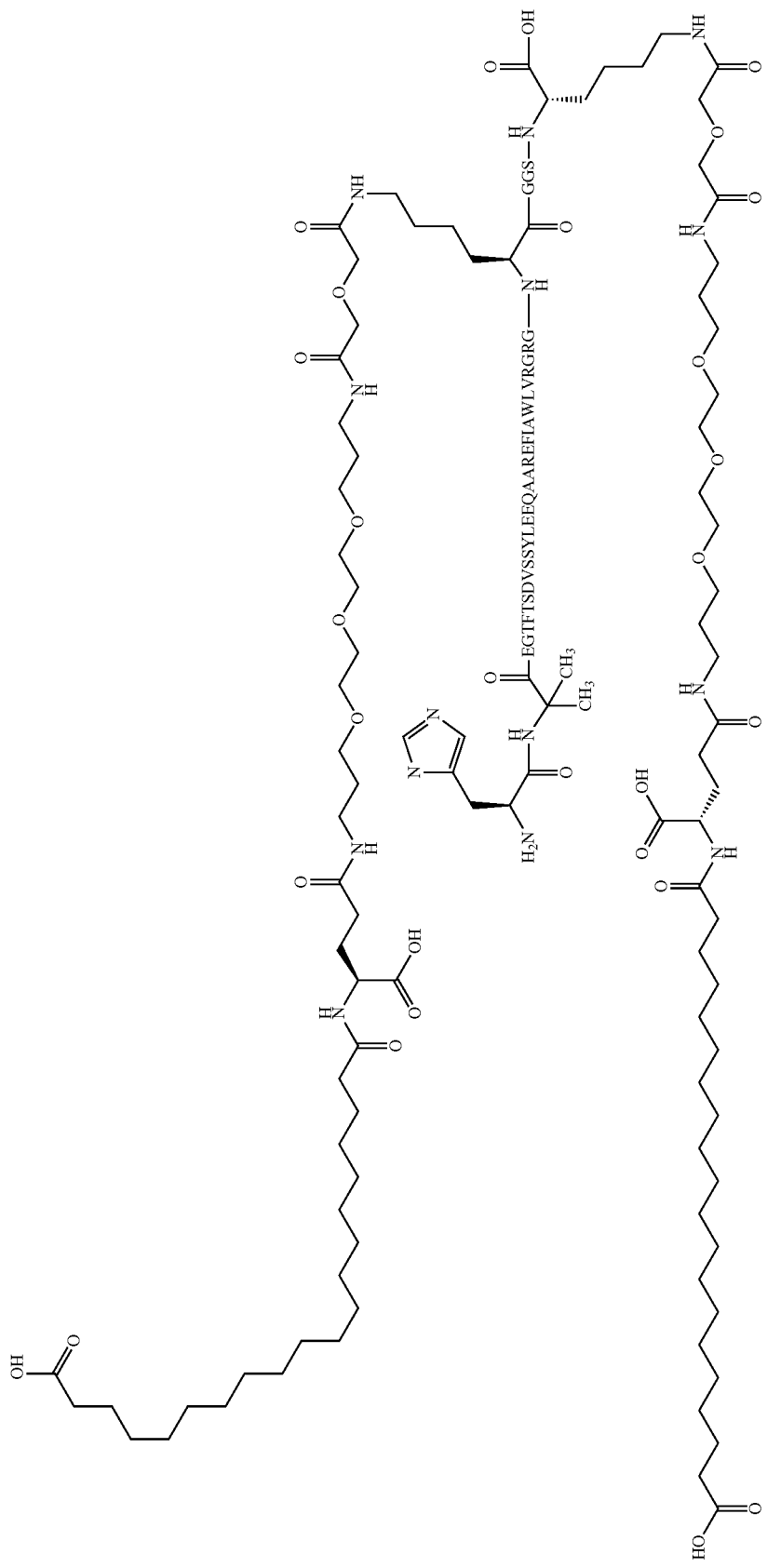

The peptide is SEQ ID NO: 4.
Synthesis method: SPPS_P; SC_P; CP_M1
UPLC02: Rt=10.7 min
LCMS01: Rt=2.6 min; m/3=1834; m/4=1376; m/5=1101

Example 23

N{Alpha}([Aib8,Glu22,Arg26,Arg34]-GLP-1-(7-37)-peptidyl)-N{Epsilon}[4-[2-[2-[2-[[(4S)-4-carboxy-4-[[4-[(19-carboxynonadecanoylamino)methyl]cyclohexanecarbonyl]amino]butanoyl]amino]ethoxy]ethoxy]ethylamino]-4-oxobutanoyl]Lys-Gly-Gly-Ser-N{Epsilon}[4-[2-[2-[2-[[(4S)-4-carboxy-4-[[4-[(19-carboxynonadecanoylamino)methyl]cyclohexanecarbonyl]amino]butanoyl]amino]ethoxy]ethoxy]ethylamino]-4-oxobutanoyl]Lys Chem. 43
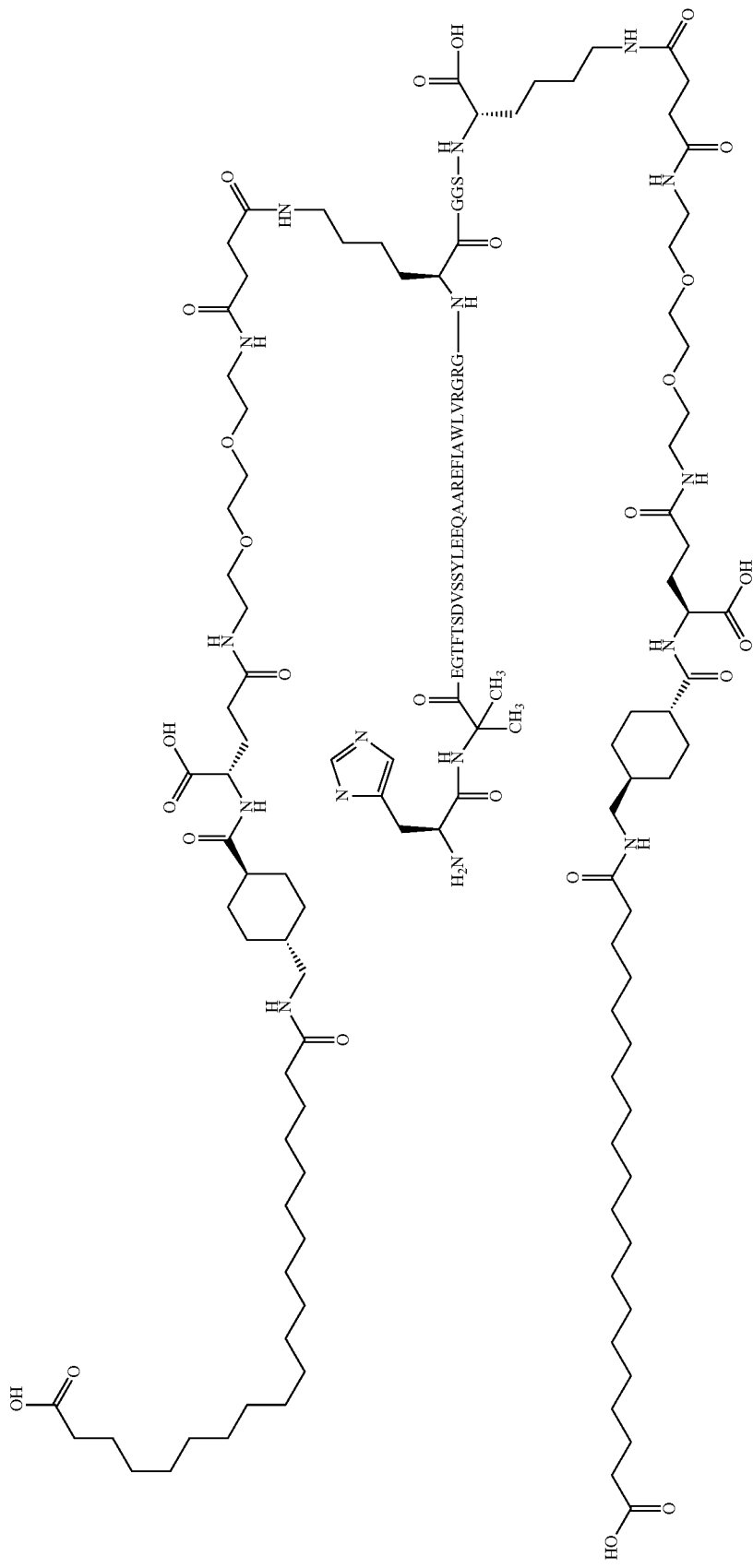

The peptide is SEQ ID NO: 4.
Synthesis method: SPPS_P; SC_P; CP_M1
UPLC02: Rt=11.1 min
LCMS01: Rt=2.7 min; m/4=1401.3; m/5=1121

Example 24

N{Alpha}([Aib8,Glu22,Arg26,Arg34]-GLP-1-(7-37)-peptidyl)-N{Epsilon}[2-[2-[2-[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]Lys-Gly-Gly-Ser-N{Epsilon}[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]Lys Chem. 44
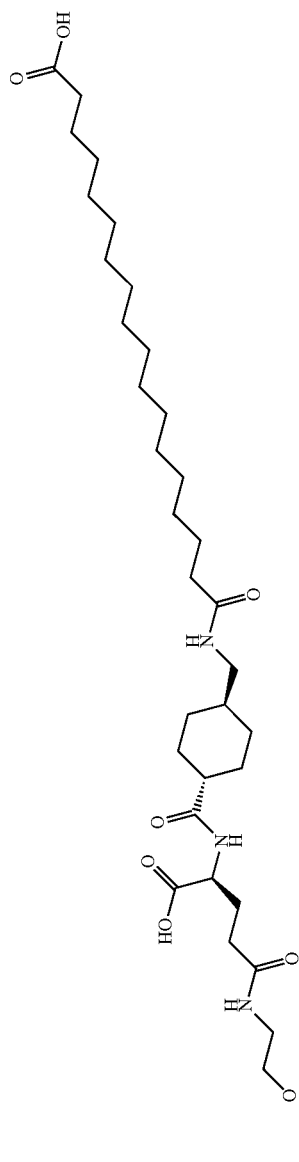
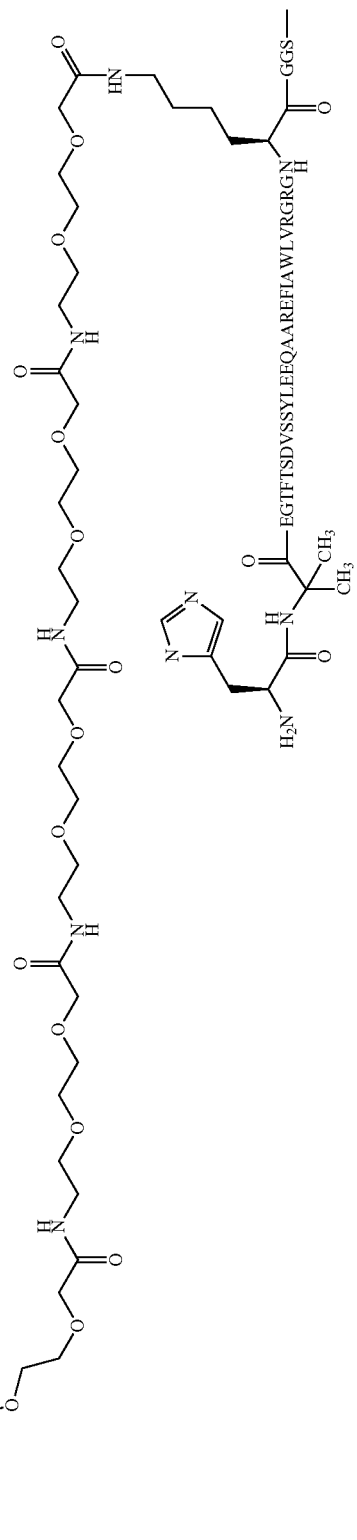

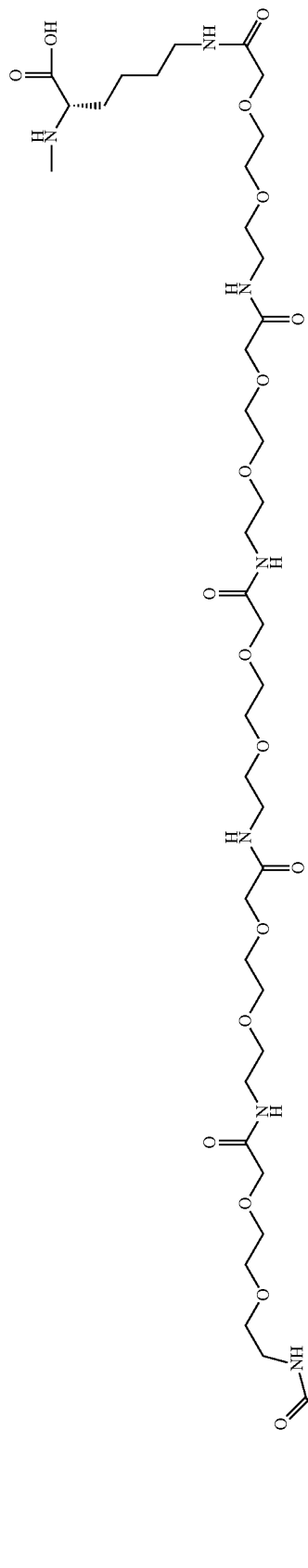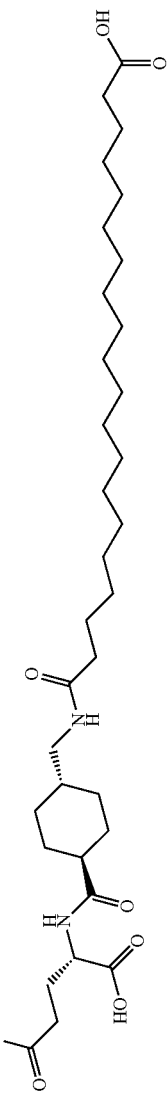

The peptide is SEQ ID NO: 4.
Synthesis method: SPPS_P; SC_P; CP_M1
UPLC02: Rt=10.7 min
LCMS01: Rt=2.6 min; m/4=1721; m/5=1377

Example 25

N{Alpha}([Aib8,Glu22,Arg26,Arg34]-GLP-1-(7-37)-peptidyl)-N{Epsilon}[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]Lys-Gly-Gly-Ser-N{Epsilon}[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]Lys

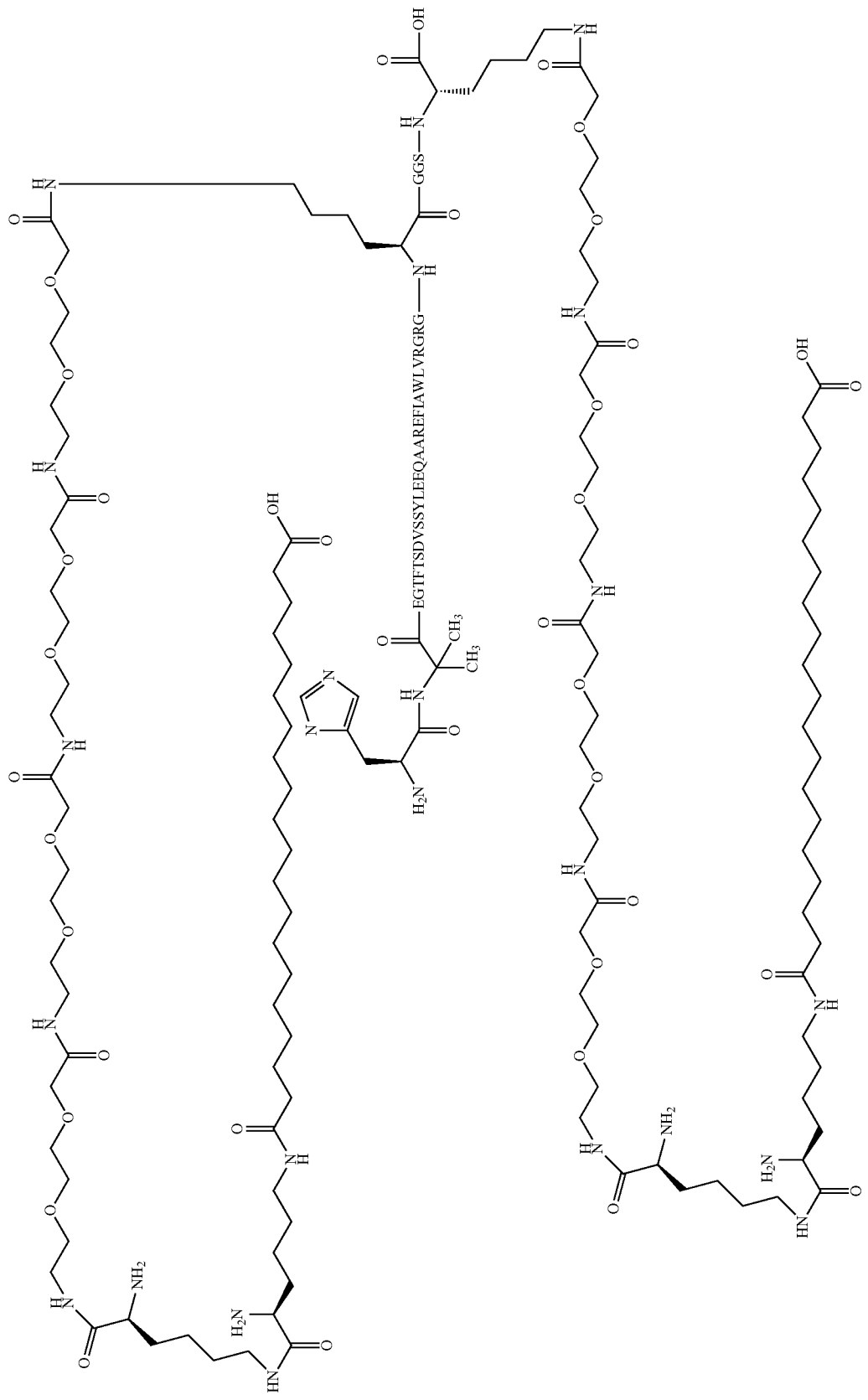
Chem. 45

The peptide is SEQ ID NO: 4.
Synthesis method: SPPS_L; SC_L; CP_M1
UPLC02: Rt=9.0 min
LCMS01: Rt=2.2 min, m/4=1570; m/5=1257

Example 26

N{Alpha}([Aib8,Glu22,Arg26,Arg34]-GLP-1-(7-37)-peptidyl)-N{Epsilon}[2-[2-[2-[[2-[2-[2-[[(4S)-4-carboxy-4-[[4-[(18-carboxyoctadecanoylamino)methyl]cyclohexanecarbonyl]amino]butanoyl]amino]ethoxy]ethoxy]acetyl]amino]ethoxy]ethoxy]acetyl]Lys-Gly-Gly-Ser-N{Epsilon}[2-[2-[2-[[2-[2-[2-[[(4S)-4-carboxy-4-[[4-[(18-carboxyoctadecanoylamino)methyl]cyclohexanecarbonyl]amino]butanoyl]amino]ethoxy]ethoxy]acetyl]amino]ethoxy]ethoxy]acetyl]Lys Chem. 46
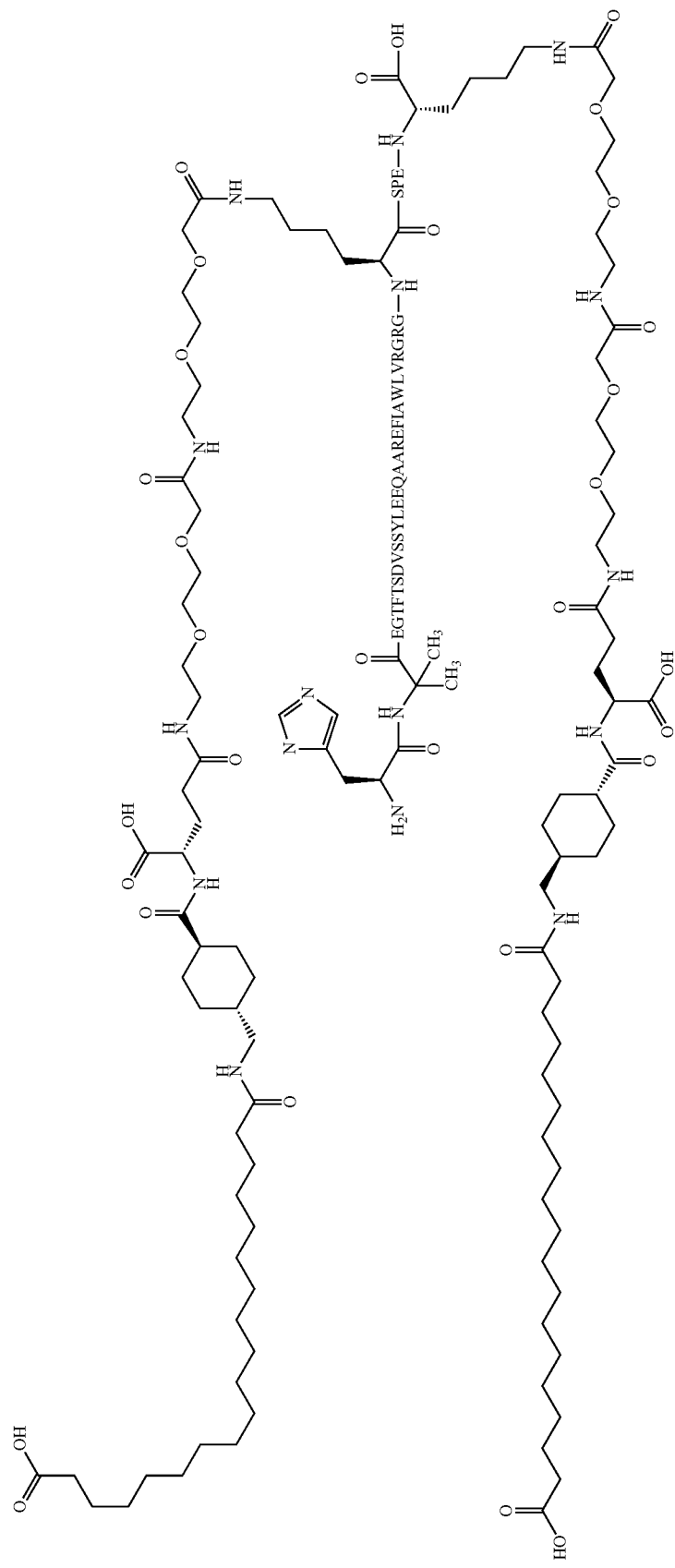

The peptide is SEQ ID NO: 4.
Synthesis method: SPPS_P; SC_P; CP_M1
UPLC02: Rt=10.5 min
LCMS01: Rt=2.7 min; m/4=1425; m/5=1140

Example 27

N{Alpha}([Aib8,Glu22,Arg26,Arg34]-GLP-1-(7-37)-peptidyl)-N{Epsilon}[2-[2-[2-[[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]Lys-Gly-Gly-Ser-N{Epsilon}[2-[2-[2-[[2-[2-[2-[[2-[2-[2-[[2-[2-[2-[[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]Lys

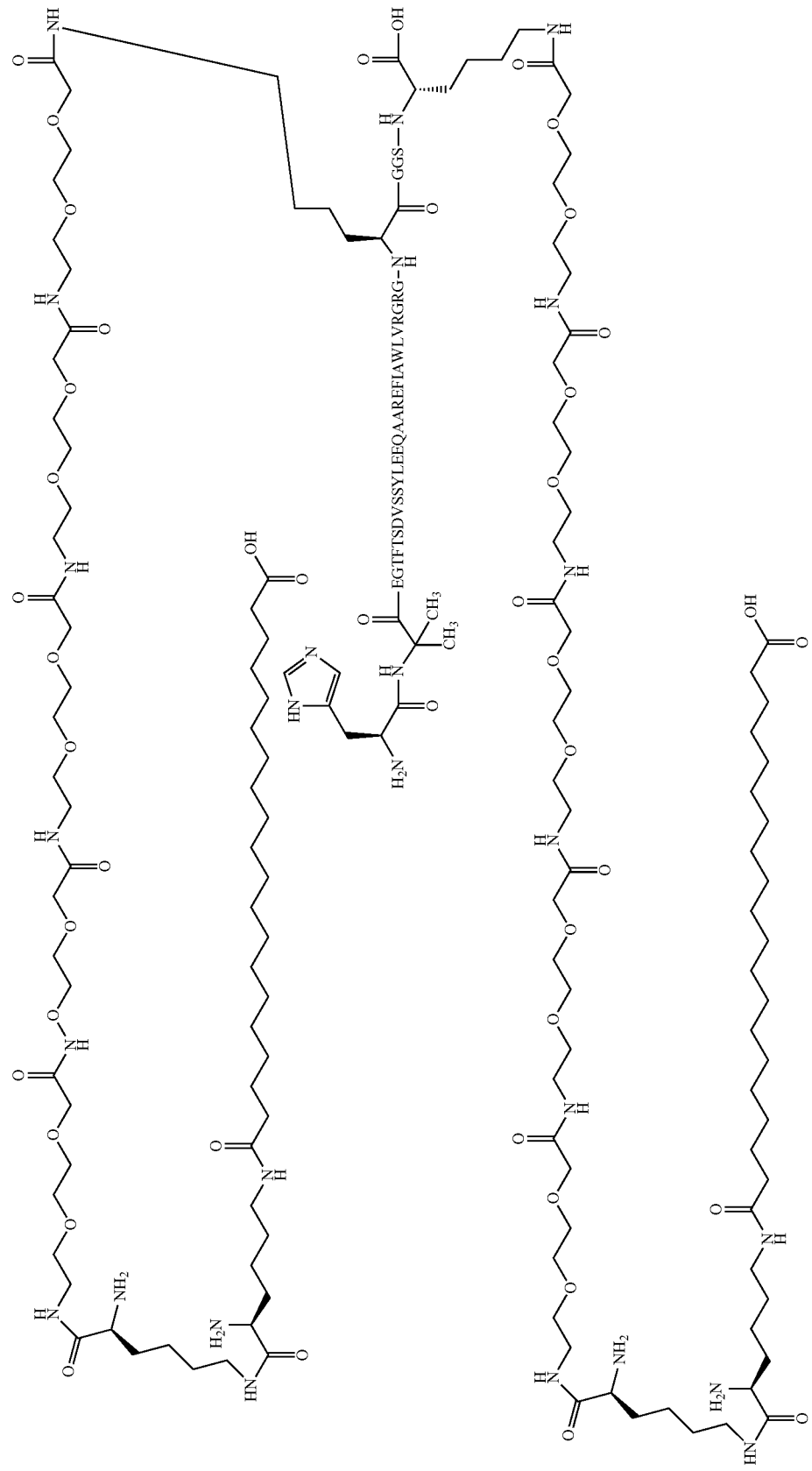

The peptide is SEQ ID NO: 4.
Synthesis method: SPPS_P; SC_L; CP_M2
UPLC02: Rt=8.8 min
LCMS01: Rt=2.2 min; m/4=1643; m/5=1315

Example 28

N{Alpha}([Aib8,Glu22,Arg26,Arg34]-GLP-1-(7-37)-peptidyl)-N{Epsilon}[2-[2-[2-[[2-[2-[2-[[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl] Lys-Gly-Gly-Ser-N{Epsilon}[2-[2-[2-[[2-[2-[2-[[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl] Lys

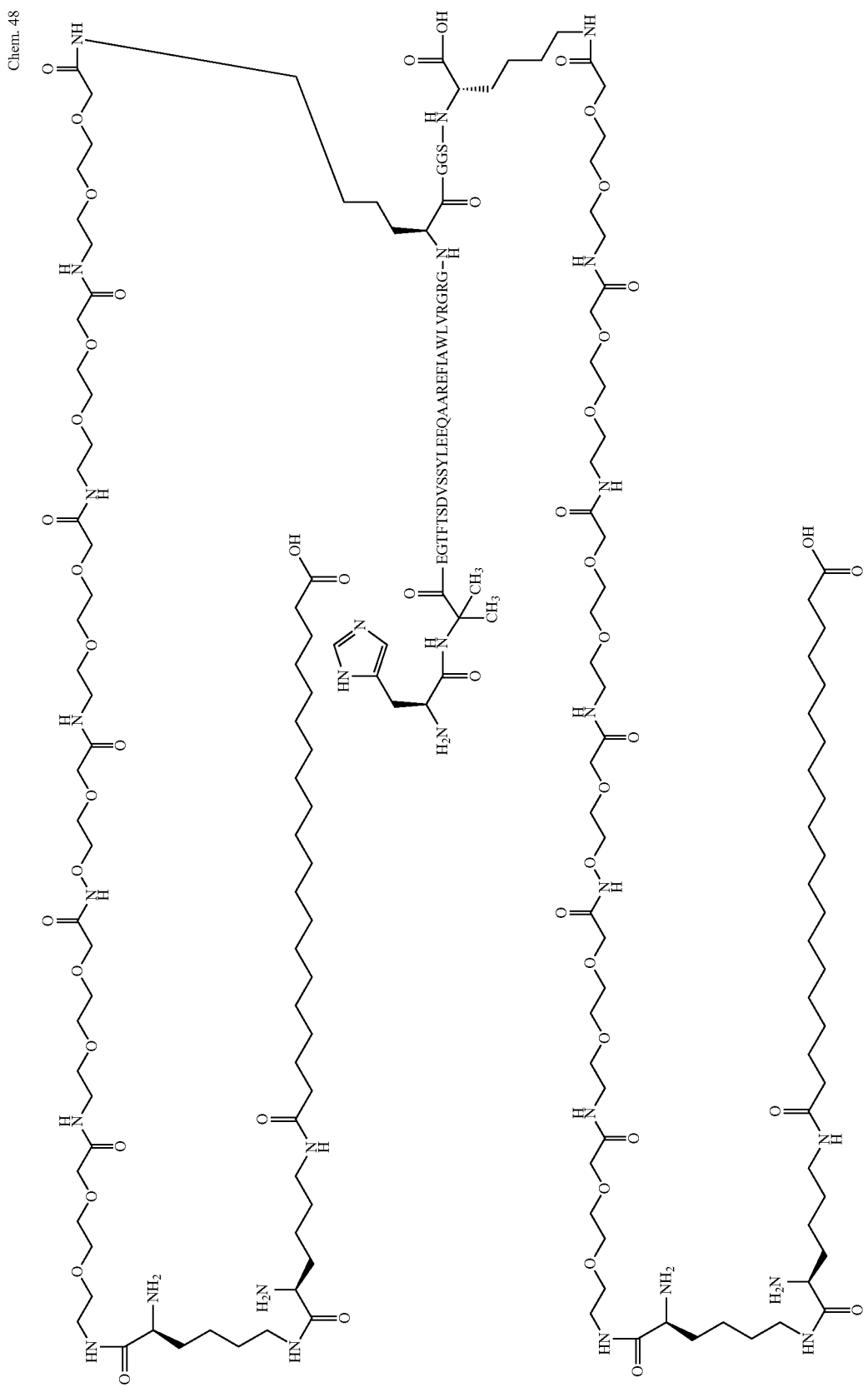

The peptide is SEQ ID NO: 4.
Synthesis method: SPPS_P; SC_L; CP_M2
UPLC02: Rt=8.6 min
LCMS01: Rt=2.2 min; m/4=1716; m/5=1373

Pharmacological Methods

Example 29

In Vitro Potency

The purpose of this example is to test the activity, or potency, of the GLP-1 derivatives in vitro. The in vitro potency is the measure of human GLP-1 receptor activation in a whole cell assay.

The potencies of the GLP-1 derivatives of Examples 1-28 were determined as described below. Semaglutide was included for comparison.

Principle

In vitro potency was determined by measuring the response of the human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in Cell Culture Medium. They were aliquoted and stored in liquid nitrogen. Before each assay an aliquot is taken up and washed twice in PBS before being suspended at the desired concentration in the assay specific buffer. For 96-well plates the suspension was made to give a final concentration of $5 \times 10^3$ cells/well.

Materials

The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Buffers

Cell Culture Medium consisted of DMEM medium with 10% FBS (Fetal Bovine Serum; Invitrogen 16140-071), 1 mg/ml G418 (Invitrogen 15140-122), 240 nM MTX (methotrexate; Sigma M9929) and 1% pen/strep (penicillin/streptomycin; Invitrogen 15140-122).

Assay Medium consisted of DMEM w/o phenol red, 10 mM Hepes and 1× Glutamax. The Assay Buffer consisted of 2% ovalbumin and 0.2% Pluronic F-68 in Assay Medium.

Procedure

1) Cell stocks were thawed in a 37° C. water bath.
2) Cells were washed three times in PBS.
3) The cells were counted and adjusted to $5 \times 10^3$ cells/50 μl ($1 \times 10^5$ cells/ml) in Assay Medium. A 50 μl aliquot of cells was transferred to each well in the assay plate.
4) Stocks of the test compounds and reference compounds were diluted to a concentration of 0.2 μM in Assay Buffer. Compounds were diluted 10-fold to give the following concentrations: $2 \times 10^{-7}$ M, $2 \times 10^{-5}$ M; $2 \times 10^{-9}$ M, $2 \times 10^{-10}$ M, $2 \times 10^{-11}$ M, $2 \times 10^{-12}$ M, $2 \times 10^{-13}$ M, and $2 \times 10^{-14}$ M.
5) A 50 μl aliquot of compound or blank was transferred from the dilution plate to the assay plate. Compounds were tested at the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M, $1 \times 10^{-13}$ M, and $1 \times 10^{-14}$ M.
6) The assay plate was incubated for 3 h in a 5% $CO_2$ incubator at 37° C.
7) The assay plate was removed from the incubator and allowed to stand at room temperature for 15 min.
8) A 100 μl aliquot of steadylite plus reagent was added to each well of the assay plate (reagent was light sensitive).
9) Each assay plate was covered with aluminum foil to protect it from light and shaken for 30 min at room temperature.
10) Each assay plate was read in a Packard TopCount NXT instrument.

Calculations and Results

The data from the TopCount instrument were transferred to GraphPad Prism software. The software performs a non-linear regression (log(agonist) vs response). $EC_{50}$ values which were calculated by the software and reported in pM are shown in Table 1 below.

A minimum of two replicates was measured for each sample. The reported values are averages of the replicates.

TABLE 1

| In vitro potency | |
|---|---|
| Compound of Example no. | $EC_{50}$ (pM) |
| 1 | 55 |
| 2 | 36 |
| 3 | 43 |
| 4 | 74 |
| 5 | 61 |
| 6 | 93 |
| 7 | 381 |
| 8 | 260 |
| 9 | 101 |
| 10 | 27 |
| 11 | 27 |
| 12 | 24 |
| 13 | 24 |
| 14 | 22 |
| 15 | 20 |
| 16 | 25 |
| 17 | 12 |
| 18 | 13 |
| 19 | 6.2 |
| 20 | 8.4 |
| 21 | 19 |
| 22 | 10 |
| 23 | 22 |
| 24 | 7.0 |
| 25 | 10 |
| 26 | 13 |
| 27 | 4.4 |
| 28 | 3.4 |
| semaglutide | 8.3 |

All compounds have potency data that confirms that they are GLP-1 receptor agonists.

Example 30

GLP-1 Receptor Binding

The purpose of this example is to test the receptor binding of the GLP-1 derivatives in vitro. The receptor binding is a measure of affinity of a derivative for the human GLP-1 receptor.

Principle

The receptor binding of the GLP-1 derivatives of Examples 1-28 to the human GLP-1 receptor was measured in a competitive binding assay. In this type of assay a labelled ligand (in this case $^{125}$I-GLP-1) is bound to the receptor. Each derivative is added in a series of concentrations to isolated membranes containing the human GLP-1 receptor and displacement of the labelled ligand is monitored. The receptor binding is reported as the concentration at which half of the labelled ligand is displaced from the receptor, the $IC_{50}$ value. Semaglutide was included as comparative compound. In order to test the binding of the derivatives to albumin, the assay is performed in a low concentration of serum albumin (max. 0.001% final assay concentration as well as in the presence of a considerably higher concentration of serum albumin (2.0% final assay concentration). An increase of the $IC_{50}$ value in the presence of serum albumin indicates an affinity to serum albumin and represents a method to predict a protracted pharmacokinetic profile of the test substance in animal models.

Materials

The following chemicals were used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, MgCl$_2$ (Merck 1.05832.1000), Tween 20 (Amresco 0850C335), SPA particles (wheat germ agglutinin (WGA) SPA beads, Perkin Elmer RPNQ0001), [$^{125}$I]-GLP-1]-(7-36)NH$_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM MgCl$_2$, 0.005% Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation

The cells used in this assay (clone FCW467-12A) were BHK cells with BHKTS13 as a parent cell line. The cells express the human GLP-1 receptor.

The cells were grown at 5% CO$_2$ in DMEM, 10% fetal calf serum, 1% Pen/Strep (Penicillin/Streptomycin) and 1.0 mg/ml of the selection marker G418.

To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX™ dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay in the presence of low HSA (0.005%) 50 µl of the assay buffer was added to each well of an assay plate. Assay continued with step 3.
2. For the receptor binding assay in the presence of high HSA (2%) 50 µl of the 8% albumin stock was added to each well of an assay plate. Assay continued with step 3.
3. Test compounds were serially diluted to give the following concentrations: $8\times10^{-7}$ M, $8\times10^{-8}$ M, $8\times10^{-9}$ M, $8\times10^{-10}$ M, $8\times10^{-11}$ M, $8\times10^{-12}$ M and $8\times10^{-13}$ M. Twenty-five µl were added to appropriate wells in the assay plate.
4. Cell membrane aliquots were thawed and diluted to their working concentration. Fifty µl were added to each well in the assay plate.
5. WGA SPA beads were suspended in assay buffer at 20 mg/ml. The suspension was diluted to 10 mg/ml in assay buffer just prior to addition to the assay plate. Fifty µl were added to each well in the assay plate.
6. The incubation was started by adding 25 µl of 480 pM solution of [$^{125}$I]-GLP-1]-(7-36)NH$_2$ to each well of the assay plate. A 25 µl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations

The data from the TopCount instrument were transferred to GraphPad Prism software. The software averaged the values for the replicates and performed a non-linear regression. $IC_{50}$ values were calculated by the software and reported in nM.

Results

The following results were obtained:

TABLE 2

| GLP-1 receptor binding | | |
|---|---|---|
| Compound of Example no. | Low HSA $IC_{50}$ (nM) | High HSA $IC_{50}$ (nM) |
| 1 | 0.75 | 275 |
| 2 | 1.4 | ≥1000 |
| 3 | 1.2 | 185 |
| 4 | 0.85 | 113 |
| 5 | 1.1 | 101 |
| 6 | 1.0 | ≥1000 |
| 7 | 2.2 | 197 |
| 8 | 0.43 | 383 |
| 9 | 1.6 | 21 |
| 10 | 1.3 | 123 |
| 11 | 1.5 | 116 |
| 12 | 1.4 | 212 |
| 13 | 1.4 | 160 |
| 14 | 1.5 | 530 |
| 15 | 1.6 | 928 |
| 16 | 1.4 | 602 |
| 17 | 1.8 | 99 |
| 18 | 2.3 | 219 |
| 19 | 2.4 | 142 |
| 20 | 4.1 | 270 |
| 21 | 1.3 | 177 |
| 22 | 0.82 | 194 |
| 23 | 1.4 | 201 |
| 24 | 0.67 | 84 |
| 25 | 0.22 | 38 |
| 26 | 0.88 | 202 |
| 27 | 0.08 | 30 |

TABLE 2-continued

GLP-1 receptor binding

| Compound of Example no. | Low HSA $IC_{50}$ (nM) | High HSA $IC_{50}$ (nM) |
|---|---|---|
| 28 | 0.05 | 30 |
| semaglutide | 0.56 | 324 |

All compounds showed a very good binding to the GLP-1 receptor in the absence of albumin, and most compounds also showed a very good binding in the presence of albumin. The two compounds that had $IC_{50}$ values 000 exceeded the detection limit of the assay.

Example 31

Pharmacokinetic Study in Minipigs

The purpose of this study is to determine the protraction in vivo of the GLP-1 derivatives after i.v. administration to minipigs, i.e. the prolongation of their time in the body and thereby their time of action. This is done in a pharmacokinetic (PK) study, where the terminal half-life of the derivative in question is determined. By terminal half-life is meant the time it takes to halve a certain plasma concentration in the terminal elimination phase.

The derivatives of Examples 1-5 were dosed with 2 nmol/kg, the derivative of Example 6 was dosed with 5 nmol/kg, and the derivatives of Examples 7-9 were dosed with 15 nmol/kg. Semaglutide was included for comparison (1.5 nmol/kg).

Male Göttingen minipigs were obtained from Ellegaard Göttingen Minipigs (Dalmose, Denmark) approximately 7-14 months of age and weighing approximately 16-35 kg were used in the studies. The minipigs were housed either individually (pigs with permanent catheters) or in a group and fed restrictedly once or twice daily with SDS minipig diet (Special Diets Services, Essex, UK).

After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between successive GLP-1 derivative dosings.

The GLP-1 derivatives were dissolved in 50 mM sodium phosphate, 70-145 mM sodium chloride, 0.05% tween 80, pH 7.4 to a concentration of usually from 20-60 nmol/ml.

Intravenous injections (the volume corresponding to for example 0.050-0.125 ml/kg) of the compounds were given through one catheter or through the venflon, and blood was sampled at predefined time points for up till 25 days post dosing (preferably through the other catheter or by venipuncture). Blood samples (for example 0.8 ml) were collected in EDTA buffer (8 mM) and then centrifuged at 4° C. and 1942G for 10 minutes.

Plasma was pipetted into Micronic tubes on dry ice, and kept at −20° C. until analysed for plasma concentration of the respective GLP-1 compound using LOCI. Individual plasma concentration-time profiles were analyzed by a non-compartmental pharmacokinetic method in Phoenix v. 6.2 (Pharsight Inc., Mountain View, Calif., USA), or other relevant software for PK analysis, and the resulting terminal half-lives (harmonic mean) determined.

Results

TABLE 3

Pharmacokinetic study in minipigs (i.v.)

| Compound of Example no. | Terminal half-live (h) |
|---|---|
| 1 | 121 |
| 2 | 110 |
| 3 | 147 |
| 4 | 137 |
| 5 | 131 |
| 6 | 99 |
| 7 | 106 |
| 8 | 137 |
| 9 | 167 |
| semaglutide | 55 |

The tested derivatives of the invention have very long terminal half-lives (at least twice that of semaglutide).

Example 32

Pharmacodynamic Study in db/db Mice

The purpose of the study is to verify the acute effect of the GLP-1 derivatives on blood glucose (BG) and body weight (BW) in a diabetic setting.

The GLP-1 derivatives of Examples 1-8, and 10 were tested in a single-dose study in an obese, diabetic mouse model (db/db mice) as described in the following. The derivatives were tested at a dose of 10 nmol/kg (Example 10), or 30 nmol/kg (Examples 1-8).

Six db/db mice per compound to be tested (from Taconic, Denmark), fed from birth with the diet NIH31 (NIH 31M Rodent Diet, commercially available from Taconic Farms, Inc., US, see www.taconic.com), were enrolled for the study at the age of approximately 10 weeks. The mice were given free access to standard chow (e.g. Altromin 1324, Brogaarden, Gentofte, Denmark) and tap water and kept at 24° C. After 1-2 weeks of acclimatisation, the basal blood glucose was assessed twice on two consecutive days (i.e. at 9 am). The mice were allocated to treatment groups based on matching blood glucose levels and body weights. The mice were used in experiments with a duration of 120 hours, and were re-used for up to 2 times. After the last experiment the mice were euthanised.

The animals were grouped to receive treatment as follows: Vehicle, s.c., or GLP-1 derivative, s.c., where vehicle was either 50 mM sodium phosphate, 70 mM sodium chloride, 0.05% polysorbate 80, pH 7.4 (Examples 1, 2, 7, and 10); or 50 mM sodium phosphate, 145 mM sodium chloride, 0.05% (w/v) tween 80, pH 7.4 (Examples 3-6, and 8).

The GLP-1 derivative was dissolved in the vehicle, to a dosing concentration of 1.7-17 nmol/ml dependent on the respective dose. Animals were dosed once, at the start of the experiment, s.c. with a dose-volume of 6 ml/kg (i.e. 300 µl per 50 g mouse).

On the day of dosing, blood glucose was assessed at time −½h (8.30 am), the mice were weighed after this. The GLP-1 derivative was dosed at approximately 9 am (time 0). On the day of dosing, blood glucose was assessed at times 1, 2, 4 and 8 h (10 am, 11 am, 1 µm and 5 µm) after dosing.

On the following days, the blood glucose was assessed at time 24 h, 48 h, 72 h, and 96 h. On each day, the mice were weighed following blood glucose sampling.

The mice were weighed individually on a digital weighing scale.

Samples for the measurement of blood glucose were obtained from the tail tip capillary of conscious mice. Blood, 10 μl, was collected into heparinised capillaries and transferred to 500 μl glucose buffer (EKF system solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

The data are presented as percent change in blood glucose or body weight measured at the 48 h and the 96 h time points. For example, the percent change in blood glucose level at 48 h for each individual is calculated as follows: [[(blood glucose level at 48 h)−(basal blood glucose level)]/(basal blood glucose level)]×100%], where basal blood glucose level refers to the level before the administration of any treatment—and vice versa for the body weight change. A negative value refers to a % reduction.

The following results were obtained (averages of all individual determinations corresponding to the respective treatment):

TABLE 4

Effect on blood glucose and body weight in db/db mice

| Compound of Example no. | % change in blood glucose | | % change in body weight | |
|---|---|---|---|---|
| | 48 h | 96 h | 48 h | 96 h |
| 1 | −61 | −21 | −6 | −3 |
| 2 | −37 | −31 | −4 | −2 |
| 3 | −58 | −22 | −5 | −3 |
| 4 | −30 | −18 | −4 | −3 |
| 5 | −28 | −33 | −4 | −3 |
| 6 | −30 | −21 | −3 | −4 |
| 7 | −49 | −17 | −4 | −1 |
| 8 | −39 | −31 | −4 | −4 |
| 10 | −17 | −3 | −3 | −3 |

All derivatives tested showed effect in vivo by decreasing BG as well as BW after 48 h as well as after 96 h.

Example 33

Pharmacodynamic Study in LYD Pig

The purpose of this experiment is to investigate the effect of GLP-1 derivatives on food intake in pigs. This is done in a pharmacodynamic (PD) study as described below, in which food intake is measured from 1 to 4 days after administration of a single dose of the GLP-1 derivative, as compared to a vehicle-treated control group.

Female Landrace Yorkshire Duroc (LYD) pigs, approximately 3 months of age, weighing approximately 30-35 kg are used (n=3-4 per group). The animals are housed in a group for approximately 1 week during acclimatisation to the animal facilities. During the experimental period the animals are placed in individual pens at least 2 days before dosing and during the entire experiment for measurement of individual food intake. The animals are fed ad libitum with pig food (Svinefoder, Danish Top, or HRC Sow and Weaner Diet) at all times both during the acclimatisation and the experimental period. Food intake is monitored either on line by logging the weight of food every 15 minutes, or manually. The weight of food is recorded daily for each animal (24 h periods) from day −2 to day 6 (120 hour) after dose, administration inclusive.

The GLP-1 derivatives are first dissolved in a phosphate buffer (50 mM phosphate, 0.05% tween 80, pH 8; or 50 mM phosphate, 145 mM sodium chloride, 0.05% tween 80, pH 7.4) at the desired concentration (such as 12, 40, 120, 400 or 1200 nmol/ml corresponding to doses of 10, 15, or 30 nmol/kg). The phosphate buffer serves as vehicle. Animals are dosed with a single subcutaneous dose of the GLP-1 derivative or vehicle (usual dose volume 0.025 ml/kg) on the morning of day 1, and food intake is measured for 1-4 days after dosing. On the last day of each study, 1-4 days after dosing, a blood sample for measurement of plasma exposure of the GLP-1 derivative is taken from the jugular/anterior vena cava. The animals are re-used for three experiments. Plasma content of the GLP-1 derivatives is analysed using LOCI.

Food intake is calculated as mean 24 h food intake in 24 h intervals (0-24 h, 24-48 h, 48-72 h, and 72-96 h) and may, e.g., be indicated as percentage of the food intake of the vehicle group in the same time interval.

Statistical comparisons of the food intake in the 24 hour intervals in the vehicle vs. GLP-1 derivative group are done using two-way-ANOVA repeated measures, followed by Bonferroni post-test.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 analogue, wherein the GLP-1 analogue comprises a sequence of formula I:

$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$,    Formula I:

wherein $Xaa_7$ is L-histidine, (S)-2-Hydroxy-3-(1H-imidazol-4-yl)-propionic acid, D-histidine, desamino-histidine, homohistidine, $N^\alpha$-acetyl-histidine, $N^\alpha$-formyl-histidine, $N^\alpha$-methyl-histidine, 3-pyridylalanine, 2-pyridylalanine, or 4-pyridylalanine;

$Xaa_8$ is Ala, Gly, Ser, Aib, (1-aminocyclopropyl) carboxylic acid, or (1-aminocyclobutyl) carboxylic acid;

$Xaa_{12}$ is Phe or Leu;

$Xaa_{16}$ is Val or Leu;

$Xaa_{18}$ is Ser, Arg, Lys, Val, or Leu;

$Xaa_{19}$ is Tyr or Gln;

$Xaa_{20}$ is Leu or Met;

Xaa$_{22}$ is Gly or Glu;
Xaa$_{23}$ is Gln, Glu, Lys, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp, Lys, or His;
Xaa$_{33}$ is Val, Lys, or Arg;
Xaa$_{34}$ is Lys, Arg, His, Asn, or Gln;
Xaa$_{35}$ is Gly or Ala;
Xaa$_{36}$ is Arg, Lys, or Gly;
Xaa$_{37}$ is Gly or Pro;
Xaa$_{38}$ is Lys;
Xaa$_{39}$ is Ser, Gly, Ala, Glu, or Pro;
Xaa$_{40}$ is Ser, Gly, Ala, Glu, or Pro;
Xaa$_{41}$ is Ser, Gly, Ala, Glu, or Pro; and
Xaa$_{42}$ is Lys;
wherein
Lys at Xaa$_{42}$ is a first K residue, and Lys at Xaa$_{38}$ is a second K residue;
which derivative comprises a first and a second protracting moiety connected to said first and second K residue, respectively, wherein the first and the second protracting moiety is selected from Chem. 1, Chem. 1a, and Chem. 1b:

HOOC—(CH$_2$)$_{18}$—CO—*,            Chem. 1:

HOOC—(CH$_2$)$_{17}$—CO—*, and         Chem. 1a:

HOOC—(CH$_2$)$_{20}$—CO—*;              Chem. 1b:

or a pharmaceutically acceptable salt, amide, or ester thereof.

2. The derivative of claim 1, wherein the first and second protracting moeity is Chem. 1.

3. The derivative of claim 1, wherein in Formula I
Xaa$_7$ is L-histidine, (S)-2-Hydroxy-3-(1H-imidazol-4-yl)-propionic acid, D-histidine, desamino-histidine, N$^\alpha$-acetyl-histidine, N$^\alpha$-formyl-histidine, or N$^\alpha$-methyl-histidine;
Xaa$_8$ is Ala, Gly, Ser, Aib, (1-aminocyclopropyl) carboxylic acid, or (1-aminocyclobutyl) carboxylic acid;
Xaa$_{12}$ is Phe;
Xaa$_{16}$ is Val or Leu;
Xaa$_{18}$ is Ser, Arg, or Lys;
Xaa$_{19}$ is Tyr or Gln;
Xaa$_{20}$ is Leu or Met;
Xaa$_{22}$ is Gly or Glu;
Xaa$_{23}$ is Gln, Glu, Lys, or Arg;
Xaa$_{25}$ is Ala or Val;
Xaa$_{26}$ is Arg or Lys;
Xaa$_{27}$ is Glu, Lys, or Leu;
Xaa$_{30}$ is Ala or Glu;
Xaa$_{31}$ is Trp, Lys, or His;
Xaa$_{33}$ is Val, Lys, or Arg;
Xaa$_{34}$ is Lys, Arg, or Asn;
Xaa$_{35}$ is Gly;
Xaa$_{36}$ is Arg, Lys, or Gly;
Xaa$_{37}$ is Gly or Pro;
Xaa$_{38}$ is Lys;
Xaa$_{39}$ is Ser, Gly, Ala, Glu, or Pro;
Xaa$_{40}$ is Ser, Gly, Ala, Glu, or Pro;
Xaa$_{41}$ is Ser, Gly, Ala, Glu, or Pro; and
Xaa$_{42}$ is Lys.

4. The derivative of claim 3, wherein Xaa$_7$ is L-histidine or desamino-histidine.

5. The derivative of claim 4, wherein Xaa$_8$ is Aib.

6. The derivative of claim 3, wherein the GLP 1 analogue has a maximum of 10 amino acid changes when compared with GLP-1(7-37) (SEQ ID NO: 1).

7. The derivative of claim 3, wherein each of the first and the second protracting moiety is attached to the first and the second K residue, respectively, via a first and a second linker, respectively.

8. The derivative of claim 7, wherein each of the first and the second linker comprises at least one linker element selected from the following:

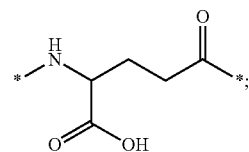
Chem. 2

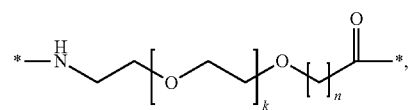
Chem. 3 wherein k is an integer in the range of 1-5, and n is an integer in the range of 1-5;

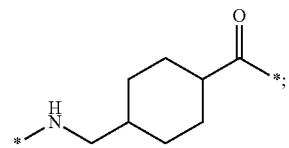
Chem. 4

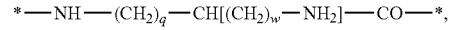
Chem. 5

*—NH—(CH$_2$)$_q$—CH[(CH$_2$)$_w$—NH$_2$]—CO—*, wherein q is an integer in the range of 0-5, and w is an integer in the range of 0-5, with the provisos that when w is 0 then q is an integer in the range of 1-5, and when q is 0 then w is an integer in the range of 1-5;

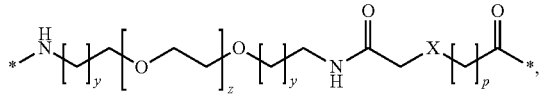
Chem. 6 wherein y is 1 or 2, z is 1 or 2, p is 0 or 1, and X designates a carbon atom or an oxygen atom; and

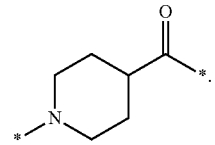
Chem. 10

9. The derivative of claim 3, wherein each of the first and the second linker comprises a linker element of Chem. 2.

10. The derivative of claim 3, wherein each of the first and the second linker comprises a linker element of Chem. 3.

11. The derivative of claim 10, wherein each of the first and the second linker comprises two linker elements of Chem. 3.

12. The derivative of claim 10, wherein in Chem. 3, n is 1 and k is 1.

13. The derivative of claim 3, wherein each of the first and the second linker comprises a linker element of Chem. 4.

14. The derivative of claim 13, wherein each of the first and the second linker comprises a linker element of Chem. 4, one linker element of Chem. 2 and two linker elements of Chem. 3 wherein k is 1 and n is 1, wherein these linker elements are interconnected via amide bonds.

15. A derivative of a GLP-1 analogue wherein said derivative is selected from the following:

Chem. 23
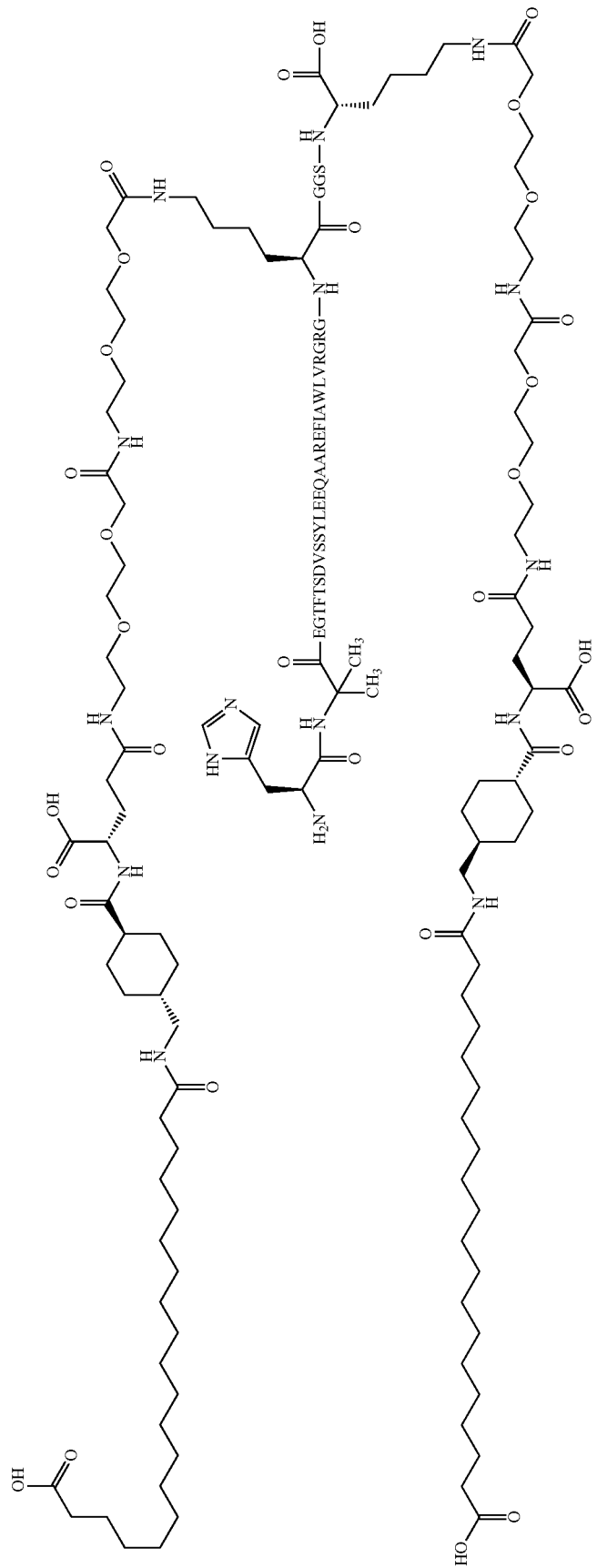
where the amino acid sequence is that of SEQ ID NO: 4,

Chem. 27
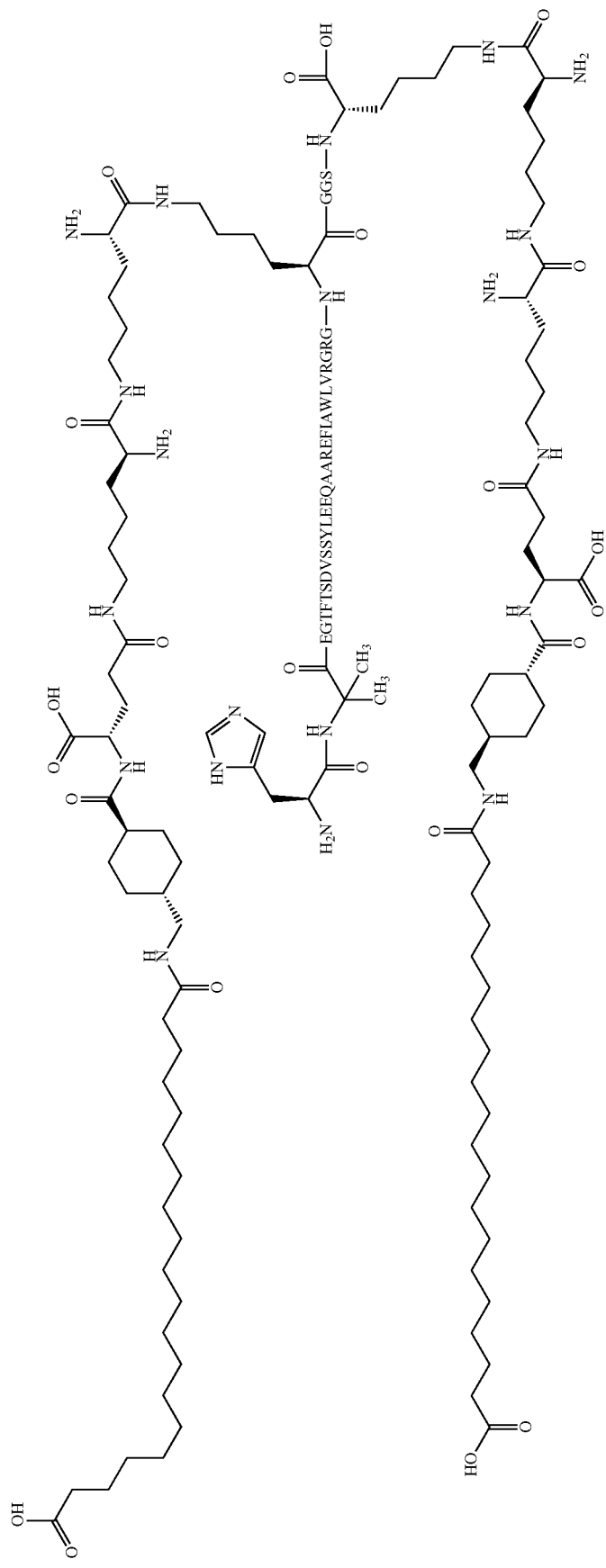
where the amino acid sequence is that of SEQ ID NO: 4,

Chem. 29
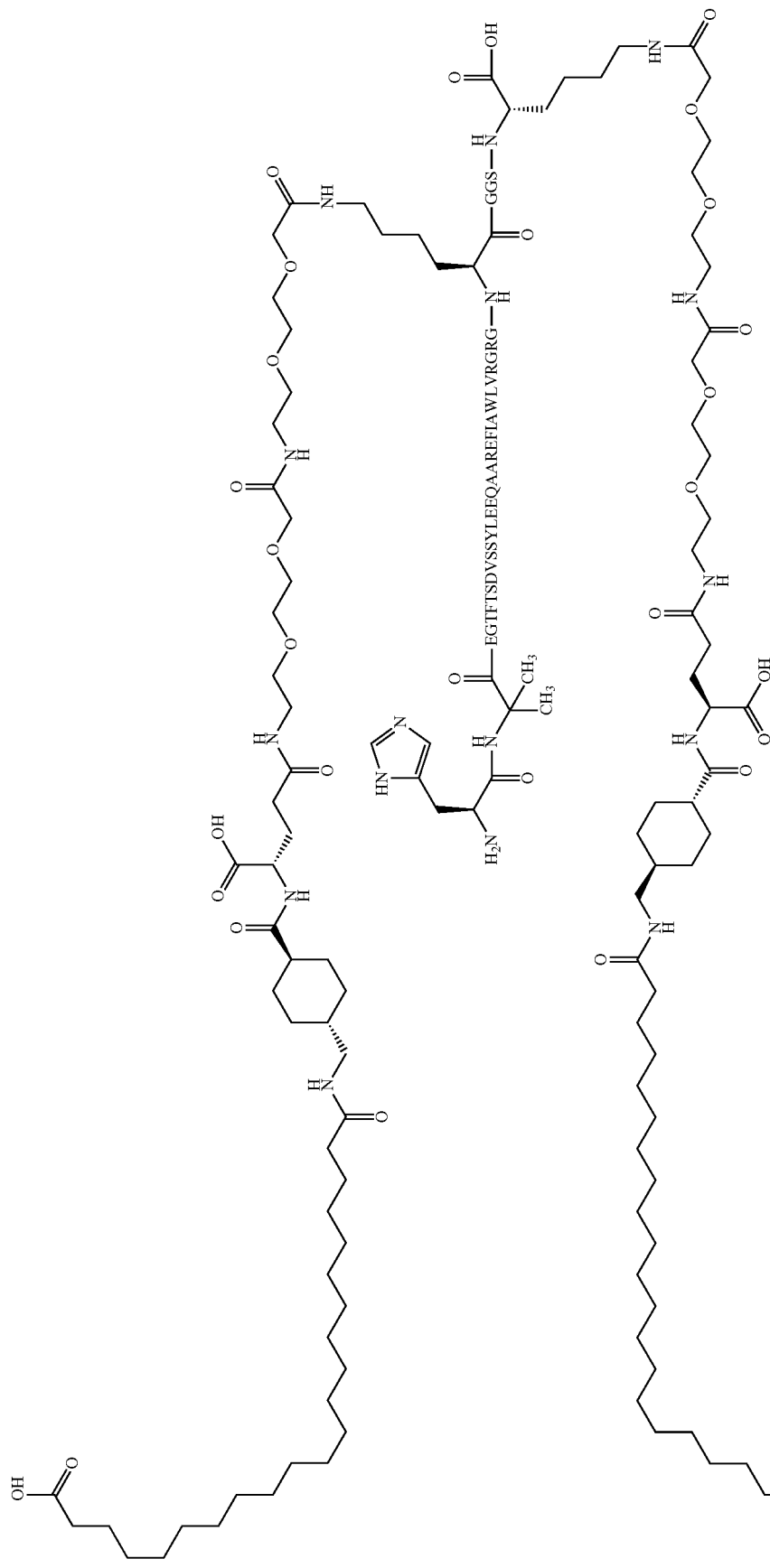
where the amino acid sequence is that of SEQ ID NO: 4.

Chem. 30
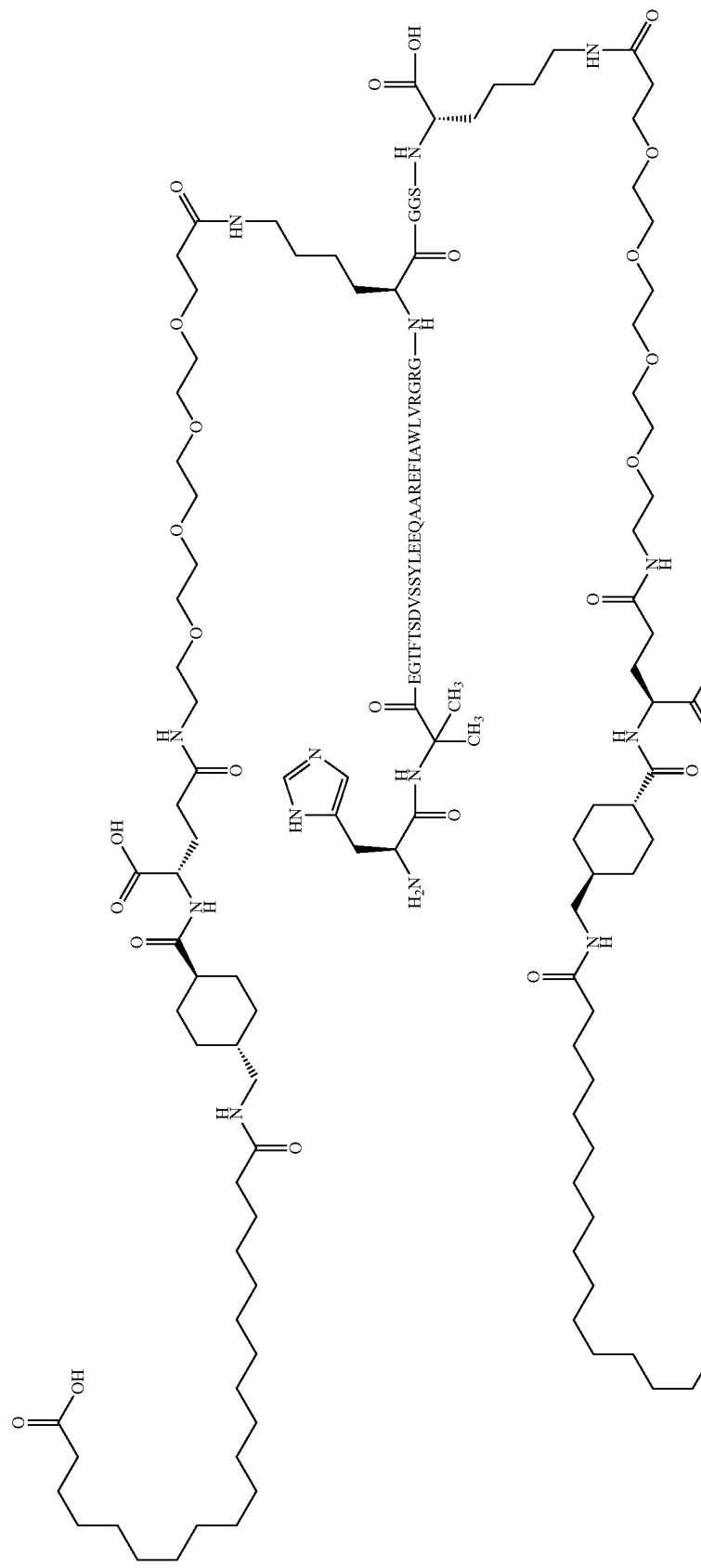
where the amino acid sequence is that of SEQ ID NO: 4,

Chem. 31
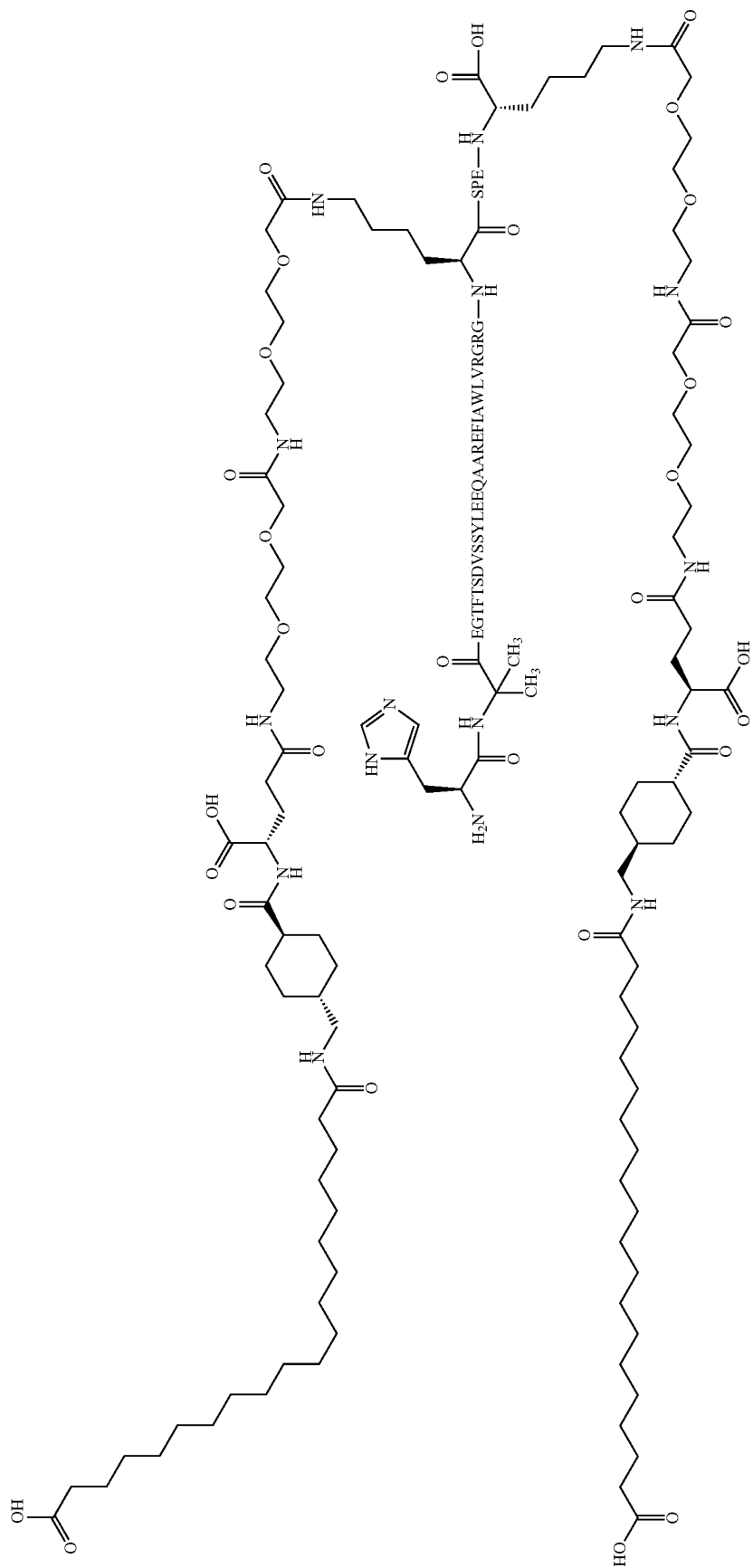
where the amino acid sequence is that of SEQ ID NO: 14,

Chem. 32
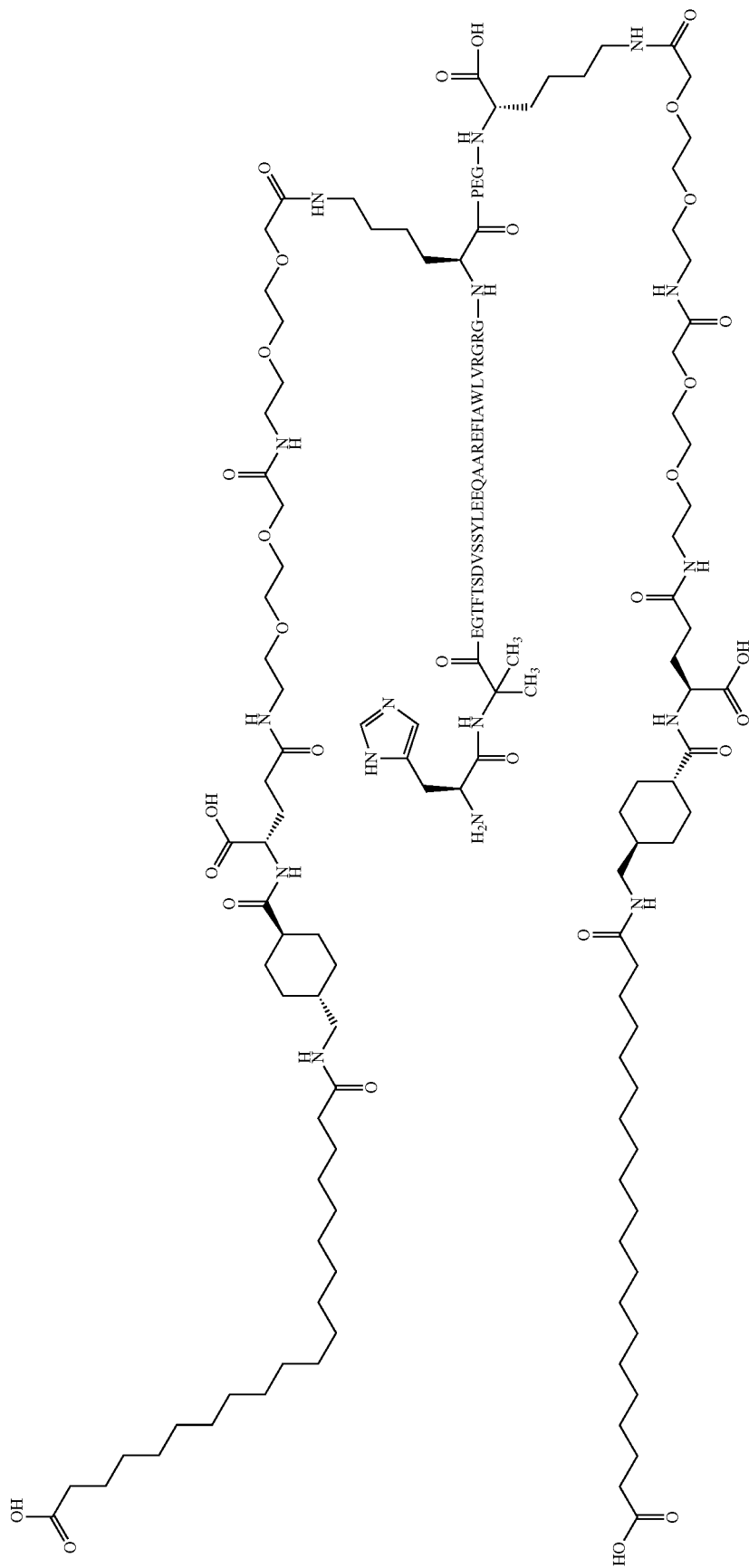
where the amino acid sequence is that of SEQ ID NO: 12,

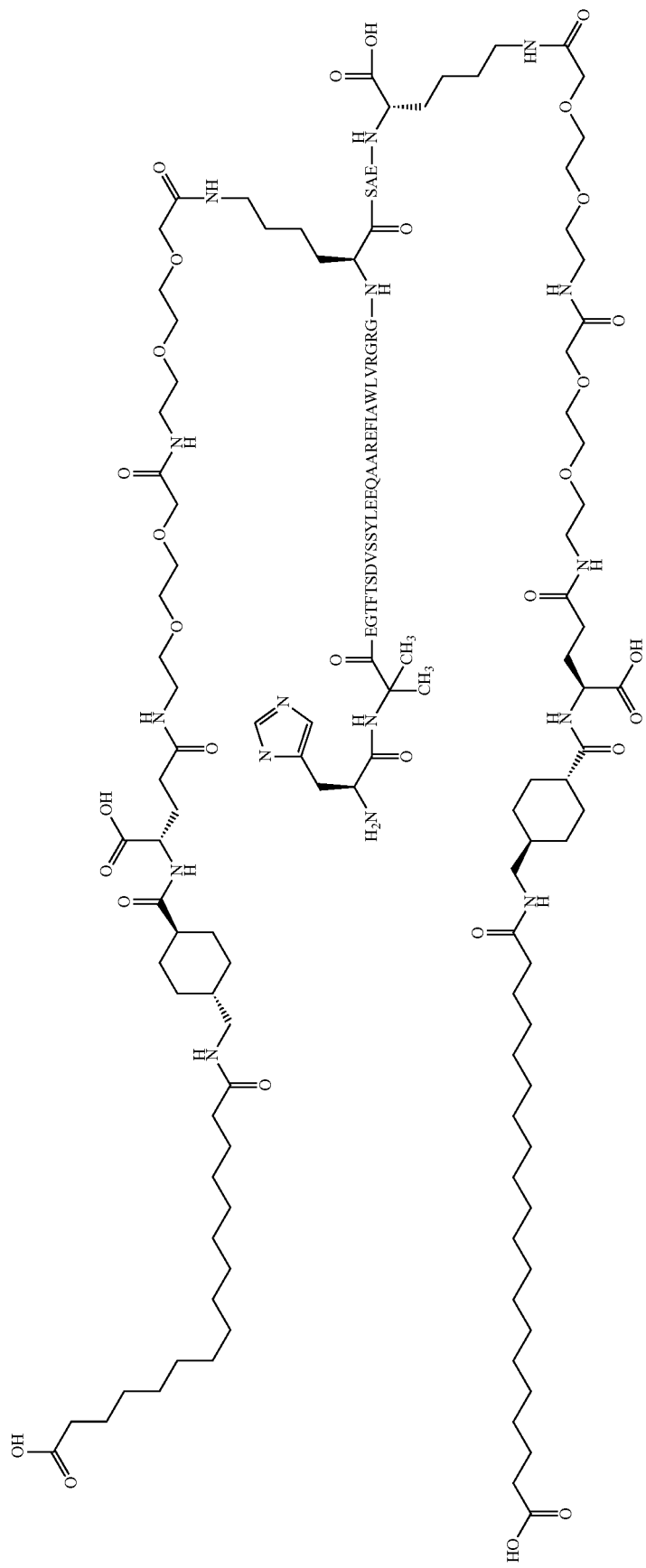
Chem. 33
where the amino acid sequence is that of SEQ ID NO: 13.

213 214
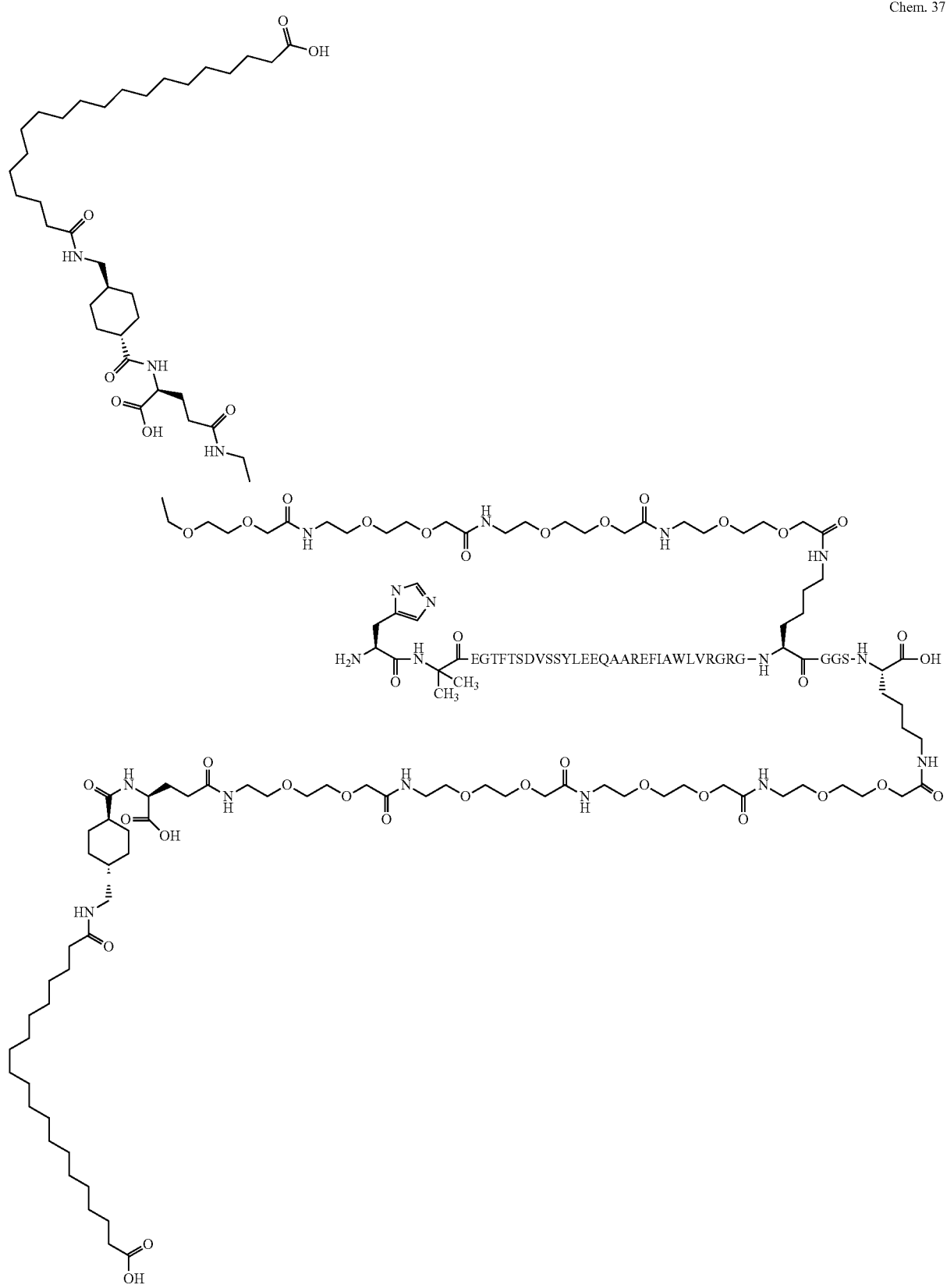
Chem. 37

215 216
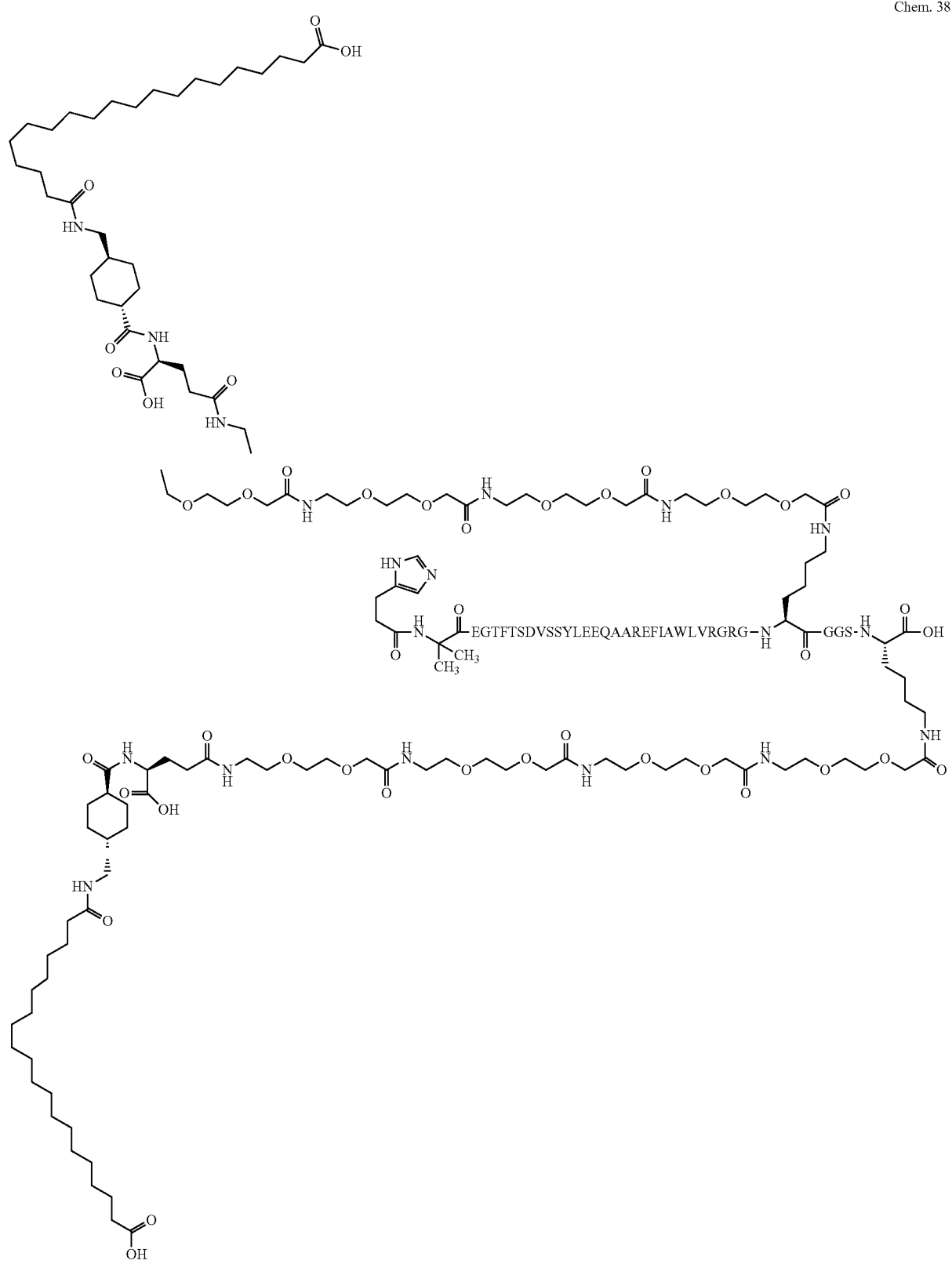
Chem. 38

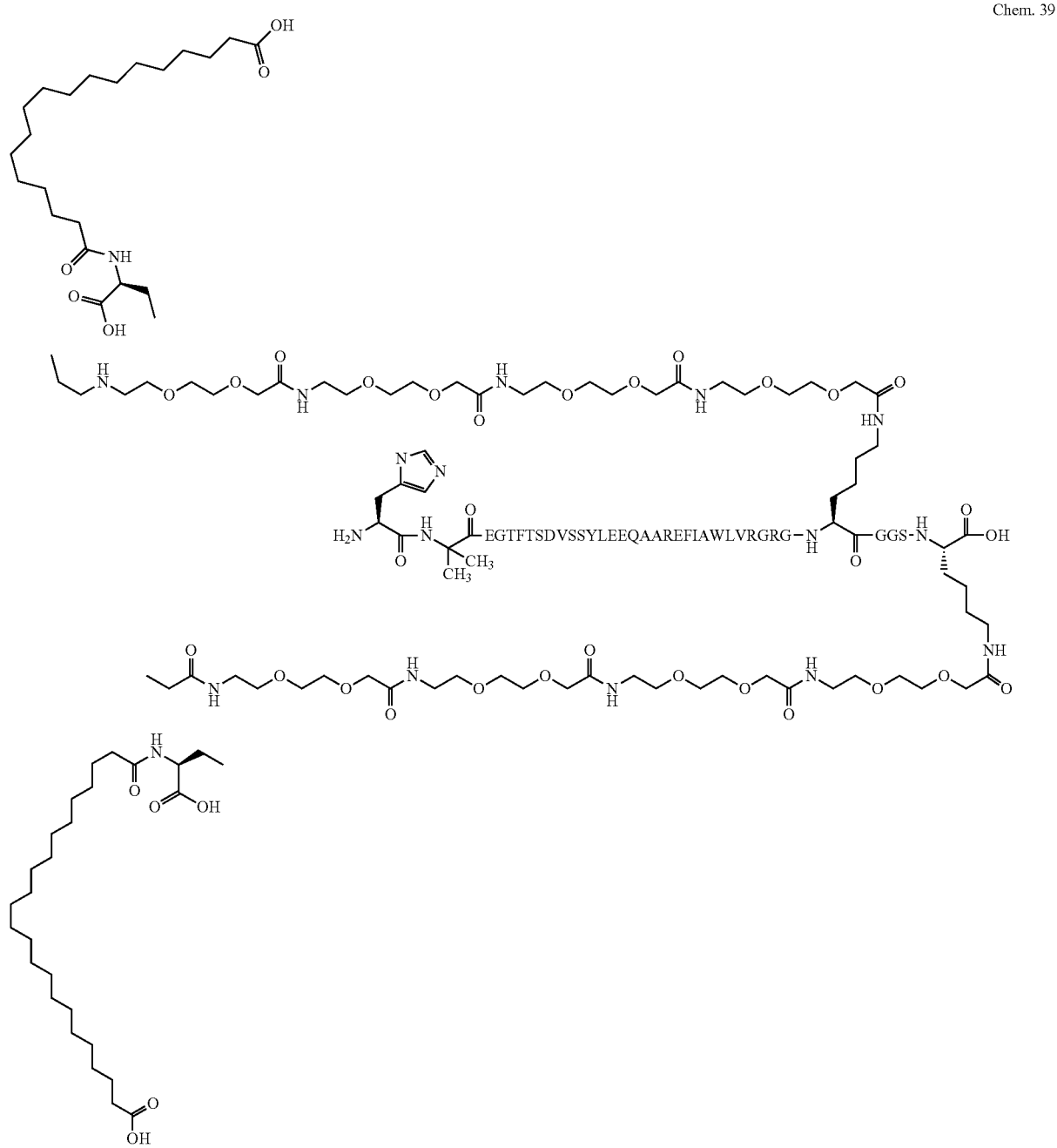
Chem. 39
where the amino acid sequence is that of SEQ ID NO: 4,

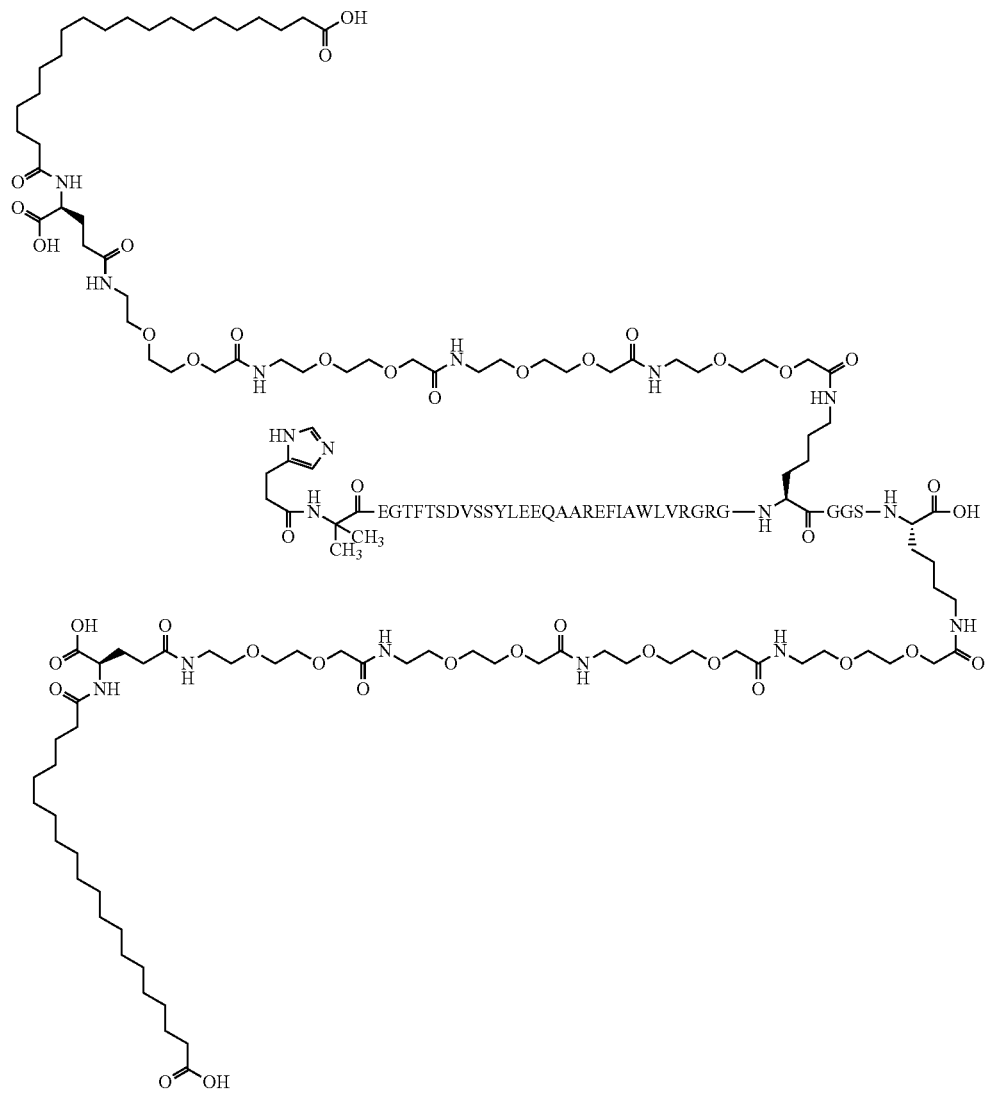
Chem. 40

Chem. 41
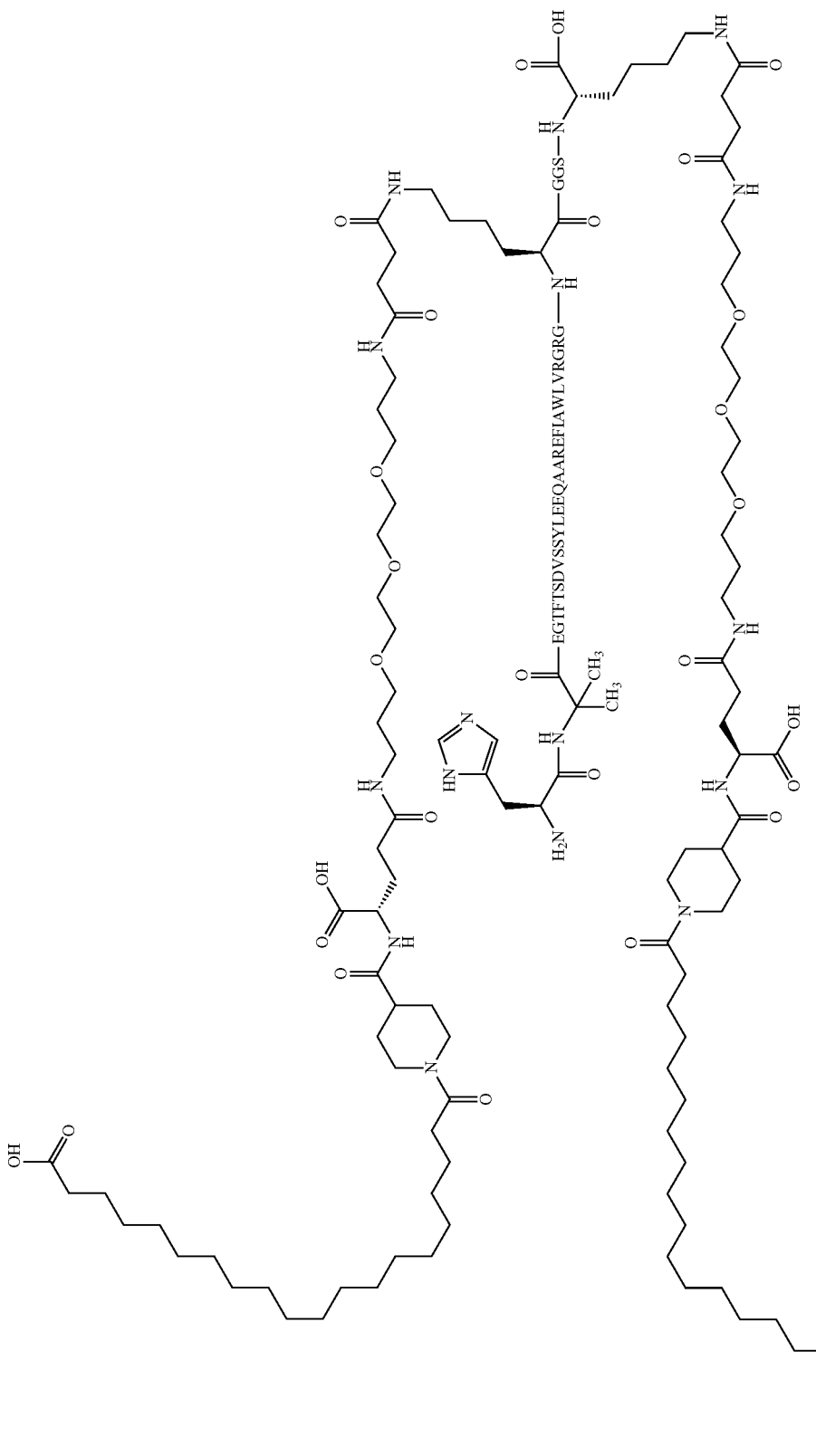
where the amino acid sequence is that of SEQ ID NO: 4,

Chem. 42
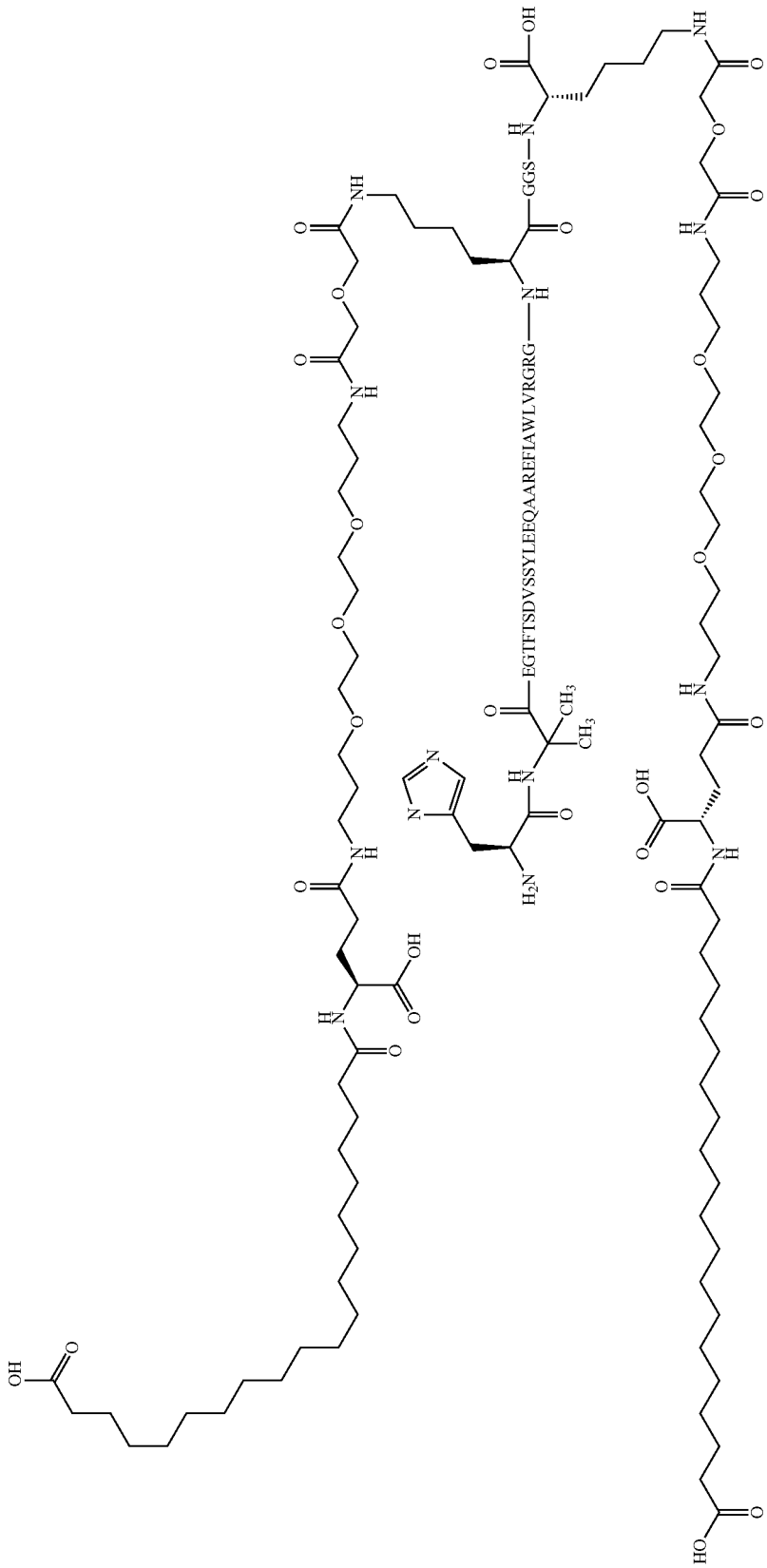
where the amino acid sequence is that of SEQ ID NO: 4,

Chem. 43
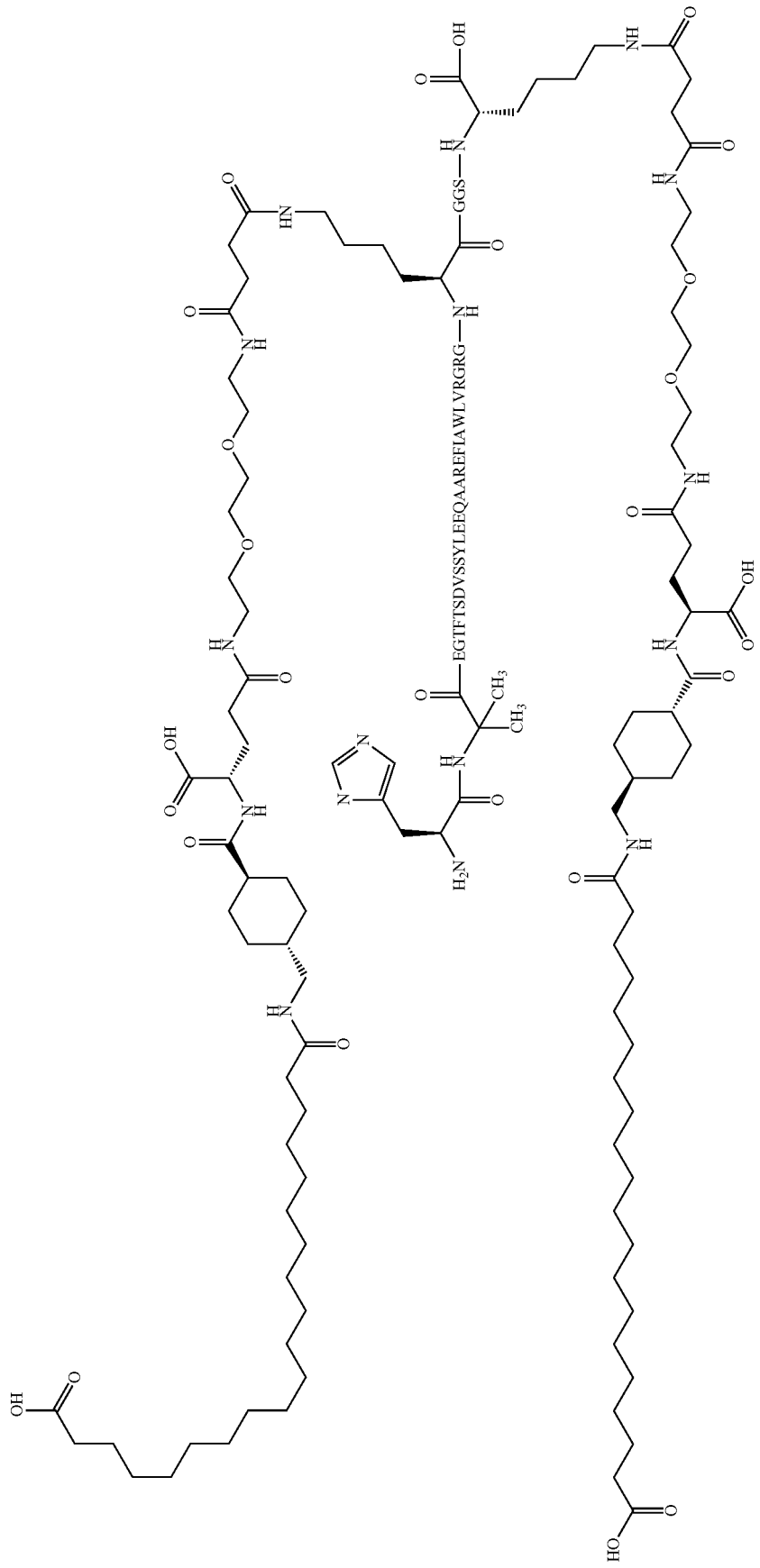
where the amino acid sequence is that of SEQ ID NO: 4,

Chem. 44
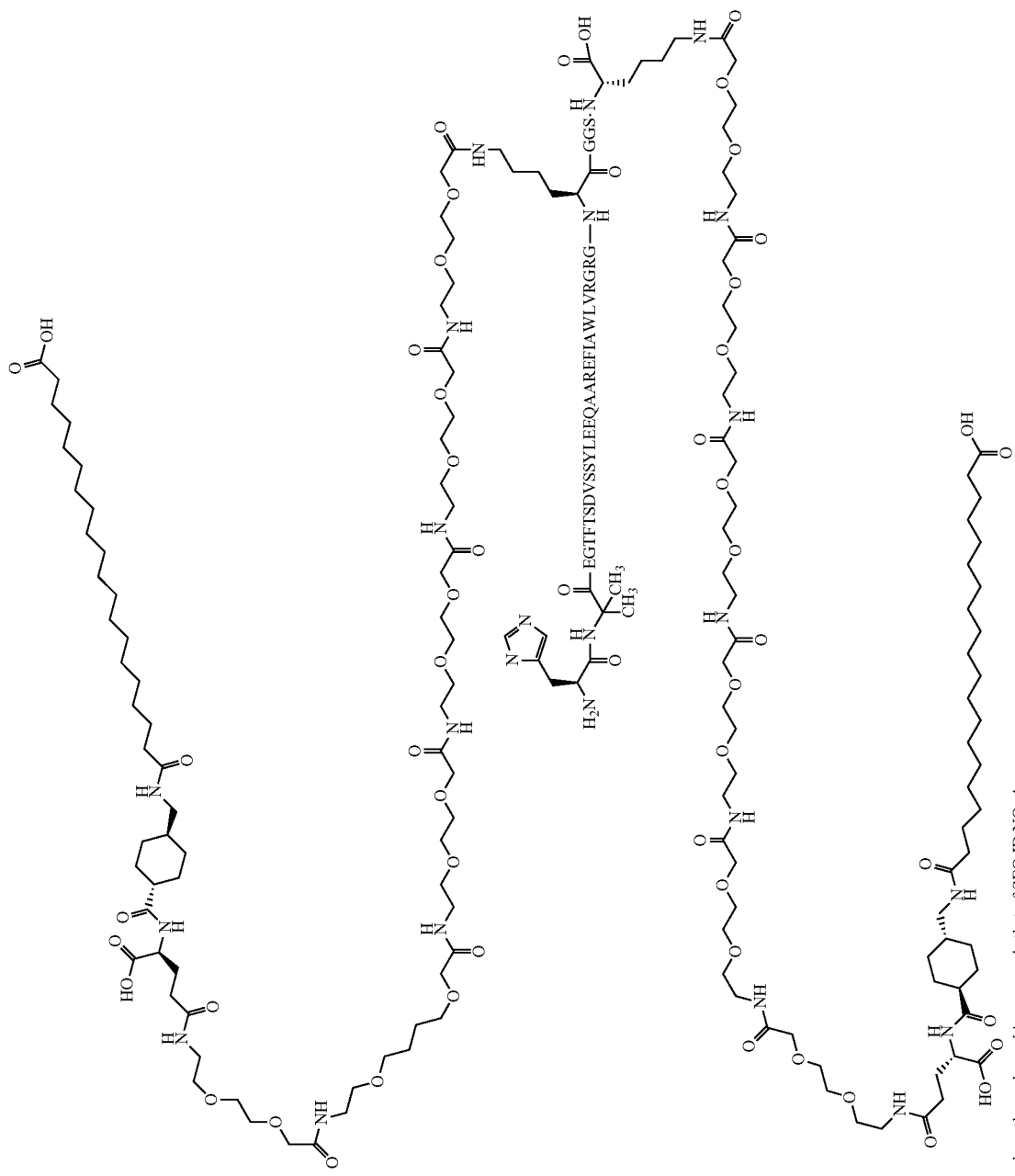
where the amino acid sequence is that of SEQ ID NO: 4,

Chem. 45
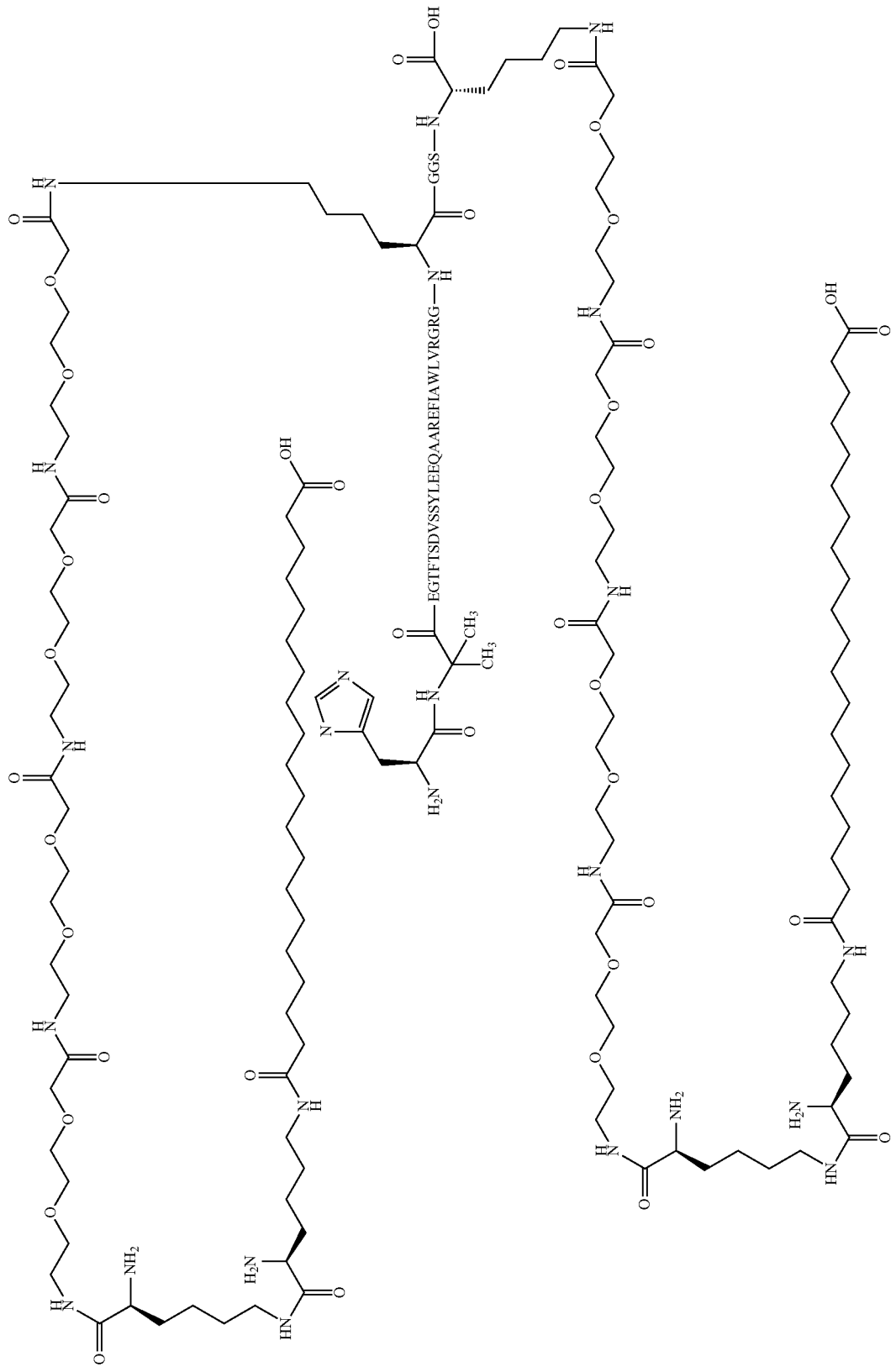
where the amino acid sequence is that of SEQ ID NO: 4,

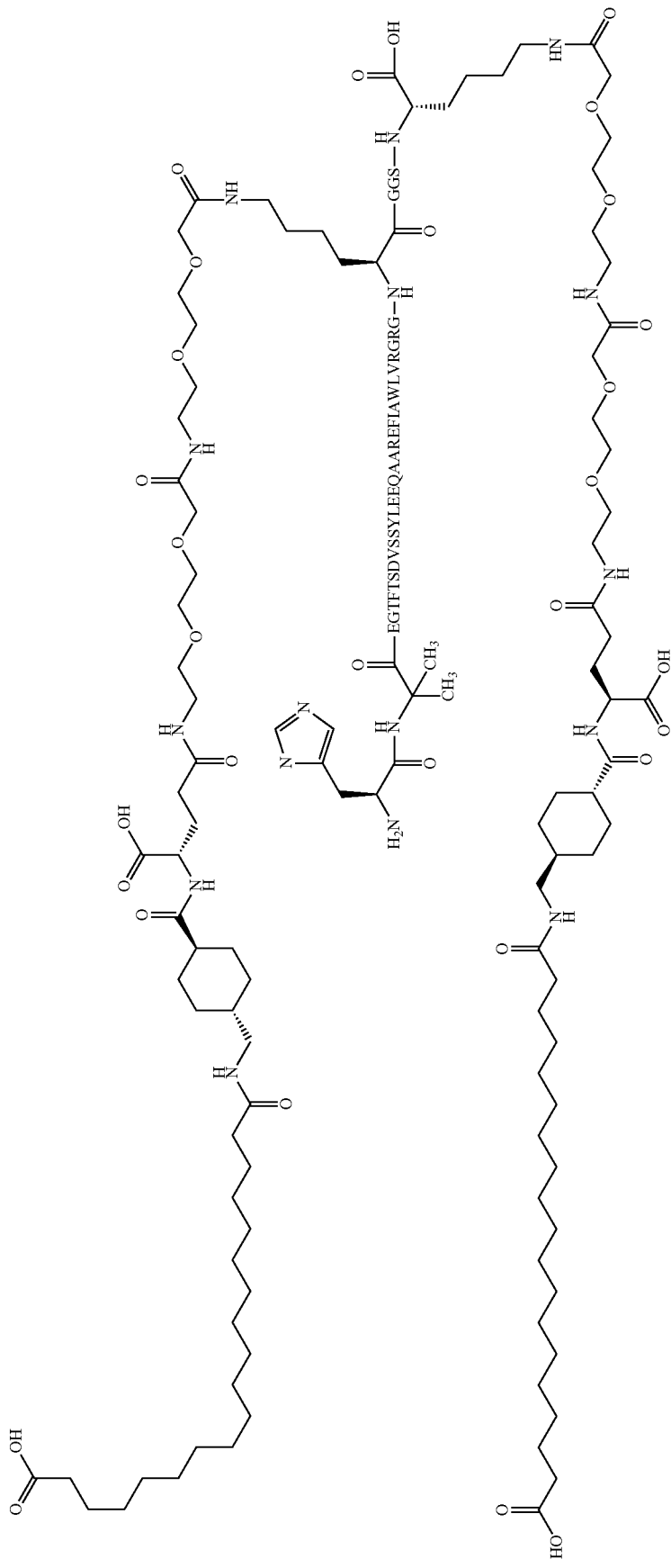
Chem. 46
where the amino acid sequence is that of SEQ ID NO: 4,

Chem. 47
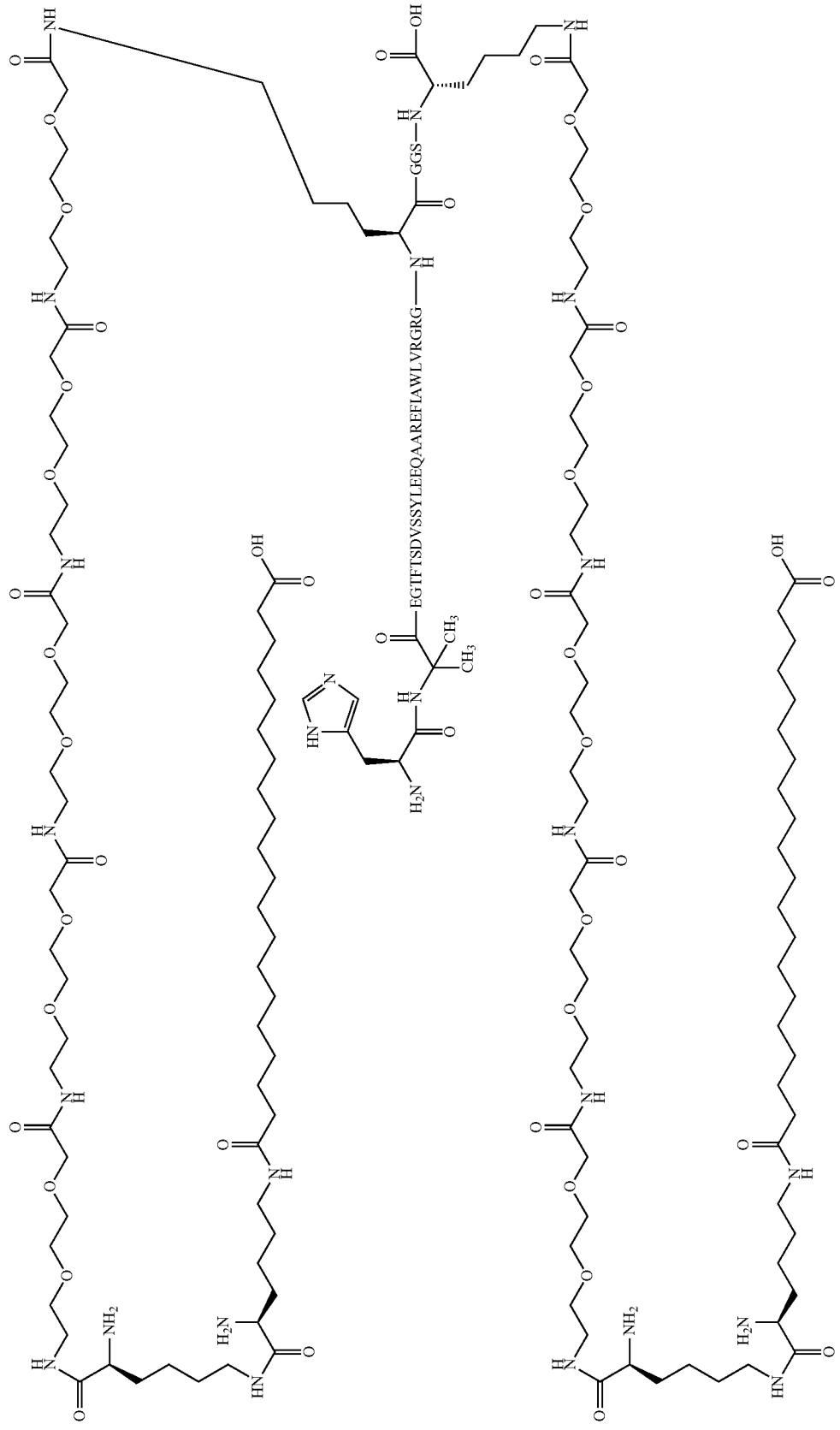
where the amino acid sequence is that of SEQ ID NO: 4,

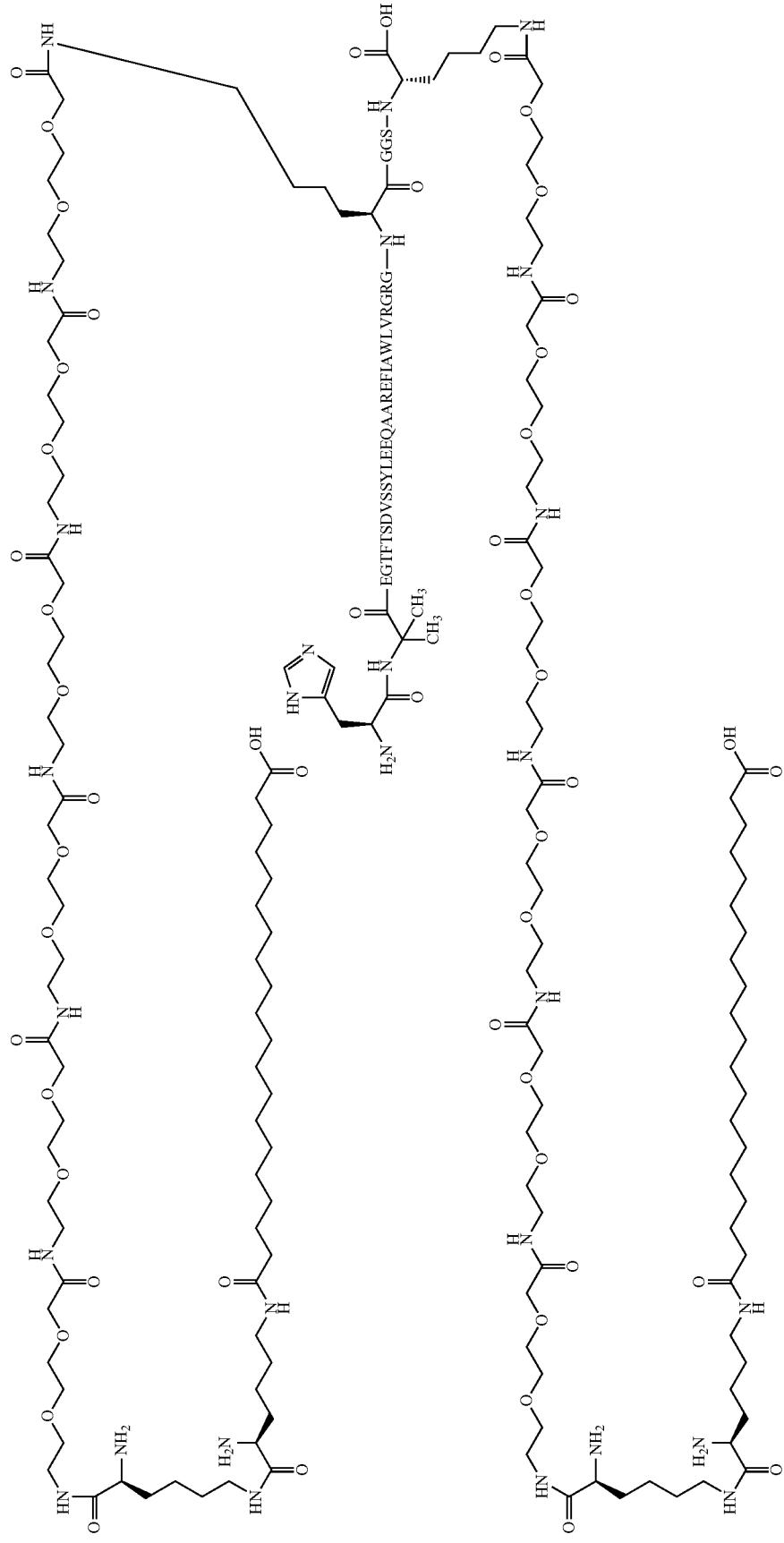

where the amino acid sequence is that of SEQ ID NO:4; or a pharmaceutically acceptable salt, amide, or ester thereof of any of the foregoing derivatives.

16. The derivative of claim 3 wherein the derivative is in the form of a basic salt.

17. The derivative of claim 16, wherein the basic salt is a sodium salt.

18. The derivative of claim 16, wherein the basic salt is a potassium salt.

19. A pharmaceutical composition comprising a derivative according to claim 3 and a pharmaceutically acceptable excipient.

20. The pharmaceutical composition of claim 19, wherein the excipient comprises a phosphate buffer and an isotonic agent.

21. The pharmaceutical composition of claim 20, wherein the isotonic agent is propylene glycol.

22. The pharmaceutical composition of claim 21 wherein the derivative is present in said composition in a concentration from 0.1 mg/mL to 100 mg/mL.

23. A method for treating a subject having diabetes, hyperglycemia, type 2 diabetes, impaired glucose tolerance, type 1 diabetes, non-insulin dependent diabetes, MODY (maturity onset diabetes of the young), and/or gestational diabetes, said method comprising administering to a subject in need of such treatment a therapeutically effective amount of the pharmaceutical composition of claim 19.

24. A method for treating obesity in a subject, said method comprising administering to a subject in need of such treatment a therapeutically effective amount of the pharmaceutical composition of claim 19.

25. The derivative of claim 15 wherein the derivative is in the form of a basic salt.

26. The derivative of claim 25, wherein the basic salt is a sodium salt.

27. The derivative of claim 25, wherein the basic salt is a potassium salt.

28. A pharmaceutical composition comprising a derivative according to claim 15 and a pharmaceutically acceptable excipient.

29. The pharmaceutical composition of claim 28, wherein the excipient comprises a phosphate buffer and an isotonic agent.

30. The pharmaceutical composition of claim 29, wherein the isotonic agent is propylene glycol.

31. The pharmaceutical composition of claim 30, wherein the derivative is present in said composition in a concentration from 0.1 mg/mL to 100 mg/mL.

32. A method for treating a subject having hyperglycemia, type 2 diabetes, impaired glucose tolerance, type 1 diabetes, non-insulin dependent diabetes, MODY (maturity onset diabetes of the young), and/or gestational diabetes, said method comprising administering to a subject in need of such treatment a therapeutically effective amount of the pharmaceutical composition of claim 28.

33. A method for treating obesity in a subject, said method comprising administering to a subject in need of such treatment a therapeutically effective amount of the pharmaceutical composition of claim 28.

34. The derivative of claim 15 wherein said derivative is Chem. 23

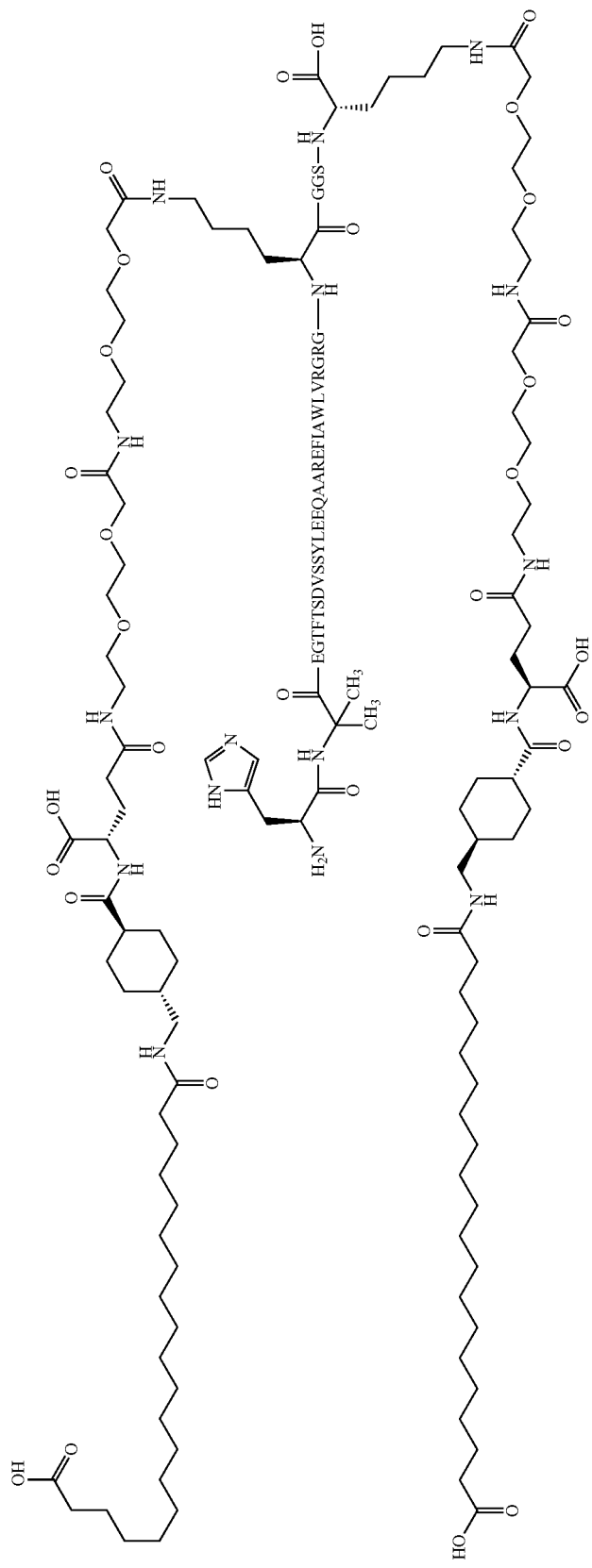

where the amino acid sequence is that of SEQ ID NO:4, or a pharmaceutically acceptable salt, amide, or ester of the derivative.

35. The derivative of claim 15 wherein said derivative is Chem. 27

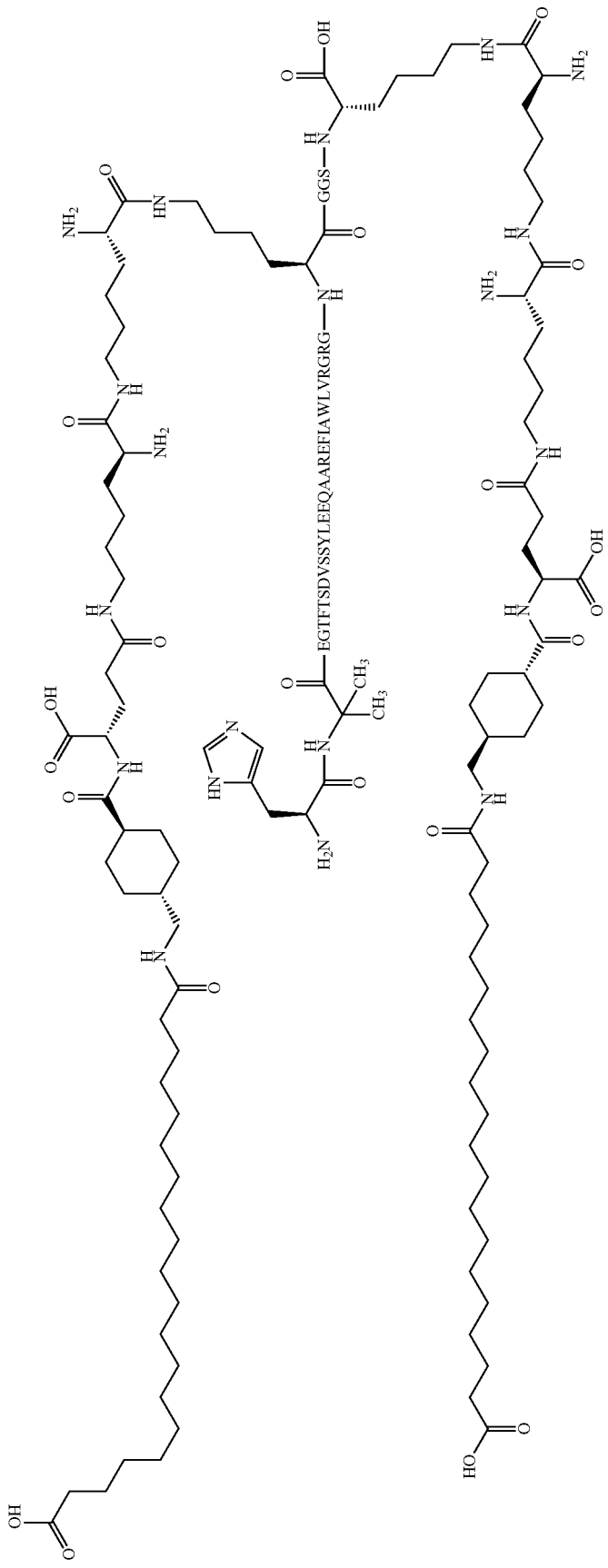

where the amino acid sequence is that of SEQ ID NO:4, or a pharmaceutically acceptable salt, amide, or ester of the derivative.

36. The derivative of claim 15 wherein said derivative is Chem. 29

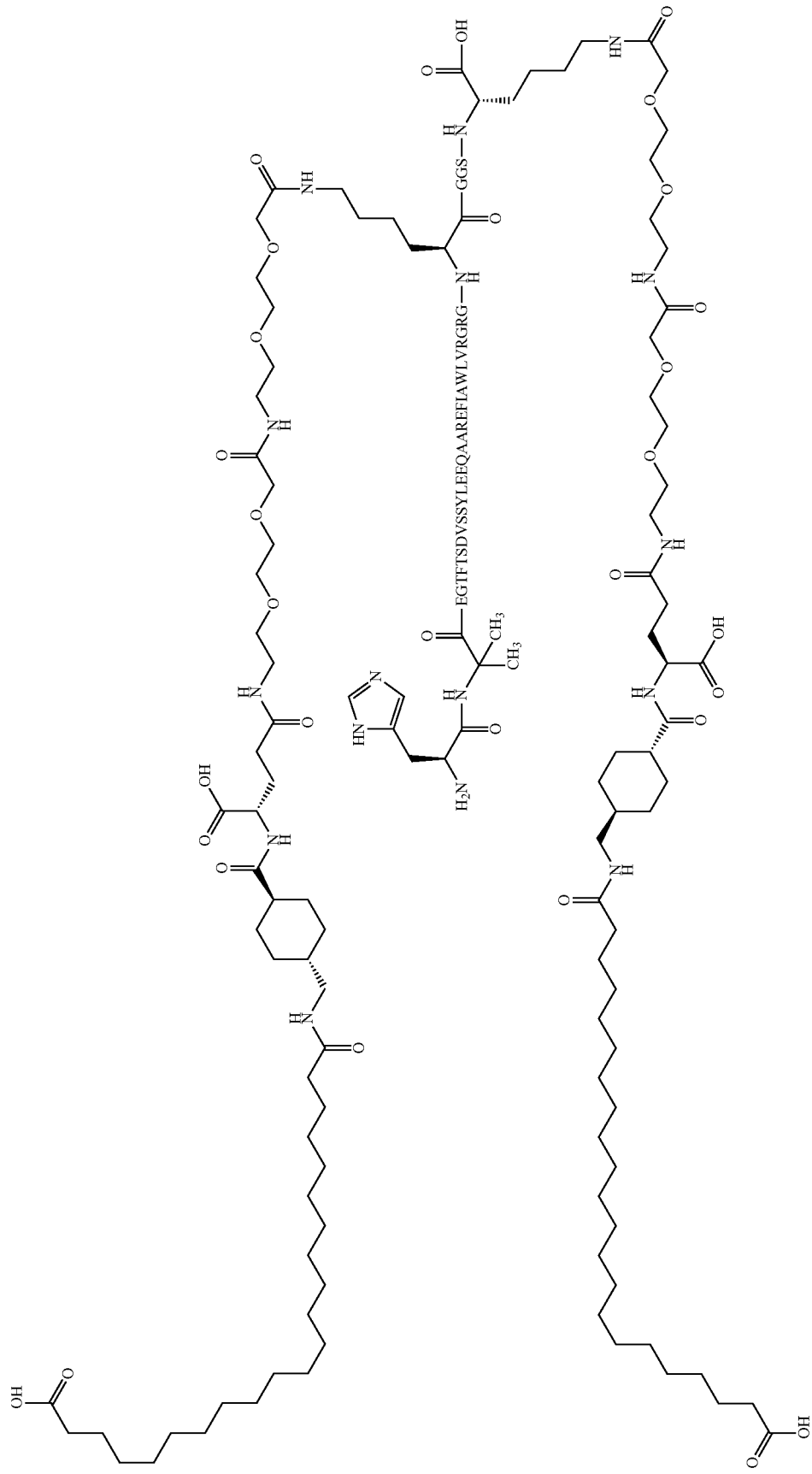

where the amino acid sequence is that of SEQ ID NO:4, or a pharmaceutically acceptable salt, amide, or ester of the derivative.

37. The derivative of claim 15 wherein said derivative is Chem. 30

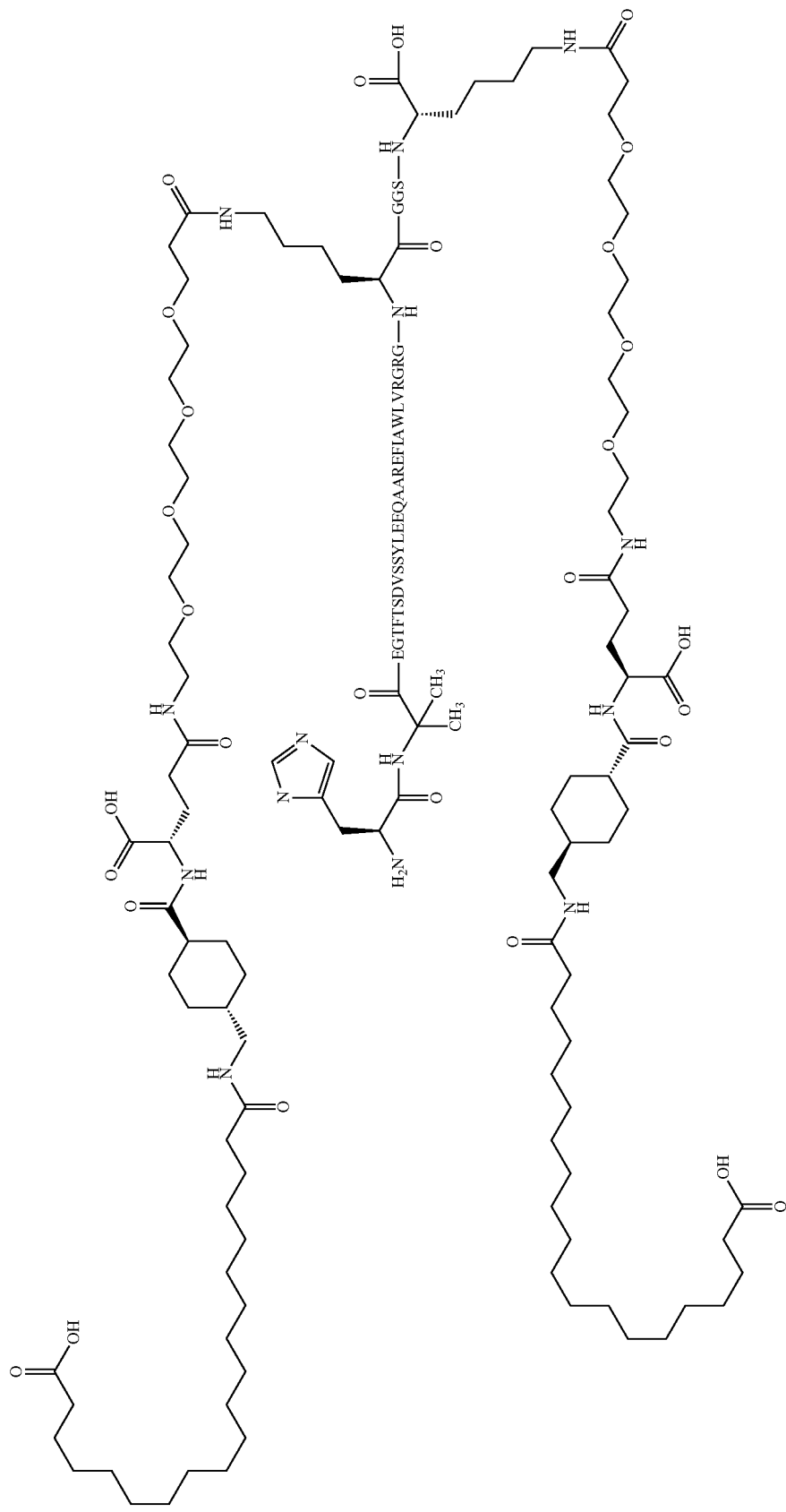

where the amino acid sequence is that of SEQ ID NO:4, or a pharmaceutically acceptable salt, amide, or ester of the derivative.

38. The derivative of claim 15 wherein said derivative is Chem. 47

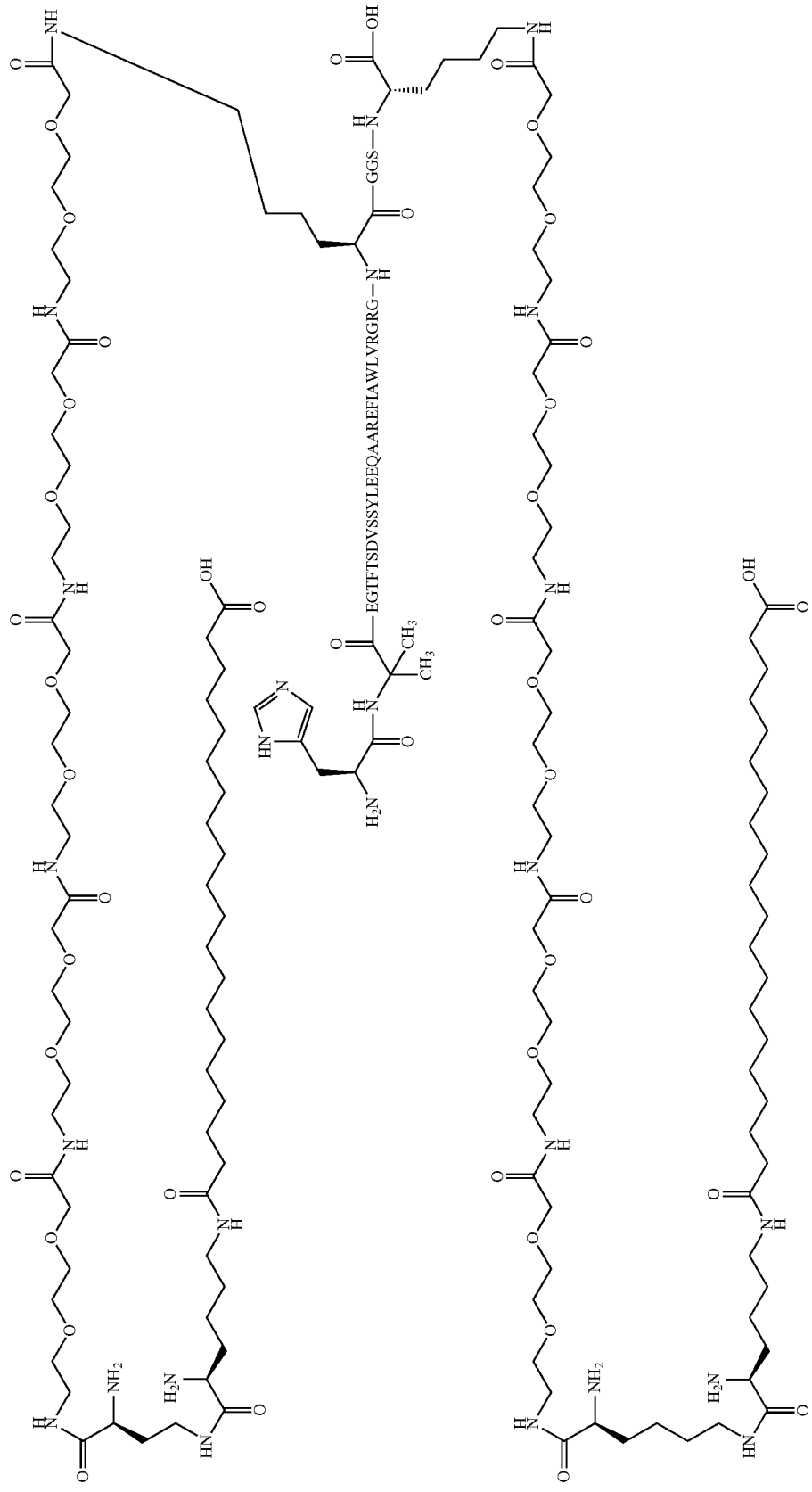

where the amino acid sequence is that of SEQ ID NO:4, or a pharmaceutically acceptable salt, amide, or ester of the derivative.

39. The derivative of claim 15 wherein said derivative is Chem. 48

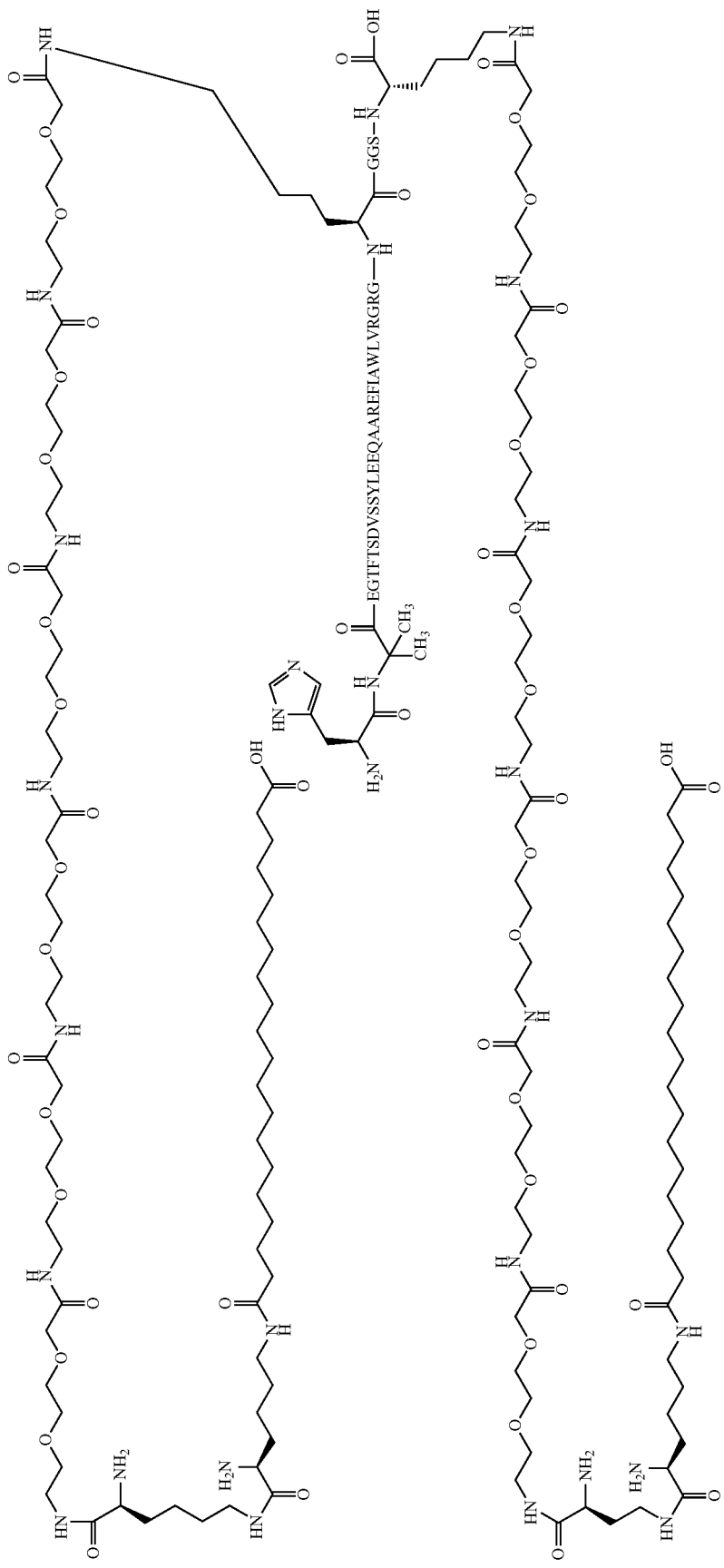

where the amino acid sequence is that of SEQ ID NO:4, or a pharmaceutically acceptable salt, amide, or ester of the derivative.

* * * * *

UNITED STATES PATENT AND TRADEMARK OFFICE
CERTIFICATE OF CORRECTION

PATENT NO. : 9,498,534 B2
APPLICATION NO. : 14/322077
DATED : November 22, 2016
INVENTOR(S) : Steffen Reedtz-Runge et al.

It is certified that error appears in the above-identified patent and that said Letters Patent is hereby corrected as shown below:

In the Claims

In Claim 15, Columns 213-214, at the end of the structure shown in chem. 37, please add the following: "where the amino acid sequence is that of SEQ ID NO:4,"

In Claim 15, Columns 215-216, at the end of the structure shown in chem. 38, please add the following: "where the amino acid sequence is that of SEQ ID NO:8,"

In Claim 15, Columns 217-218, please replace the structure shown in chem. 39 with the following:

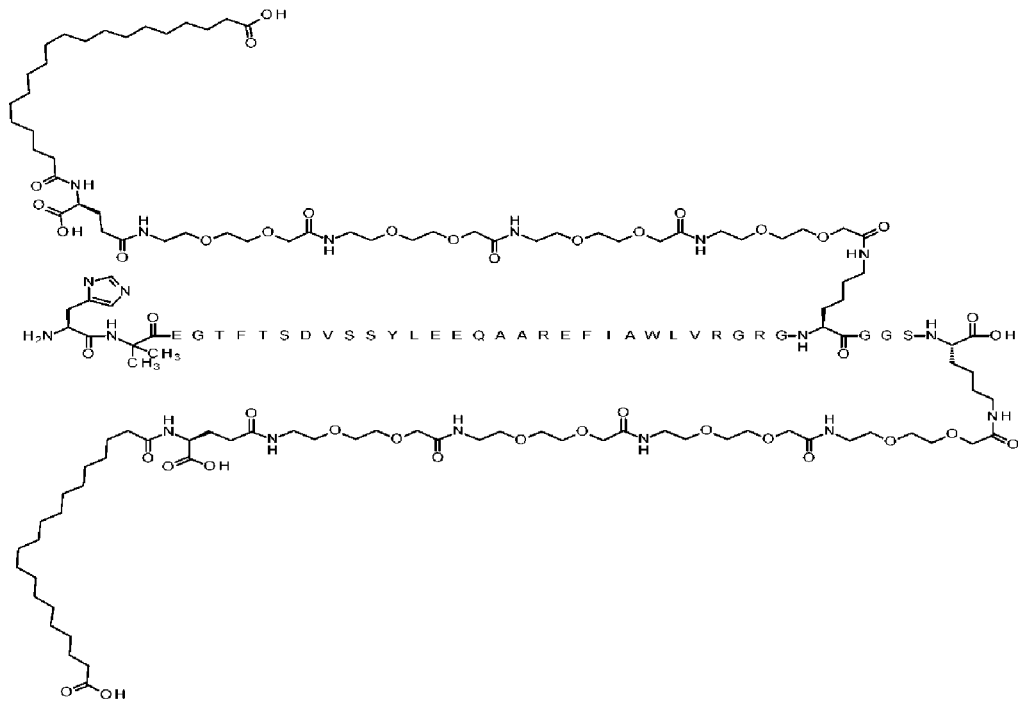

Signed and Sealed this
Twenty-sixth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,498,534 B2

In Claim 15, Columns 219-220, at the end of the structure shown in chem. 40, please add the following: "where the amino acid sequence is that of SEQ ID NO:8,"